United States Patent
Carter et al.

(10) Patent No.: US 6,719,971 B1
(45) Date of Patent: Apr. 13, 2004

(54) METHOD FOR MAKING HUMANIZED ANTIBODIES

(75) Inventors: Paul J. Carter, San Francisco, CA (US); Leonard G. Presta, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 09/705,392

(22) Filed: Nov. 2, 2000

Related U.S. Application Data

(60) Division of application No. 08/146,206, filed as application No. PCT/US92/05126 on Jun. 15, 1992, now Pat. No. 6,407,213, which is a continuation-in-part of application No. 07/715,272, filed on Jun. 14, 1991, now abandoned.

(51) Int. Cl.$^7$ ............................................. A61K 39/395
(52) U.S. Cl. .............................. 424/130.1; 424/133.1; 424/136.1; 424/155.1; 424/141.1; 530/387.1; 530/388.1; 530/388.8; 530/388.85; 435/7.1
(58) Field of Search ..................... 435/7.1; 424/130.1, 424/133.1, 136.1, 155.1, 141.1; 530/387.1, 388.1, 388.8, 388.85

(56) References Cited

U.S. PATENT DOCUMENTS

| | | |
|---|---|---|
| 4,753,894 A | 6/1988 | Frankel et al. |
| 4,816,567 A | 3/1989 | Cabilly et al. |
| 4,845,198 A | 7/1989 | Urdal et al. |
| 4,968,603 A * | 11/1990 | McGuire et al. |
| 5,132,405 A | 7/1992 | Huston et al. |
| 5,169,774 A | 12/1992 | Frankel et al. |
| 5,225,539 A | 7/1993 | Winter |
| 5,530,101 A | 6/1996 | Queen et al. |
| 5,545,403 A | 8/1996 | Page |
| 5,545,404 A | 8/1996 | Page |
| 5,545,405 A | 8/1996 | Page |
| 5,558,864 A | 9/1996 | Bendig et al. |
| 5,585,089 A | 12/1996 | Queen et al. |
| 5,677,171 A | 10/1997 | Hudziak et al. |
| 5,693,761 A | 12/1997 | Queen et al. |
| 5,693,762 A | 12/1997 | Queen et al. |
| 5,714,350 A | 2/1998 | Co et al. |
| 5,720,937 A | 2/1998 | Hudziak et al. |
| 5,720,954 A | 2/1998 | Hudziak et al. |
| 5,725,856 A | 3/1998 | Hudziak et al. |
| 5,770,195 A | 6/1998 | Hudziak et al. |
| 5,772,997 A | 6/1998 | Hudziak et al. |
| 5,821,337 A | 10/1998 | Carter et al. |
| 5,834,598 A | 11/1998 | Lowman et al. |
| 5,859,205 A | 1/1999 | Adair et al. |
| 5,877,293 A | 3/1999 | Adair et al. |
| 5,929,212 A | 7/1999 | Jolliffe et al. |
| 5,994,510 A | 11/1999 | Adair et al. |
| 6,054,297 A | 4/2000 | Carter et al. |
| 6,054,561 A | 4/2000 | Ring |
| 6,180,370 B1 | 1/2001 | Queen et al. |
| 6,350,861 B1 | 2/2002 | Co et al. |
| 6,407,213 B1 | 6/2002 | Carter et al. |

FOREIGN PATENT DOCUMENTS

| | | |
|---|---|---|
| AU | 85058/91 | 3/1992 |
| EP | 120694 | 10/1984 |
| EP | 125023 A1 | 11/1984 |
| EP | 239400 | 9/1987 |
| EP | 323806 A1 | 7/1989 |
| EP | 327000 | 8/1989 |
| EP | 338745 A1 | 10/1989 |
| EP | 365209 A2 | 4/1990 |
| EP | 365997 A2 | 5/1990 |
| EP | 368684 | 5/1990 |
| EP | 403156 A1 | 12/1990 |
| EP | 438310 A2 | 7/1991 |
| EP | 438312 | 7/1991 |
| EP | 440351 | 8/1991 |
| EP | 0 460 167 B1 | 12/1991 |
| EP | 0 519 596 A1 | 12/1992 |
| EP | 0 592 106 A1 | 4/1994 |
| EP | 620276 | 10/1994 |
| EP | 682040 A1 | 11/1995 |
| EP | 451216 B1 | 1/1996 |
| EP | 432249 B1 | 9/1996 |
| EP | 549581 | 1/1997 |
| EP | 328404 A1 | 8/1999 |
| GB | 2 188941 | 10/1987 |
| WO | WO 87/02671 | 5/1987 |
| WO | WO 88/09344 | 12/1988 |
| WO | WO 89/01783 | 3/1989 |
| WO | WO 89/06692 | 7/1989 |
| WO | WO 89/09622 | 9/1989 |
| WO | WO 90/07861 | 7/1990 |
| WO | WO 91/07492 | 5/1991 |
| WO | WO 91/07500 | 5/1991 |
| WO | WO 91/09966 | 7/1991 |
| WO | WO 91/09967 | 7/1991 |
| WO | WO 91/09968 | 7/1991 |
| WO | WO 92/01047 | 1/1992 |
| WO | WO 92/04380 | 3/1992 |
| WO | WO 92/04381 | 3/1992 |
| WO | WO 92/05274 | 4/1992 |
| WO | WO 92/11383 | 7/1992 |
| WO | WO 92/11018 | 9/1992 |
| WO | WO 92/15683 | 9/1992 |
| WO | WO 92/16562 | 10/1992 |
| WO | WO 92/22653 | 12/1992 |
| WO | WO 93/02191 | 2/1993 |
| WO | 94/11509 | 5/1994 |
| WO | WO 94/12214 | 6/1994 |
| WO | WO 99/60023 | 11/1999 |

OTHER PUBLICATIONS

1/ Roitt, I et al (eds). Immunol. 14$^{th}$ ed. Mosby, London, p. 9.6, 1998.*
2/ Kimmel J. Neurosurg 66 : 161–171, 1987.*

(List continued on next page.)

*Primary Examiner*—Susan Ungar
*Assistant Examiner*—Minh Tam Davis
(74) *Attorney, Agent, or Firm*—Wendy M. Lee

(57) ABSTRACT

Variant immunoglobulins, particularly humanized antibody polypeptides are provided, along with methods for their preparation and use. Consensus immunoglobulin sequences and structural models are also provided.

5 Claims, 9 Drawing Sheets

OTHER PUBLICATIONS

3/ Freshney. Culture of Animal cells, A manual of Basicc Tech., Alan Liss Inc, N.Y. p. 4., 1983.*

4/ Dermer, Bio/Technology 12: 320, 1994.*

5/ Sherman, LA, Crit. Rev. Immunol. 18(1–2) : 47–54, 1998.*

6/ Grupa. Science 278 : 1041–1042, 1997.*

7/ Jain. Sci. Am. 271 : 58–65, 1994.*

8/ Curti, Crit. Rev. Oncol/Hematol. 14 : 29–39, 1993.*

9/ Hartwell, Science, 278 : 1064–1068, 1997.*

10/ Boon . Adv. Cancer Res. 58 : 177–210, 1992.*

Debrin, JA, 1986, Proceed Natl Acad Sci, USA, 83 (23): 9129–33.*

Primus FJ et al, 1990, Cancer Immunology, Immunotherapy:CII (Germany, WEST) 31(6): 349–57.*

Riechmann, L, 1988, Nature, 332: 323–327.*

Zu Putlitz, J, 1990, Bio/technology, 8(7): 651–4.*

William E. Paul, M.D. ed., 3d ed. 1993, FUNDAMENTAL, p. 242.*

Rhodes, P., "Recombinant antibodies from CHO cells" *Abstr Pap Am Chem Soc* (Abstract No. 60 from the 199th American Chemical Society National Meeting held in Boston, MA Apr. 22–27, 1990) 199 (1–2) :BIOT 60 (Apr. 1990).

U.S. patent application Ser. No. 07/934,373, Carter et al., filed Aug. 21, 1992.

U.S. patent application Ser. No. 08/437,642, Carter et al., filed May 9, 1995.

U.S. patent application Ser. No. 09/115,800, Carter et al., filed Jul. 15, 1998.

Adair et al., "Humanization of the murine anti–human CD3 monoclonal antibody OKT3" *Hum. Antibod. Hybridomas* 5:41–47 (1994).

Amit et al., "Three–Dimensional Structure of an Antigen–Antibody Complex at 2.8 A Resolution" *Science* 233:747–753 (Aug. 1986).

Amzel and Poljak, "Three–dimensional structure of immunoglobulins" *Ann. Rev. Biochem.* 48:961–967 (1979).

Amzel et al., "The Three Dimensional Structure of a Combining Region–Ligand Complex of Immunoglobulin NEW at 3.5–A Resolution" *Proc. Natl. Acad. Sci. USA* 71(4) :1427–1430 (Apr. 1974).

Baselga et al., "Phase II Study of Weekly Intravenous Recombinant Humanized Anti–p185$^{HER2}$ Monoclonal Antibody in Patients With HER2/neu–Overexpressing Metastatic Breast Cancer" *J. Clin. Oncol.* 14 (3) : 737–744 (Mar. 1996).

Beverley & Callard, "Distinctive functional characteristics of human "T" lymphocytes defined by E rosetting or a monoclonal anti–T cell antibody" *European Journal of Immunology* 11:329–334 (1981).

Bindon et al., "Human monoclonal IgG isotypes differ in complement activating function at the level of C4 as well as Clq" *Journal of Experimental Medicine* 168(1):127–142 (Jul. 1988).

Bird et al., "Single–chain antigen–binding proteins" *Science* 242:423–426 (Oct. 1988).

Boulianne et al., "Production of functional chimaeric mouse/human antibody" *Nature* 312:643–646 (Dec. 13, 1984).

Brennan et al., "Preparation of bispecific antibodies by chemical recombination of monoclonal immunoglobulin $G_1$ fragments" *Science* 229:81–83 (Jul. 1985).

Brown et al., "Anti–Tac–H, a humanized antibody to the interleukin 2 receptor, prolongs primate cardiac allograft survival" *Proc. Natl. Acad. Sci. USA* 88:2663–2667 (Apr. 1991).

Brown, Jr. et al., "Anti–Tac–H, a humanized antibody to the interleukin 2 receptor, prolongs primate cardiac allograft survival" *Proc. Natl. Acad. Sci. USA* 88:2663–2667 (1991).

Bruccoleri et al., "Structure of antibody hypervariable loops reproduced by a conformational search algorithm" *Nature* 335:564–568 (Oct. 1988).

Bruccoleri, "Structure of antibody hypervariable loops reproduced by a conformational search algorithm" *Nature* 336:266 (1988).

Bruggemann, M. et al., "Comparison of the effector functions of human immunoglobulins using a matched set of chimeric antibodies" *Journal of Experimental Medicine* 166:1351–1361 (1987).

Burgess et al., "Possible Dissociation of the Heparin–binding and Mitogenic Activities of Heparin–binding (Acidic Fibroblast) Growth Factor–1 from Its Receptor–binding Activities by Site–directed Mutagenesis of a Single Lysine Residue" *Journal of Cell Biology* 111:2129–2138 (1990).

Caron et al., "Biological and Immunological Features of Humanized M195 (Anti–CD33) Monoclonal Antibodies" *Cancer Research* 52:6761–6767 (Dec. 1992).

Carter et al., "High level *Escherichia coli* expression and production of a bivalent humanized antibody fragment" *Bio/Technology* 10:163–167 (1992).

Carter et al., "Humanization of an anti–p185$^{HER2}$ antibody for human cancer therapy" *Proc. Natl. Acad. Sci.* 89:4285–4289 (May 1992).

Casale et al., "Use of an anti–IgE humanized monoclonal antibody in ragweed–induced allergic rhinitis" *J. Allergy Clin. Immunol.* 100:110–121 (1997).

Cheetham, J., "Reshaping the antibody combining site by CDR replacement–tailoting or tinkering to fit?" *Protein Engineering* 2(3):170–172 (1988).

Chothia & Lesk, "The relation between the divergence of sequence and structure in proteins" *EMBO Journal* 5(4):823–826 (1986).

Chothia and Lesk, "Canonical structures for the hypervariable regions of immunoglobulins" *J. Mol. Biol.* 196(4):901–917 (1987).

Chothia et al., "Domain Association in Immunoglobulin Molecules. The Packing of Variable Domains" *Journal of Molecular Biology* 186:651–663 (1985).

Chothia et al., "Principles of protein–protein recognition" *Nature* 256:705–708 (1975).

Chothia et al., "The predicted structure of immunoglobulin D1.3 and its comparison with the crystal structure" *Science* 233:755–758 (Aug. 15, 1986).

Chothia et al., "Transmission of conformational change in insulin" *Nature* 302:500–505 (1983).

Chothia, C. et al., "Conformations of immunoglobulin hypervariable regions" *Nature* 342(6252):877–883 (1989).

Clark et al., "The improved lytic function and in vivo efficacy of monovalent monoclonal CD3 antibodies" *European Journal of Immunology* 19:381–388 (1989).

Co & Queen, "Humanized antibodies for therapy" *Nature* 351:501–502 (Jun. 1991).

Co et al., "Chimeric and Humanized Antibodies with Specificity for the CD33 Antigen" *J. of Immunology* 148(4):1149–1154 (Feb. 1992).

Co et al., "Humanized Anti–Lewis Y Antibodies: In Vitro Properties and Pharmacokinetics in Rhesus Monkeys" *Cancer Research* 56:1118–1125 (Mar. 1996).

Co et al., "Humanized antibodies for antiviral therapy" *Proc. Natl. Acad. Sci. USA* 88:2869–2873 (Apr. 1991).

Colman et al., "Crystal and Molecular Structure of the Dimer of Variable Domains of the Bence–Jones Protein ROY" *J. Mol. Biol.* 116:73–79 (1977).

Colman et al., "Three–dimensional structure of a complex of antibody with influenza virus neuraminidase" *Nature* 326:358–363 (Mar. 1987).

Cook et al., "A map of the human immunoglobulin $V_H$ locus completed by analysis of the telometric region of chromosome 14q" *Nature Genetics* 7:162–168 (Jun. 1994).

Corti et al., "Idiotope Determining Regions of a Mouse Monoclonal Antibody and Its Humanized Versions" *J. Mol. Biol.* 235:53–60 (1994).

Coussens et al., "Tyrosine Kinase Receptor with Extensive Homology to EGF Receptor Shares Chromosomal Location with neu Oncogene" *Science* 230:1132–1139 (1985).

Couto et al., "Anti–BA46 Monoclonal Antibody Mc3 Humanization Using a Novel Positional Consensus and in Vivo and in Vitro Characterization" *Cancer Research Supplement* 55:1717–1722 (1995).

Couto et al., "Humanization of KC4G3, and Anti–Human Carcinoma Antibody" *Hybridoma* 13:215–219 (1994).

Darsley & Rees, "Nucleotide sequences of five anti–lysozyme monoclonal antibodies" *EMBO Journal* 4(2):393–398 (1985).

Daugherty et al., "Polymerase chain reaction facilitates the cloning, CDR–grafting, and rapid expression of a murine monoclonal antibody directed against the CD18 component of leukocyte integrins" *Nucleic Acids Research* 19(9):2471–2476 (May 11, 1991).

Davies & Metzger, "Structural Basis of Antibody Function" *Ann. Rev. Immunol.* 1:87–117 (1983).

Davies et al., "Antibody–Antigen Complexes" *Journal of Biological Chemistry* 263(22):10541–10544 (Aug. 1988).

Davies et al., "Antibody–Antigen Complexes" *Ann. Rev. Biochem.* 59:439–473 (1990).

Eigenbrot et al., "X–Ray Structures of Fragments From Binding and Nonbinding Versions of a Humanized Anti–CD18 Antibody: Structural Indications of the Key Role of $V_H$ Residues 59 to 65" *Proteins: Structure, Function, and Genetics* 18:49–62 (1994).

Eigenbrot et al., "X–ray structures of the antigen–binding domains from three variants of humanized anti–p185$^{HER2}$ antibody 4D5 and comparison with molecular modeling" *J. Mol. Biol.* 229:969–995 (1993).

Ellis et al., "Engineered Anti–CD38 Monoclonal Antibodies for Immunotherapy of Multiple Myeloma" *The Journal of Immunology* pps. 925–937 (1995).

Ellison et al., "The nucleotide sequence of a human immunoglobulin $C_{\gamma 1}$ gene" *Nucleic Acids Research* 10(13):4071–4079 (1982).

Emery & Adair, "Humanised monoclonal antibodies for therapeutic applications" *Exp. Opin. Invest. Drugs* 3(3):241–251 (1994).

Epp et al., "Crystal and Molecular Structure of a Dimer Composed of the Variable Portions of the Bence–Jones Protein REI" *European Journal of Biochemistry* 45:513–524 (1974).

Epp et al., "The molecular structure of a dimer composed of the variable portions of the Bence–Jones protein REI refined at 2.0–A resolution" *Biochemistry* 14(22):4943–4952 (1975).

Fahy et al., "The Effect of an Anti–IgE Monoclonal Antibody on the Early– and Late–Phase Responses to Allergen Inhalation in Asthmatic Subjects" *Am J. Respir. Crit. Care Med* 155:1828–1834 (1997).

Fanger et al., "Bispecific antibodies and targeted cellular cytotoxicity" *Immunology Today* 12(2):51–54 (1991).

Fanger et al., "Cytotoxicity mediated by human Fc receptors for IgG" *Immunology Today* 10(3):92–99 (1989).

Feldmann et al., "A Hypothetical Space–Filling Model of the V–Regions of the Galactan–Binding Myeloma Immunoglobulin J539" *Molecular Immunology* 18(8):683–698 (1981).

Fendley et al., "The Extracellular Domain of HER2/neu Is a Potential Immunogen for Active Specific Immunotherapy of Breast Cancer" *J. Biol. Resp. Mod.* 9:449–455 (1990).

Fendly et al., "Characterization of Murine Monoclonal Antibodies Reactive to Either the Human Epidermal Growth Factor Receptor or HER2/neu Gene Product" *Cancer Research* 50:1550–1558 (Mar. 1, 1990).

Foote et al., "Antibody Framework Residues Affecting the Conformation of the Hypervariable Loops" *J. Mol. Biol.* 224:487–499 (1992).

Foote, J., "Humanized Antibodies" *Nova acta Leopoldina* 61(269):103–110 (1989).

Furey et al., "Structure of a novel Bence–Jones protein (Rhe) fragment at 1.6 A resolution" *J. Mol. Biol.* 167(3):661–692 (Jul. 5, 1983).

Glennie et al., "Preparation and Performance of Bispecific F(ab'γ)$_2$ Antibody Containing Thioether–Linked Fab'γ Fragments" *J. Immunol.* 139(7):2367–2375 (Oct. 1, 1987).

Gonzalez et al., "Humanization of Murine 6G425:An Anti–IL8 Monoclonal Antibody Which Blocks Binding of IL8 to Human Neutrophils" *1996 Keystone Symposia on Exploring and Exploiting Antibody and Ig Superfamily Combining Sites* (Poster) pps. 1–21 (Feb. 1996).

Gorman et al., "Reshaping a therapeutic CD4 antibody" *Proc. Natl. Acad. Sci. USA* 88(10):4181–4185 (May 15, 1991).

Gregory et al., "The solution conformations of the subclasses of human IgG deduced from sedimentation and small angle X–ray scattering studies" *Molecular Immunology* 24(8):821–829 (Aug. 1987).

Gussow & Seemann, "Humanization of Monoclonal Antibodies" *Meth. Enzymology*, Academic Press, Inc. vol. 203:99–121 (1991).

Hale, G. et al., "Remission induction in non–Hodgkin lymphoma with reshaped human monoclonal antibody CAMPATH–1H" *Lancet* 2(8625):1394–1399 (Dec. 17, 1988).

Harris et al., "Therapeutic Antibodies—The Coming of Age" *TIBTECH* 11:42–44 (Feb. 1993).

Hieter et al., "Cloned human and mouse kappa immunoglobulin constant and J region genes conserve homology in functional segments" *Cell* 22(Part 1):197–207 (1980).

Hieter et al., "Evolution of Human Immunoglobulin K J Region Genes" *The Journal of Biological Chemistry* 257:1516–1522 (1982).

Houghton, A., "Building a better monoclonal antibody" *Immunology Today* 9(9):265–267 (1988).

Huber et al., "Crystallographic structure studies of an IgG molecule and an Fc fragment" *Nature* 264:415–420 (Dec. 2, 1976).

Hudziak et al., "p185$^{HER2}$ Monoclonal Antibody Has Antiproliferative Effects In Vitro and Sensitizes Human Breast Tumor Cells to Tumor Necrosis Factor" *Molecular & Cellular Biology* 9(3):1165–1172 (Mar. 1989).

Huston et al., "Protein engineering of antibody binding sites: Recovery of specific activity in an anti–digoxin single–chain Fv analogue produced in *Escherichia coli*" *Proc. Natl. Acad. Sci. USA* 85:5879–5883 (Aug. 1988).

Isaacs et al., "Humanised Monoclonal Antibody Therapy for Rheumatoid Arthritis" *Lancet* 340:748–752 (Sep. 26, 1992).

Jaffers et al., "Monoclonal Antibody Therapy, Anti–Idiotypic and Non–Anti–Idiotypic Antibodies to OKT3 Arising Despite Intense Immunosuppression" *Transplantation* 41(5):572–578 (May 1986).

Johnson et al., "Biological and Molecular Modeling Studies Comparing Murine Monoclonal Antibodies with Their Engineered Chimeric and Humanized Counterparts" *J. Cell. Biochem. Suppl 0 (13 Part A)* (18th Ann. UCLA Symp on Mol. & Cell. Biol., Park City, UT Jan. 17–22, 1989) pps. 87 (1989).

Jones et al., "Replacing the Complementarity–determining Regions in a Human Antibody with Those From a Mouse" *Nature* 321:522–525 (May 29, 1986).

Junghans et al., "Anti–Tac–H, a Humanized Antibody to the Interleukin 2 Receptor with New Features for Immunotherapy in Malignant and Immune Disorders" *Cancer Research* 50(5):1495–1502 (Mar. 1, 1990).

Kabat E., "Origins of Antibody Complementarity and Specificity—Hypervariable Regions and the Minigenen Hypothesis" *J. of Immunology* 125(3):961–969 (Sep. 1980).

Kabat et al. *Sequences of Proteins of Immunological Interest*, Bethesda, MD:National Institutes of Health pps. iii–xxiii, 41–76 and 160–167 (1987).

Kabat et al. *Sequences of Proteins of Immunological Interest*, U.S. Dept. of Health and Human Services, NIH, 5th edition vol. 1:103–108, 324–331 (1991).

Kabat et al., "Sequences of Proteins of Immunological Interest", Bethesda, MD:National Institute of Health pps. 14–32 (1983).

Kabat et al., "Sequences of Proteins of Immunological Interest, 4th Edition" pps. iii–xxvii, 41–76, 160–175 (1987).

Kettleborough et al., "Humanization of a Mouse Monoclonal Antibody by CDR–grafting: the Importance of Framework Residues on Loop Conformation" *Protein Engineering* 4(7):773–783 (1991).

Kindt & Capra *The Antibody Enigma*, New York:Plenum Press pps. 79–86 (1984).

King et al., "Amplification of a Novel v–erbB–Related Gene in a Human Mammary Carcinoma" *Science* 229:974–976 (Sep. 1985).

Lazar et al., "Transforming Growth Factor α: Mutation of Aspartic Acid 47 and Leucine 48 Results in Different Biological Activities" *Molecular & Cellular Biology* 8(3):1247–1252 (Mar. 1988).

Lesk & Chothia, "Evolution of Proteins Formed by β–Sheets" *J. Mol. Biol.* 160:325–342 (1982).

Lesk & Chothia, "The response of protein structures to amino–acid sequence changes" *Phil. Trans. R. Soc. Lond. A* 317:345–356 (1986).

Lesk, Arthur M., "How Different Amino Acid Sequences Determine Similar Protein Structures: The Structure and Evolutionary Dynamics of the Globins" *J. Mol. Biol.* 136:225–270 (1980).

Love et al, "Recombinant antibodies possessing novel effector functions" *Methods in Enzymology* 178:515–527 (1989).

Lupu et al., "Direct interaction of a ligand for the erbB2 oncogene product with the EGF receptor and p185$^{erbB2}$" *Science* 249:1552–1555 (1990).

Maeda et al., "Construction of Reshaped Human Antibodies with HIV–neutralizing Activity" *Hum. Antibod. Hybridomas* 2:124–134 (Jul. 1991).

Margni RA and Binaghi RA, "Nonprecipitating asymmetric antibodies" *Ann. Rev. Immunol.* 6:535–554 (1988).

Margolies et al., "Diversity of light chain variable region sequences among rabbit antibodies elicited by the same antigens." *Proc. Natl. Acad. Sci. USA* 72:2180–84 (Jun. 1975).

Mariuzza et al., "The Structure Basis of Antigen–Antibody Recognition" *Ann. Rev. Biophys. Biophys. Chem.* 16:139–159 (1987).

Marquart et al., "Crystallographic refinement and atomic models of the intact immunoglobulin molecule Kol and its antigen–binding fragment at 3.0 A and 1.0 A resolution" *J. Mol. Biol.* 141(4):369–391 (Aug. 25, 1980).

Mathieson et al., "Monoclonal–Antibody Therapy in Systemic Vasculitis" *New England J. of Medicine* pps. 250–254 (Jul. 1990).

Matsumura et al., "Hydrophobic stabilization in T4 lysozyme determined directly by multiple substitutions of Ile 3" *Nature* 334:406–410 (1988).

Mian, IS et al., "Structure, function and properties of antibody binding sites" *J. Mol. Biol.* 217(1):133–151 (Jan. 5, 1991).

Miller, R. et al., "Monoclonal antibody therapeutic trials in seven patients with T–cell lymphoma" *Blood* 62:988–995 (1983).

Morrison et al., "Chimeric Human Antibody Molecules: Mouse Antigen–binding Domains with Human Constant Region Domains" *Proc. Natl. Acad. Sci. USA* 81:6851–6855 (Nov. 1984).

Morrison, S. L., "Transfectomas Provide Novel Chimeric Antibodies" *Science* 229:1202–1207 (Sep. 20, 1985).

Nadler et al., "Immunogenicity of Humanized and Human Monoclonal Antibodies" *Clin. Pharmacology & Therapeutics* pps. 180 (Feb. 1994).

Nakatani et al., "Humanization of mouse anti–human IL–2 receptor antibody B–B10" *Protein Engineering* 7:435–443 (1994).

Nelson, H., "Targeted Cellular Immunotherapy with Bifunctional Antibodies" *Cancer Cells* 3:163–172 (1991).

Neuberger et al., "A hapten–specific chimaeric IgE antibody with human physiological effector function" *Nature* 314:268–270 (Mar. 21, 1985).

Neuberger et al., "Antibody Engineering" *Proceedings 8th Intl. Biotech. Symp., Paris* II:792–799 (1988).

Neuberger et al., "Recombinant Antibodies Possessing Novel Effector Functions" *Nature* 312:604–608 (Dec. 13, 1984).

Newmark, P., "Making Chimeric Antibodies Even More Human" *Bio/Technology* 6:468 (May 1988).

Nishimura et al., "Human c–erbB–2 Proto–Oncogene Product as a Target for Bispecific–Antibody–Directed Adoptive Tumor Immunotherapy" *Int. J. Cancer* 50:800–804 (1992).

Nitta et al., "Preliminary trial of specific targeting therapy against malignant glioma" *Lancet* 335(8686):368–371 (Feb. 17, 1990).

Nitta, T. et al., "Bispecific F(ab')₂ monomer prepared with anti–CD3 and anti–tumor monoclonal antibodies is most potent in induction of cytolysis of human T cells" *European Journal of Immunology* 19:1437–1441 (1989).

Nolan et al., "Bifunctional antibodies: concept, production and applications" *Biochimica et Biophysica Acta* 1040:1–11 (1990).

Novotny et al., "Structural invariants of antigen binding: comparison of immunoglobulin $V_L$–$V_H$ and $V_L$–$V_L$ domain dimers" *Proc. Natl. Acad. Sci. USA* 82(14):4592–4596 (Jul. 1985).

O'Connor et al., "Calcium Dependence of an Anti–Protein C Humanized Antibody Involves Framework Residues" (manuscript).

Ohtomo et al., "Humanization of Mouse ONS–M21 Antibody with the Aid of Hybrid Variable Regions" *Molecular Immunology* 32:407–416 (1995).

Orlandi et al., "Cloning Immunoglobulin Variable Domains for Expression by the Polymerase Chain Reaction" *Proc. Natl. Acad. Sci. USA* 86:3833–3837 (May 1989).

Orlandi et al., "Cloning of cDNA Corresponding to Heavy and Light Chain Immunoglobulin Variable Domains" *Protein and Pharmaceutical Engineering* pps. 90 (1989).

Ostberg & Queen, "Human and humanized monoclonal antibodies: preclinical studies and clinical experience" *Biochem. Soc. Transactions* pps. 1038–1043 (1995).

Padlan et al., "Model–Building Studies of Antigen–Binding Sites: The Hapten–Binding Site of MOPC–315" *C.S. Harbor Symp. Quant. Biol.* 41:627–637 (1977).

Padlan et al., "Model–building Studies of Antigen–binding Sites: The Hapten–binding Site MOPC–315" *Cold Springs Harbor Symposia On Quantitative Biology* XLI:627–637 (1977).

Padlan, E., "Anatomy of the Antibody Molecule" *Molecular Immunology* 31(3):169–217 (1994).

Padlan, E., "Evaluation of the Structural Variation Among Light Chain Variable Domains" *Molecular Immunology* 16:287–296 (1979).

Palm & Hilschmann, "Primary structure of a crystalline monoclonal immunoglobulin K–type L–chain, subgroup I (Bence–Jones preotin Rei); isolation & characterization of the tryptic peptides: . . . " *Hoppes–Seyler's Z. Physiol. Chem.* 356:167–191 (Feb. 1975).

Palm & Hilschmann, "The primary structure of a crystalline, monoclonal immunoglobulin–L–chain of the x–type, subgroup I (Bence–Jones Protein Rei): a contribution to the elucidation of the three–dimensional structure of the immunoglobulins" *Hoppe–Seyler's Z. Physiol. Chem.* 354:1651–1654 (Dec. 1973).

Panka et al., "Variable region framework differences result in decreased or increased affinity of variant anti–digoxin antibodies" *Proc. Natl. Acad. Sci. USA* 85:3080–3084 (May 1988).

Pluckthun, Andreas, "Antibody engineering: advances from the use of *Escherichia coli* expression systems" *Biotechnology* 9:545–51 (1991).

Presta et al., "Humanization of an Anti–Vascular Endothelial Growth Factor Monoclonal Antibody for the Therapy of Solid Tumors and Other Disorders" *Cancer Research* 57(20):4593–4599 (Oct. 15, 1997).

Presta et al., "Humanization of an Antibody Directed Against IgE" *J. Immunol.* 151(5):2623–2632 (Sep. 1, 1993).

Preval & Fougereau, "Specific Interaction between $V_H$ and $V_L$ Regions of Human Monoclonal Immunoglobulins" *J. Mol. Biol.* 102:657–678 (1976).

Queen et al., "A humanized antibody that binds to the interleukin 2 receptor" *Proc. Natl. Acad. Sci. USA* 86(24):10029–10033 (Dec. 1989).

Queen et al., "Construction of Humanized Antibodies and Testing in Primates" *J. Cell. Biochem. Suppl. 15 (Part E)* (20th Ann. Mtg. Keystone Symp. Denver, CO Mar. 10–16, 1991) pps. 137 (1991).

Queen et al., "Humanised antibodies to the IL–2 receptor" *Protein Eng. Antibody Mol. Prophyl. Ther. Appl. Man*, Clark, M., Nottingham, UK:Academic Titles pps. 159–170 (1993).

Rhodes & Birch, "Large–Scale Production of Proteins from Mammalian Cells" *Bio/Technology* 6:518, 521, 523 (May 1988).

Riechmann & Winter, "Recombinant Antibodies" (U. of London Royal Postgraduate Medical School, Wolfson Institute, Abstract) (May 1987).

Riechmann et al, "Expression of an Antibody Fv Fragment in Myeloma Cells" *J. Mol. Biol.* 203:825–828 (1988).

Riechmann et al., "Reshaping Human Antibodies for Therapy" *Nature* 332:323–327 (Mar. 24, 1988).

Riechmann, "Declaration" *from EP Opposition to EP Patent No. 451,261 B1* (Oct. 22, 1996).

Riechmann, "Humanizing of Recombinant Antibodies" (Intl. Symp. on Clin. Appl. of Monoclonal Antibodies, Guildford, England) pps. 33–34 (Sep. 1987).

Roberts & Rees, "Generation of an antibody with enhanced affinity and specificity for its antigen by protein engineering" *Nature* 328:731–734 (Aug. 1987).

Rodrigues et al., "Engineering a humanized bispecific F(ab')₂ fragment for improved binding to T cells" *Int. J. Cancer* (Suppl.) 7:45–50 (1992).

Roitt et al. *Immunology* (Gower Medical Publishing Ltd., London, England) pps. 5.5 (1985).

Rostapshov et al., "Effective method for obtaining long nucleotide chains on partially complementary templates" *FEBS Letters* 249(2):379–382 (Jun. 1989).

Routledge et al., "A Humanized Monovalent CD3 Antibody which Can Activate Homologous Complement" *European Journal of Immunology* 21:2717–2725 (1991).

Saul et al., "Preliminary refinement and structural analysis of the Fab fragment from human immunoglobulin new at 2.0 A resolution" *Journal of Biological Chemistry* 253(2):585–597 (Jan. 25, 1978).

Schneider et al., "The Anti–Idiotypic Response by Cynomolgus Monkeys to Humanized Anti–Tac Is Primarily Directed to Complementarity–Determining Regions H1, H2, and L3" *J. of Immunology* 150:3086–3090 (Apr. 1993).

Schroff, R. et al., "Human anti–murine immunoglobulin responses in patients receiving monoclonal antibody therapy" *Cancer Research* 45:879–885 (1985).

Sedlacek et al., "Monoclonal Antibodies in Tumor Therapy", Karger pps. 119–126, 133–179 (1988).

Segal et al., "The three–dimensional structure of a phosphorylcholine–binding mouse immunoglobulin Fab and the nature of the antigen binding site" *Proc. Natl. Acad. Sci. USA* 71(11):4298–4302 (Nov. 1974).

Sha et al., "A Heavy–Chain Grafted Antibody that Recognizes the Tumor–Associated TAG72 Antigen" *Cancer Biotherapy* 9:341–349 (1994).

Shalaby et al., "Development of Humanized Bispecific Antibodies Reactive with Cytotoxic Lymphocytes and Tumor Cells Overexpressing the HER2 Protooncogene" *Journal of Experimental Medicine* 175:217–225 (Jan. 1, 1992).

Shearman et al., "Construction, Expression and Characterization of Humanized Antibodies Directed Against the Human α/β T Cell Receptor" *J. Immunol.* 147(12):4366–4373 (Dec. 15, 1991).

Shepard and Lewis, "Resistance of tumor cells to tumor necrosis factor" *J. Clin. Immunol.* 8(5):333–395 (1988).

Sheriff et al., "Three–dimensional structure of an antibody-antigen complex" *Proc. Natl. Acad. Sci. USA* 84(22):8075–8079 (Nov. 1987).

Sherman et al., "Haloperidol binding to monoclonal antibodies" *Journal of Biological Chemistry* 263:4064–4074 (1988).

Shields et al., "Inhibition of Allergic Reactions with Antibodies to IgE" *International Archives of Allergy and Immunology* 107(1–3):308–312 (May 1995).

Silverton et al., "Three–dimensional structure of an intact human immunoglobulin" *Proc. Natl. Acad. Sci. USA* 74:5140–5144 (1977).

Sims et al., "A Humanized CD18 Antibody Can Block Function Without Cell Destruction" *The Journal of Immunology* 151(4):2296–2308 (Aug. 1993).

Slamon et al., "Human Breast Cancer: Correlation of Relapse and Survival with Amplification of the HER–2/neu Oncogene" *Science* 235:177–182 (Jan. 9, 1987).

Slamon et al., "Studies of the HER–2/neu Proto–oncogene in Human Breast and Ovarian Cancer" *Science* 244:707–712 (May 12, 1989).

Smith–Gill et al., "A Three–dimensional Model of an Anti–lysozyme Antibody" *Mol. Biol.* 194:713–724 (1987).

Snow and Amzel, "Calculating three–dimensional changes in protein structure due to amino–acid substitutions: the variable region of immunoglobulins" *Protein: Structure, Function, and Genetics*, Alan R. Liss, Inc. vol. 1:267–279 (1986).

Songsivilai et al., "Bispecific antibody: a tool for diagnosis and treatment of disease" *Clin. Exp. Immunol.* 79:315–321 (1990).

Sox et al., "Attachment of carbohydrate to the variable region of myeloma immunoglobulin light chains" *Proc. Natl. Acad. Sci. USA* 66:975–82 (Jul. 1970).

Spiegelberg et al., "Localization of the carbohydrate within the variable region of light and heavy chains of human γG myeloma proteins" *Biochemistry* 9:4217–23 (Oct. 1970).

Stanford, "A Predictive Method for Determining Possible Three–dimensional Foldings of Immunoglobulin Backbones Around Antibody Combining Sites" *Theor. Biol.* 88:421–439 (1981).

Stickney et al., "Bifunctional Antibody: ZCE/CHA $^{111}$Indium BLEDTA–IV Clinical Imaging in Colorectal Carcinoma" *Antibody, Immuno Radiopharm* 2:1–13 (1989).

Takeda et al., "Construction of Chimaeric Processed Immunoglobulin Genes Containing Mouse Variable and Human Constant Region Sequences" *Nature* 314(6010):452–454 (Apr. 4, 1985).

Tao et al., "Studies of aglycosylated chimeric mouse–human IgG. Role of Carbohydrate in the Structure and Effector Functions Mediated by the Human IgG Constant Region" *Journal of Immunology* 143(8):2595–2601 (Oct. 15, 1989).

Tempest et al., "Identification of framework residues required to restore antigen binding during reshaping of a monoclonal antibody against the glycoprotein gB of human cytomegalovirus" *Int. J. Biol. Macromol.* 17:37–42 (1995).

Tempest et al., "Reshaping a Human Monoclonal Antibody to Inhibit Human Respiratory Syncytial Virus Infection In Vivo" *Bio/Technology* 9:266–271 (Mar. 1991).

Tighe et al., "Delayed Allograft Rejection in Primates Treated with Anti–IL–2 Receptor Monoclonal antibody Campath–6" *Transplantation* 45(1):226–228 (Jan. 1988).

Tramontano et al., "Framework residue 71 is a major determinant of the position and conformation of the second hypervariable region in the $V_H$ domains of immunoglobulins" *J. Mol. Biol.* 215(1):175–182 (Sep. 5, 1990).

Tramontano, "Structural Determinants of the Conformations of Medium–Sized Loops in Proteins" *Proteins* 6:382–394 (1989).

Uchiyama et al., "A Monoclonal Antibody (ANTI–Tac) Reactive with Activated and Functionally Mature Human T Cells" *Journal of Immunology* 126:1393–1397 (1981).

Verhoeyen & Riechmann, "Engineering of Antibodies" *BioEssays* 8(2):74–78 (Feb./Mar. 1988).

Verhoeyen et al., "Grafting Hypervariable Regions in Antibodies" *Protein Structure, Folding, and Design 2* (Proc. DuPont–UCLA Symp. Streamboat Springs, CO, Apr. 4–11, 1987), Dale L. Oxender, New York:Alan R. Liss, Inc. pps. 501–502 (1987).

Verhoeyen et al., "Re–shaped human anti–PLAP antibodies" *Monoclonal Antibodies Applications in clinical oncology*, Epenetos, 1st edition, Chapman & Hall Medical pps. 37–43 (1991).

Verhoeyen et al., "Reshaping Human Antibodies: Grafting an Antilysozyme Activity" *Science* 239:1534–1536 (Mar. 25, 1988).

Vincenti et al., "Interleukin–2–Receptor Blockade with Daclizumab to Prevent Acute Rejection in Renal Transplantation" *New Engl. J. Med.* 338:161–165 (1998).

Vitetta et al., "Redesigning Nature's Poisons to Create Anti–Tumor Reagents" *Science* 238:1098–1104 (1987).

Waldmann et al., "Interleukin 2 Receptor (Tac Antigen) Expression in HTLV–1–associated Adult T–Cell Leukemia" *Cancer Research* 45:4559s–4562s (1985).

Waldmann, T., "Monoclonal Antibodies in Diagnosis and Therapy" *Science* 252:1657–1662 (Jun. 1991).

Waldmann, Thomas A., "The Structure, Function, and Expression of Interleukin–2 Receptors on Normal and Malignant Lymphocytes" *Science* 232:727–732 (1986).

Wallick et al., "Glycosylation of a VH residue of a monoclonal antibody against alpha (1——6) dextran increases its affinity for antigen" *Journal of Experimental Medicine* 168(3):1099–1109 (Sep. 1988).

Ward et al., "Expression and Secretion of Repertoires of VH Domains in *Escherichia coli*: Isolation of Antigen Binding Activities" *Progress in Immunology* (7th Intl. Congress Immunol. Berlin, W. Germany), F. Melchers vol. VII:1144–1151 (1989).

Ward, E.S. et al., "Binding activities of a repertoire of single immunoglobulin variable domains secreted from *Escherichia coli*" *Nature* 341:544–546 (1989).

Werther et al., "Humanization of an Anti–Lymphocyte Function–Associated Antigen (LFA)–1 Monoclonal Antibody and Reengineering of the Humanized Antibody for Binding to Rhesus LFA–1" *J. of Immunology* 157:4986–4995 (1996).

Whittle et al., "Construction and Expression of A CDR–Grafted Anti–TNF Antibody" *J. Cell Biochem. Suppl. 0* (Symp. on Protein and Pharm. Eng. Mol. and Cell. Biol. Park City, Utah)13 Part A:96 (1989).

Winter & Neuberger, "Restructuring Enzymes and Antibodies" *Investigation and Exploitation of Antibody Combining Sites*, Eric Reid, Plenum Press pps. 139–140 (1985).

Winter and Milstein, "Man–made antibodies" *Nature* 349(6307):293–299 (Jan. 24, 1991).

Winter et al., "Protein Engineering by Site Directed Mutagenesis" *Chemical Synthesis in Molecular Biology*, H. Blocker et al., VCH pps. 189–197 (1987).

Winter G., "Antibody Engineering" *Phil. Trans. R. Soc. Lond. B* 324:99–109 (1989).

Woodle et al., "Humanized OKT3 Antibodies: Successful Transfer of Immune Modulating Properties and Idiotype Expression" *J. of Immunology* 148(9):2756–2763 (May 1992).

Wu et al., "An Analysis of the Sequences of the Variable Regions of Bence Jones Proteins and Myeloma Light Chains and Their Implications for Antibody Complementarity" *Journal of Experimental Medicine* 132:211–250 (1970).

Yamamoto et al., "Similarity of protein encoded by the human c–erb–B–2 gene to epidermal growth factor receptor" *Nature* 319:230–234 (1986).

Carter et al., "Improved Oligonucleotide Site–Directed Mutagenesis Using M13 Vectors" *Nucl. Acids Res.* 13(12):4431–4443 (Jun. 25, 1986).

Carteron et al., "Treatment of Murine Lupus with F(ab')2 Fragments of Monoclonal Antibody to L3T4 (Suppression of Autoimmunity Does Not Depend on T Helper Cell Depletion)" *J Immunol* 142(5):1470–1475 (Mar. 1, 1999).

Choy et al., "Effect of a humanised non–depleting anti–CD4 monoclonal antibody (mAb) on synovial fluid (SF) in rheumatoid arthritis (RA)" *Arthritis and Rheumatism* (abstract No. 130)abstract supplement (1997).

Choy et al., "T cell hypothesis in rheumatoid arthritis (RA) tested by humanised non–depleting anti–CD4 monoclonal antibody (mAb) treatment II: clinical activity is related to pharmacodynamic effects" *Immunology* (abstract No. OGg378) 89(Suppl. 1) (1996).

Choy et al., "T cell hypothesis in rheumatoid arthritis (RA) tested by humanised non–depleting anti–CD4 monoclonal antibody (mAb) treatment II: clinical activity is related to pharmacodynamic effects" *Arthritis and Rheumatism* (abstract No. 1301) abstract supplement (1996).

Co et al., "Genetically engineered deglycosylation of the variable domain increases the affinity of an anti–CD33 monoclonal antibody" *Molecular Immunology* 30(15):1361–1367 (Oct. 1993).

Connolly et al., "T cell hypothesis in rheumatoid arthritis (RA) tested by humanized non–depleting anti–CD4 monoclonal antibody (mAb) treatment III: immunological effects" *Arthritis and Rheumatism* (abstract No. 1302) abstract supplement (1996).

Cunningham et al., "Receptor and Antibody Epitopes in Human Growth Hormone Identified by Homolog–Scanning Mutagenesis" *Science* 243:1330–1336 (1989).

Drebin et al., "Monoclonal Antibodies Specific for the neu Oncogene Product Directly Mediate Anti–tumor Effects In Vivo" *Oncogene* 2(4):387–394 (1988).

Emery et al., "Humanised monoclonal antibodies for therapeutic applications" *Exp. Opin. Invest. Drugs* 3(3):241–251 (1994).

Fan et al., "Comparison of the three–dimensional structures of a humanized and a chimeric Fab of an anti–γ–interferon antibody" *Journal of Molecular Recognition* 12(1):19–32 (Jan.–Feb. 1999).

Garrido et al., "Refocusing the Immune system to React with Human Tumors by Targeting Human LHuman Lymphocytes With Bispecific Antibodies" *Devel. Biol. Standard* 71:33–42 (1990).

Gillies et al., "Antigen Binding and Biological Activities of Engineered Mutant Chimeric Antibodies with Human Tumor Specificities" *Hum. Antibod. Hybridomas* 1(1):47–54 (1990).

Gorman et al., "Humanisation of monoclonal antibodies for therapy" *Immunology* 2:457–466 (1990).

Heinrich et al., "Characterization of a human T cell–specific chimeric antibody (CD7) with human constant and mouse variable regions" *Journal of Immunology* 143(11):3589–3597 (Dec. 1, 1989).

Kelley et al., "Antigen Binding Thermodynamics and Antiproliferative Effects of Chimeric and Humanized anti–p185$^{HER2}$ Antibody Fab Fragments" *Biochemistry* 31:5434–5441 (1992).

Kreitman et al., "Mik–β(Fv)–PE40, a recombinant immunotoxin cytotoxic toward cells bearing the β–chain of the IL–2 receptor" *Journal of Immunology* 149(8):2810–2815 (Oct. 15, 1992).

Kuijpers et al., "Analysis of the Role of Leukocyte Function–Associated Antigen–1 in Activation of Human Influenza Virus–Specific T Cell Clones" *J. of Immunology* 144(9):3281–3287 (May 1, 1990).

Leung et al., "Engineering a unique glycosylation site for site–specific conjugation of haptens to antibody fragments" *Journal of Immunology* 154:5919–5926 (1995).

Mathieson et al., "Monoclonal–antibody therapy in systemic vasculitis" *New England J. of Medicine* 323(4):250–254 (Jul. 26, 1990).

Osborne, Randall, "Full Approval of Breast Cancer Drug Expected by Year's End, FDA Panel OKs Genentech's Herceptin" *Daily Ink* pps. 1–2 (Sep. 4, 1998).

Panayi et al., "T cell hypothesis in rheumatoid arthritis (RA) tested by humanised non–depleting anti–CD4 monoclonal antibody (mAb) treatment I: suppression of disease activity and acute phase response" *Immunology* (abstract OGg379) 89(suppl. 1) (1996).

Panayi et al., "T cell hypothesis in rheumatoid arthritis (RA) tested by humanized non–depleting anti–CD4 monoclonal antibody (mAb) treatment I: suppression of disease activity and acute phase response" *Arthritis and Rheumatism* (abstract No. 1300) abstract supplement (1996).

Pegram et al., "Antibody dependent cell–mediated cytotoxicity in breast cancer patients in Phase III clinical trials of a humanized anti–HER2 antibody" *Proceedings of the American Association for Cancer Research* (Abstract No. 4044) 38:602 (Mar. 1997).

Rudikoff et al., "Single amino acid substitution altering antigen–binding specificity" *Proc. Natl. Acad. Sci. USA* 79:1979–1983 (1982).

Sambrook et al., "Oligonucleotide–mediated Mutagenesis" *Molecular Cloning A Laboratory Manual*, Second edition, Cold Spring Harbor, NY:Cold Spring Harbor Laboratory Press pps. 15.51–15.56 (1989).

Schanfield and Van Loghem, "Human immunoglobulin allotypes" *Handbook of Experimental Immunology*, Weir and Herzenberg, eds., Blackwell Scientific Publishers, Chapter 94, pps. 94.1–94.18 (1986).

Tanimoto et al., "Restricted expression of an early myeloid and monocytic cell surface antigen defined by monoclonal antibody M195" *Leukemia* 3(5):339–348 (May 1989).

Tsudo et al., "Characterization of the interleukin 2 receptor β chain using three distinct monoclonal antibodies" *Proc. Natl. Acad. Sci. USA* 86(6):1982–1986 (Mar. 1989).

"ZENAPAX (Daclizumab) Sterile Concentrate for Injection" *Physicians' Desk Reference* (*website version*) (product information) pps. 1–8 (2001).

* cited by examiner

FIG. 1A

```
                  10              20              30              40              50
4D5       DIVMTQSHKFMSTSVGDRVSITCKASQDVNTAVAWYQQKPGHSPKLLIYSASFRYT
HU4D5     DIQMTQSPSSLSASVGDRVTITCRASQDVNTAVAWYQQKPGKAPKLLIYSASFLES
HUV_L κI  DIQMTQSPSSLSASVGDRVTITCRASQDVSSYLAWYQQKPGKAPKLLIYAASSLES
                                  V_L-CDR1                    V_L-CDR2

60              70              80              90             100
4D5       GVPDRFTGNRSGTDFTFTISSVQAEDLAVYYCQQHYTTPPTFGGGTKLEIKRA
HU4D5     GVPSRFSGSRSGTDFTLTISSLQPEDFATYYCQQHYTTPPTFGQGTKVEIKRT
HUV_L κI  GVPSRFSGSGSGTDFTLTISSLQPEDFATYYCQQYNSLPYTFGQGTKVEIKRT
                                                V_L-CDR3
```

FIG. 1B

```
                    10              20              30              40              50     A
4D5         EVQLQQSGPELVKPGASLKLSCTASGFNIKDTYIHWVKQRPEQGLEWIGRIYPTN
HU4D5       EVQLVESGGGLVQPGGSLRLSCAASGFNIKDTYIHWVRQAPGKGLEWVARIYPTN
HUVHIII     EVQLVESGGGLVQPGGSLRLSCAASGFTFSDYAMSWVRQAPGKGLEWVAVISENG
                                          -------                    -------
                                          VH-CDR1                    VH-CDR2

60              70              80 ABC         90          100ABC
4D5         GYTRYDPKFQDKATITADTSSNTAYLQVSRLTSEDTAVYYCSRWGGDGFYAMDYW
HU4D5       GYTRYADSVKGRFTISADTSKNTAYLQMNSLRAEDTAVYYCSRWGGDGFYAMDVW
HUVHIII     SDTYYADSVKGRFTISRDDSKNTLYLQMNSLRAEDTAVYYCARDRGGAVSYFDVW
            --                                                  ------------
                                                                VH-CDR3

110
4D5         GQGASVTVSS
HU4D5       GQGTLVTVSS
HUVHIII     GQGTLVTVSS
```

```
V_L                   10         20        30          40
muxCD3     DIQMTQTTSSLSASLGDRVTISCRASQDIRNYLNWYQQKP
             **       *      *              *
huxCD3v1   DIQMTQSPSSLSASVGDRVTITCRASQDIRNYLNWYQQKP
                                   # #     #
huκI       DIQMTQSPSSLSASVGDRVTITCRASQSISNYLAWYQQKP6
                                  ^^^^^^^
                                   CDR-L1^^

50         60        70        80
muxCD3     DGTVKLLIYYTSRLHSGVPSKFSGSGSGTDYSLTISNLEQ
           ****       *       *         *    * **
huxCD3v1   GKAPKLLIYYTSRLESGVPSRFSGSGSGTDYTLTISSLQP
                    ## #                      #
huκI       GKAPKLLIYAASSLESGVPSRFSGSGSGTDFTLTISSLQP
                   ^^^
                   CDR-L2

90        100
muxCD3     EDIATYFCQQGNTLPWTFAGGTKLEIK
             *   *              **   *
huxCD3v1   EDFATYYCQQGNTLPWTFGQGTKVEIK
                    # #
huκI       EDFATYYCQQYNSLPWTFGQGTKVEIK
                   ^^^^^^^
                   CDR-L3^

V_H                   10         20        30          40
muxCD3     EVQLQQSGPELVKPGASMKISCKASGYSFTGYTMNWVKQS
              **   **  *  *  ***  *                * *
huxCD3v1   EVQLVESGGGLVQPGGSLRLSCAASGYSFTGYTMNWVRQA
                                    ## ## #
huIII      EVQLVESGGGLVQPGGSLRLSCAASGFTFSSYAMSWVRQA
                                        ^^^^^^
                                         CDR-H1

50         60        70
muxCD3     HGKNLEWMGLINPYKGVSTYNQKFKDKATLTVDKSSSTAY
             *    **   ****  *   ** **         **
huxCD3v1   PGKGLEWVALINPYKGVTTYADSVKGRFTISVDKSKNTAY
                    ## ####  #                # #
huIII      PGKGLEWVSVISGDGGSTYYADSVKGRFTISRDNSKNTLY
                   ^^^^^^^
                   CDR-H2

80  abc    90      100abcde      110
muxCD3     MELLSLTSEDSAVYYCARSGYYGDSDWYFDVWGAGTTVTVSS
           ****   **   *                         *  *
huxCD3v1   LQMNSLRAEDTAVYYCARSGYYGDSDWYFDVWGQGTLVTVSS
                           ########### #
huIII      LQMNSLRAEDTAVYYCARGRVGYSLSGLYDYWGQGTLVTVSS
                             D E T    S
                           ^^^^^^^^^^^^
                             CDR-H3
```

```
H52H4-160                                    QVQLQQSGPELVKPGASVKISCKTSGYTFTE
pH52-8.0                       .***.** **.**.*...** *********
              MGWSCIILFLVATATGVHSEVQLVESGGGLVQPGGSLRLSCATSGYTFTE
                       10        20        30        40        50

H52H4-160     YTMHWMKQSHGKSLEWIGGFNPKNGGSSHNQRFMDKATLAVDKSTSTAYM
              ******.*. **.***..*.*.*******.**********. *..**********
pH52-8.0      YTMHWMRQAPGKGLEWVAGINPKNGGTSHNQRFMDRFTISVDKSTSTAYM
                       60        70        80        90       100

H52H4-160     ELRSLTSEDSGIYYCARWRGLNYGFDVRYFDVWGAGTTVTVSSASTKGPS
              .. .**...* .***************************** ** **********
pH52-8.0      QMNSLRAEDTAVYYCARWRGLNYGFDVRYFDVWGQGTLVTVSSASTKGPS
                      110       120       130       140       150

H52H4-160     VFPLAPSSKSTSGGTAALGCLVKDYFPEPVTVSWNSGALTSGVHTFPAVL
              ****** *.*** .****************************************
pH52-8.0      VFPLAPCSRSTSESTAALGCLVKDYFPEPVTVSWNSGALTSGVHTFPAVL
                      160       170       180       190       200

H52H4-160     QSSGLYSLSSVVTVPSSSLGTQTYICNVNHKPSNTKVDKKVEPKSCDKTH
              ********************** ***.************** ** * *
pH52-8.0      QSSGLYSLSSVVTVTVTSSNFGTQTYTCNVDHKPSNTKVDKTVERKCC---V
                      210       220       230       240

H52H4-160     TCPPCPAPELLGGPSVFLFPPKPKDTLMISRTPEVTCVVVDVSHEDPEVK
              ******* ..*****************************************.
pH52-8.0      ECPPCPAPP-VAGPSVFLFPPKPKDTLMISRTPEVTCVVVDVSHEDPEVQ
                      250  260        270       280       290
```

FIG. 6A-2

```
                        290        300        310        320        330
H52H4-160    FNWYVDGVEVHNAKTKPREEQYNSTYRVVSVLTVLHQDWLNGKEYKCKVS
             ******.*********.***.***.********************
pH52-8.0     FNWYVDGMEVHNAKTKPREEQFNSTFRVVSVLTVVHQDWLNGKEYKCKVS
                        300        310        320        330        340

340        350        360        370        380
H52H4-160    NKALPAPIEKTISKAKGQPREPQVYTLPPSREEMTKNQVSLTCLVKGFYP
             **.***********.*************************
pH52-8.0     NKGLPAPIEKTISKTKGQPREPQVYTLPPSREEMTKNQVSLTCLVKGFYP
                        350        360        370        380        390

390        400        410        420        430
H52H4-160    SDIAVEWESNGQPENNYKTTPPVLDSDGSFFLYSKLTVDKSRWQQGNVFS
             ***********************.*************************
pH52-8.0     SDIAVEWESNGQPENNYKTTPPMLDSDGSFFLYSKLTVDKSRWQQGNVFS
                        400        410        420        430        440

440        450
H52H4-160    CSVMHEALHNHYTQKSLSLSPGK
             ***********************
pH52-8.0     CSVMHEALHNHYTQKSLSLSPGK
                        450        460
```

FIG. 6B

```
H52L6-158                                                    DVQMTQTSSLSASLGDRVTINCRASQDINN
                                                                      *.****. ******.******.*********
pH52-9.0   MGWSCIILFLVATATGVHSDIQMTQSPSSLSASVGDRVTITCRASQDINN
                    10        20        30        40        50

H52L6-158  YLNWYQQKPNGTVKLLIYYTSTLHSGVPSRFSGSGSGTDYSLTISNLDQE
                    10        20        30        40        50
           ********.  **********************.*****.*.  *
pH52-9.0   YLNWYQQKPGKAPKLLIYYTSTLHSGVPSRFSGSGSGTDYLTISSLQPE
                    60        70        80        90       100

H52L6-158  DIATYFCQQGNTLPPTFGGGTKVEIKRTVAAPSVFIFPPSDEQLKSGTAS
                    60        70        80        90       100
           *.****.*****************************************
pH52-9.0   DFATYYCQQGNTLPPTFGQGTKVEIKRTVAAPSVFIFPPSDEQLKSGTAS
                   110       120       130       140       150

H52L6-158  VVCLLNNFYPREAKVQWKVDNALQSGNSQESVTEQDSKDSTYSLSSTLTL
                   110       120       130       140       150
           **************************************************
pH52-9.0   VVCLLNNFYPREAKVQWKVDNALQSGNSQESVTEQDSKDSTYSLSSTLTL
                   160       170       180       190       200

H52L6-158  SKADYEKHKVYACEVTHQGLSSPVTKSFNRGEC
                   160       170       180
           ********************************
pH52-9.0   SKADYEKHKVYACEVTHQGLSSPVTKSFNRGEC
                   210       220       230
```

METHOD FOR MAKING HUMANIZED ANTIBODIES

This is a divisional of U.S. Ser. No. 08/146,206 filed Nov. 17, 1993, now U.S. Pat. No. 6,407,213 issued Jun. 18, 2002, which is a 371 of PCT/US92/05126 filed Jun. 15, 1992, which is a CIP of 07/715,272 filed Jun. 14, 1991 (abandoned), the disclosures of which are incorporated herein by reference.

FIELD OF THE INVENTION

This invention relates to methods for the preparation and use of variant antibodies and finds application particularly in the fields of immunology and cancer diagnosis and therapy.

BACKGROUND OF THE INVENTION

Naturally occurring antibodies (immunoglobulins) comprise two heavy chains linked together by disulfide bonds and two light chains, one light chain being linked to each of the heavy chains by disulfide bonds. Each heavy chain has at one end a variable domain ($V_H$) followed by a number of constant domains. Each light chain has a variable domain ($V_L$) at one end and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains, see e.g. Chothia et al., *J. Mol. Biol.* 186:651–663 (1985); Novotny and Haber, *Proc. Natl. Acad. Sci. USA* 82:4592–4596 (1985).

The constant domains are not involved directly in binding the antibody to an antigen, but are involved in various effector functions, such as participation of the antibody in antibody-dependent cellular cytotoxicity. The variable domains of each pair of light and heavy chains are involved directly in binding the antibody to the antigen. The domains of natural light and heavy chains have the same general structure, and each domain comprises four framework (FR) regions, whose sequences are somewhat conserved, connected by three hyper-variable or complementarity determining regions (CDRs) (see Kabat, E. A. et al., *Sequences of Proteins of Immunological Interest*, National Institutes of Health, Bethesda, Md., (1987)). The four framework regions largely adopt a β-sheet conformation and the CDRs form loops connecting, and in some cases forming part of, the β-sheet structure. The CDRs in each chain are held in close proximity by the framework regions and, with the CDRs from the other chain, contribute to the formation of the antigen binding site.

Widespread use has been made of monoclonal antibodies, particularly those derived from rodents including mice, however they are frequently antigenic in human clinical use. For example, a major limitation in the clinical use of rodent monoclonal antibodies is an anti-globulin response during therapy (Miller, R. A. et al., *Blood* 62:988–995 (1983); Schroff, R. W. et al., *Cancer Res.* 45:879–885 (1985)).

The art has attempted to overcome this problem by constructing "chimeric" antibodies in which an animal antigen-binding variable domain is coupled to a human constant domain (Cabilly et al., U.S. Pat. No. 4,816,567; Morrison, S. L. et al., *Proc. Natl. Acad. Sci. USA* 81:6851–6855 (1984); Boulianne, G. L. et al., *Nature* 312:643–646 (1984); Neuberger, M. S. et al., *Nature* 314:268–270 (1985)). The term "chimeric" antibody is used herein to describe a polypeptide comprising at least the antigen binding portion of an antibody molecule linked to at least part of another protein (typically an immunoglobulin constant domain).

The isotype of the human constant domain may be selected to tailor the chimeric antibody for participation in antibody-dependent cellular cytotoxicity (ADCC) and complement-dependent cytotoxicity (see e.g. Brüggemann, M. et al., *J. Exp. Med.* 166:1351–1361 (1987); Riechmann, L. et al., *Nature* 332:323–327 (1988); Love et al., *Methods in Enzymology* 178:515–527 (1989); Bindon et al., *J. Exp. Med.* 168:127–142 (1988).

In the typical embodiment, such chimeric antibodies contain about one third rodent (or other non-human species) sequence and thus are capable of eliciting a significant anti-globulin response in humans. For example, in the case of the murine anti-CD3 antibody, OKT3, much of the resulting anti-globulin response is directed against the variable region rather than the constant region (Jaffers, G. J. et al., *Transplantation* 41:572–578 (1986)).

In a further effort to resolve the antigen binding functions of antibodies and to minimize the use of heterologous sequences in human antibodies, Winter and colleagues (Jones, P. T. et al., *Nature* 321:522–525 (1986); Riechmann, L. et al., *Nature* 332:323–327 (1988);

Verhoeyen, M. et al., *Science* 239:1534–1536 (1988)) have substituted rodent CDRs or CDR sequences for the corresponding segments of a human antibody. As used herein, the term "humanized" antibody is an embodiment of chimeric antibodies wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The therapeutic promise of this approach is supported by the clinical efficacy of a humanized antibody specific for the CAMPATH-1 antigen with two non-Hodgkin lymphoma patients, one of whom had previously developed an anti-globulin response to the parental rat antibody (Riechmann, L. et al., *Nature* 332:323–327 (1988); Hale, G. et al., *Lancet* i:1394–1399 (1988)). A murine antibody to the interleukin 2 receptor has also recently been humanized (Queen, C. et al., *Proc. Natl. Acad. Sci. USA* 86:10029–10033 (1989)) as a potential immunosuppressive reagent. Additional references related to humanization of antibodies include Co et al., *Proc. Natl. Acad. Sci. USA* 88:2869–2873 (1991); Gorman et al., *Proc. Natl. Acad. Sci. USA* 88:4181–4185 (1991); Daugherty et al., *Nucleic Acids Research* 19(9):2471–2476 (1991); Brown et al., *Proc. Natl. Acad. Sci. USA* 88:2663–2667 (1991); Junghans et al., *Cancer Research* 50:1495–1502 (1990).

In some cases, substituting CDRs from rodent antibodies for the human CDRs in human frameworks is sufficient to transfer high antigen binding affinity (Jones, P. T. et al., *Nature* 321:522–525 (1986); Verhoeyen, M. et al., *Science* 239:1534–1536 (1988)), whereas in other cases it has been necessary to additionally replace one (Riechmann, L. et al., *Nature* 332:323–327 (1988)) or several (Queen, C. et al., *Proc. Natl. Acad. Sci. USA* 86:10029–10033 (1989)) framework region (FR) residues. See also Co et al., supra.

For a given antibody a small number of FR residues are anticipated to be important for antigen binding. Firstly for example, certain antibodies have been shown to contain a few FR residues which directly contact antigen in crystal structures of antibody-antigen complexes (e.g., reviewed in Davies, D. R. et al., *Ann. Rev. Biochem.* 59:439–473 (1990)). Secondly, a number of FR residues have been proposed by Chothia, Lesk and colleagues (Chothia, C. & Lesk, A. M., *J. Mol. Biol.* 196:901–917 (1987); Chothia, C. et al., *Nature* 342:877–883 (1989); Tramontano, A. et al., *J. Mol. Biol.* 215:175–182 (1990)) as critically affecting the conformation of particular CDRs and thus their contribution to antigen binding. See also Margolies et al., *Proc. Natl. Acad. Sci. USA* 72:2180–2184 (1975).

It is also known that, in a few instances, an antibody variable domain (either $V_H$ or $V_L$) may contain glycosylation sites, and that this glycosylation may improve or abolish antigen binding, Pluckthun, *Biotechnology* 9:545–51 (1991); Spiegelberg et al., *Biochemistry* 9:4217–4223 (1970); Wallic et al., *J. Exp. Med.* 168:1099–1109 (1988); Sox et al., *Proc. Natl. Acad. Sci. USA* 66:975–982 (1970); Margni et al., *Ann. Rev. Immunol.* 6:535–554 (1988). Ordinarily, however, glycosylation has no influence on the antigen-binding properties of an antibody, Pluckthun, supra, (1991).

The three-dimensional structure of immunoglobulin chains has been studied, and crystal structures for intact immunoglobulins, for a variety of immunoglobulin fragments, and for antibody-antigen complexes have been published (see e.g., Saul et al., *Journal of Biological Chemistry* 25:585–97 (1978); Sheriff et al., *Proc. Natl. Acad. Sci. USA* 84:8075–79 (1987); Segal et al., *Proc. Natl. Acad. Sci. USA* 71:4298–4302 (1974); Epp et al., *Biochemistry* 14(22) :4943–4952 (1975); Marquart et al., *J. Mol. Biol.* 141:369–391 (1980); Furey et al., *J. Mol. Biol.* 167:661–692 (1983); Snow and Amzel, *Protein: Structure, Function, and Genetics* 1:267–279, Alan R. Liss, Inc. pubs. (1986); Chothia and Lesk, *J. Mol. Biol.* 196:901–917 (1987); Chothia et al., *Nature* 342:877–883 (1989); Chothia et al., *Science* 233:755–58 (1986); Huber et al., *Nature* 264:415–420 (1976); Bruccoleri et al., *Nature* 335:564–568 (1988) and *Nature* 336:266 (1988); Sherman et al., *Journal of Biological Chemistry* 263:4064–4074 (1988); Amzel and Poljak, *Ann. Rev. Biochem.* 48:961–67 (1979); Silverton et al., *Proc. Natl. Acad. Sci. USA* 74:5140–5144 (1977); and Gregory et al., *Molecular Immunology* 24:821–829 (1987). It is known that the function of an antibody is dependent on its three dimensional structure, and that amino acid substitutions can change the three-dimensional structure of an antibody, Snow and Amzel, supra. It has previously been shown that the antigen binding affinity of a humanized antibody can be increased by mutagenesis based upon molecular modelling (Riechmann, L. et al., *Nature* 332:323–327 (1988); Queen, C. et al., *Proc. Natl. Acad. Sci. USA* 86:10029–10033 (1989)).

Humanizing an antibody with retention of high affinity for antigen and other desired biological activities is at present difficult to achieve using currently available procedures. Methods are needed for rationalizing the selection of sites for substitution in preparing such antibodies and thereby increasing the efficiency of antibody humanization.

The proto-oncogene HER2 (human epidermal growth factor receptor 2) encodes a protein tyrosine kinase ($p185^{HER2}$) that is related to and somewhat homologous to the human epidermal growth factor receptor (see Coussens, L. et al., *Science* 230:1132–1139 (1985); Yamamoto, T. et al., *Nature* 319:230–234 (1986); King, C. R. et al., *Science* 229:974–976 (1985)). HER2 is also known in the field as c-erbB-2, and sometimes by the name of the rat homolog, neu. Amplification and/or overexpression of HER2 is associated with multiple human malignancies and appears to be integrally involved in progression of 25–30% of human breast and ovarian cancers (Slamon, D. J. et al., *Science* 235:177–182 (1987), Slamon, D. J. et al., *Science* 244:707–712 (1989)). Furthermore, the extent of amplification is inversely correlated with the observed median patient survival time (Slamon, supra, Science 1989).

The murine monoclonal antibody known as muMAb4D5 (Fendly, B. M. et al., *Cancer Res.* 50:1550–1558 (1990)), directed against the extracellular domain (ECD) of $p185^{HER2}$, specifically inhibits the growth of tumor cell lines overexpressing $p185^{HER2}$ in monolayer culture or in soft agar (Hudziak, R. M. et al., *Molec. Cell. Biol.* 9:1165–1172 (1989); Lupu, R. et al., *Science* 249:1552–1555 (1990)). MuMAb4D5 also has the potential of enhancing tumor cell sensitivity to tumor necrosis factor, an important effector molecule in macrophage-mediated tumor cell cytotoxicity (Hudziak, supra, 1989; Shepard, H. M. and Lewis, G. D. *J. Clinical Immunology* 8:333–395 (1988)). Thus muMAb4D5 has potential for clinical intervention in and imaging of carcinomas in which $p185^{HER2}$ is overexpressed. The muMAb4D5 and its uses are described in PCT application WO 89/06692 published Jul. 27, 1989. This murine antibody was deposited with the ATCC and designated ATCC CRL 10463. However, this antibody may be immunogenic in humans.

It is therefore an object of this invention to provide methods for the preparation of antibodies which are less antigenic in humans than non-human antibodies but have desired antigen binding and other characteristics and activities.

It is a further object of this invention to provide methods for the efficient humanization of antibodies, i.e. selecting non-human amino acid residues for importation into a human antibody background sequence in such a fashion as to retain or improve the affinity of the non-human donor antibody for a given antigen.

It is another object of this invention to provide humanized antibodies capable of binding $p185^{HER2}$.

Other objects, features, and characteristics of the present invention will become apparent upon consideration of the following description and the appended claims.

SUMMARY OF THE INVENTION

The objects of this invention are accomplished by a method for making a humanized antibody comprising amino acid sequence of an import, non-human antibody and a human antibody, comprising the steps of:

a. obtaining the amino acid sequences of at least a portion of an import antibody variable domain and of a consensus variable domain;

b. identifying Complementarity Determining Region (CDR) amino acid sequences in the import and the human variable domain sequences;

c. substituting an import CDR amino acid sequence for the corresponding human CDR amino acid sequence;

d. aligning the amino acid sequences of a Framework Region (FR) of the import antibody and the corresponding FR of the consensus antibody;

e. identifying import antibody FR residues in the aligned FR sequences that are non-homologous to the corresponding consensus antibody residues;

f. determining if the non-homologous import amino acid residue is reasonably expected to have at least one of the following effects:

1. non-covalently binds antigen directly,
2. interacts with a CDR; or
3. participates in the $V_L$–$V_H$ interface; and g. for any non-homologous import antibody amino acid residue which is reasonably expected to have at least one of these effects, substituting that residue for the corresponding amino acid residue in the consensus antibody FR sequence.

Optionally, the method of this invention comprises the additional steps of determining if any non-homologous residues identified in step (e) are exposed on the surface of the domain or buried within it, and if the residue is exposed but has none of the effects identified in step (f), retaining the consensus residue.

Additionally, in certain embodiments the method of this invention comprises the feature wherein the corresponding consensus antibody residues identified in step (e) above are selected from the group consisting of 4L, 35L, 36L, 38L, 43L, 44L, 46L, 58L, 62L, 63L, 64L, 65L, 66L, 67L, 68L, 69L, 70L, 71L, 73L, 85L, 87L, 98L, 2H, 4H, 24H, 36H, 37H, 39H, 43H, 45H, 49H, 58H. 60H, 67H, 68H, 69H, 70H, 73H, 74H, 75H, 76H, 78H, 91H, 92H, 93H, and 103H (utilizing the numbering system set forth in Kabat, E. A. et al., *Sequences of Proteins of Immunological Interest* (National Institutes of Health, Bethesda, Md., 1987)).

In certain embodiments, the method of this invention comprises the additional steps of searching either or both of the import, non-human and the consensus variable domain sequences for glycosylation sites, determining if the glycosylation is reasonably expected to be important for the desired antigen binding and biological activity of the antibody (i.e., determining if the glycosylation site binds to antigen or changes a side chain of an amino acid residue that binds to antigen, or if the glycosylation enhances or weakens antigen binding, or is important for maintaining antibody affinity). If the import sequence bears the glycosylation site, it is preferred to substitute that site for the corresponding residues in the consensus human if the glycosylation site is reasonably expected to be important. If only the consensus sequence, and not the import, bears the glycosylation site, it is preferred to eliminate that glycosylation site or substitute therefor the corresponding amino acid residues from the import sequence.

Another embodiment of this invention comprises aligning import antibody and the consensus antibody FR sequences, identifying import antibody FR residues which are non-homologous with the aligned consensus FR sequence, and for each such non-homologous import antibody FR residue, determining if the corresponding consensus antibody residue represents a residue which is highly conserved across all species at that site, and if it is so conserved, preparing a humanized antibody which comprises the consensus antibody amino acid residue at that site.

Certain alternate embodiments of the methods of this invention comprise obtaining the amino acid sequence of at least a portion of an import, non-human antibody variable domain having a CDR and a FR, obtaining the amino acid sequence of at least a portion of a consensus antibody variable domain having a CDR and a FR, substituting the non-human CDR for the human CDR in the consensus antibody variable domain, and then substituting an amino acid residue for the consensus amino acid residue at at least one of the following sites:

a. (in the FR of the variable domain of the light chain) 4L, 35L, 36L, 38L, 43L, 44L. 58L, 46L, 62L, 63L, 64L, 65L, 66L, 67L, 68L, 69L, 70L, 71L, 73L, 85L, 87L, 98L, or b. (in the FR of the variable domain of the heavy chain) 2H, 4H, 24H, 36H, 37H, 39H, 43H, 45H, 49H, 58H, 60H, 67H, 68H, 69H, 70H, 73H, 74H, 75H, 76H, 78H, 91H, 92H, 93H, and 103H.

In preferred embodiments, the non-CDR residue substituted at the consensus FR site is the residue found at the corresponding location of the non-human antibody.

Optionally, this just-recited embodiment comprises the additional steps of following the method steps appearing at the beginning of this summary and determining whether a particular amino acid residue can reasonably be expected to have undesirable effects.

This invention also relates to a humanized antibody comprising the CDR sequence of an import, non-human antibody and the FR sequence of a human antibody, wherein an amino acid residue within the human FR sequence located at any one of the sites 4L, 35L, 36L, 38L, 43L, 44L, 46L, 58L, 62L, 63L, 64L, 65L, 66L, 67L, 68L, 69L, 70L, 71L, 73L, 85L, 87L, 98L, 2H, 4H, 24H, 36H, 37H, 39H, 43H, 45H, 49H, 58H, 60H, 67H, 68H, 69H, 70H, 73H, 74H, 75H, 76H, 78H, 91H, 92H, 93H, and 103H has been substituted by another residue. In preferred embodiments, the residue substituted at the human FR site is the residue found at the corresponding location of the non-human antibody from which the non-human CDR was obtained. In other embodiments, no human FR residue other than those set forth in this group has been substituted.

This invention also encompasses specific humanized antibody variable domains, and isolated polypeptides having homology with the following sequences.

1. SEQ. ID NO. 1, which is the light chain variable domain of a humanized version of muMAb4D5:

DIQMTQSPSSLSASVGDRVTITCRASQD-VNTAVAWYQQKPGKAPKLLIYSASFLESGVPSRFSGSRSGTDFTLTISSLQPEDFATYY-COQHYTTPPTFGQGTKVEIKRT

2. SEQ. ID NO. 2, which is the heavy chain variable domain of a humanized version of muMAb4D5:

EVQLVESGGGLVQPGGSLRLSCAASG-FNIKDTYIHWVRQAPGKGLEWVARIYPTNGYTRYADSVKGRFTISADTSKNTAYLQMNSL-RAEDTAVYYCSRWGGDGFYAMDVWGQGTLVTVSS

In another aspect, this invention provides a consensus antibody variable domain amino acid sequence for use in the preparation of humanized antibodies, methods for obtaining, using, and storing a computer representation of such a consensus sequence, and computers comprising the sequence data of such a sequence. In one embodiment, the following consensus antibody variable domain amino acid sequences are provided:

SEQ. ID NO. 3 (fight chain):

DIQMTQSPSSLSASVGDRVTITCRASQD-VSSYLAWYQQKPGKAPKLLIYAASSLESGVPSRFSGSGSGTDFTLTISSLQPEDFATYYCQQYNSLPYTFGQGTKVEIKRT, and SEQ. ID NO. 4 (heavy chain):

EVQLVESGGGLVQPGGSLRLSCAASG-FTFSDYAMSWVRQAPGK-GLEWVAVISENGSDTYYADS VKGRFTIS-RDDSKNTLYLQMNSLRAEDTAVYYCARDRGGAVSYFDVWGQGTLVTVSS

BRIEF DESCRIPTION OF THE DRAWINGS

FIG. 1A shows the comparison of the $V_L$ domain amino acid residues of muMAb4D5, huMAb4D5, and a consensus sequence (FIG. 1A, SEQ. ID NO. 5, SEQ. ID NO. 1 and SEQ. ID NO. 3, respectively). FIG. 1B shows the comparison between the $V_H$ domain amino acid residues of muMAb4D5, huMAb4D5, and a consensus sequence (FIG. 1B. SEQ. ID NO. 6, SEQ. ID NO. 2 and SEQ. ID NO. 4, respectively). Both FIGS. 1A and 1B use the generally accepted numbering scheme from Kabat, E. A., et al., *Sequences of Proteins of Immunological Interest* (National Institutes of Health, Bethesda, Md. (1987)). In both FIG. 1A and FIG. 1B, the CDR residues determined according to a standard sequence definition (as in Kabat, E. A. et al., *Sequences of Proteins of Immunological Interest* (National Institutes of Health, Bethesda, Md., 1987)) are indicated by the first underlining beneath the sequences, and the CDR residues determined according to a structural definition (as in Chothia, C. & Lesk, A. M., *J. Mol. Biol.* 196:901–917 (1987)) are indicated by the second, lower underlines. The mismatches between genes are shown by the vertical lines.

FIG. 5 shows an amino acid sequence comparison of $V_L$ (top panel) and $V_H$ (lower panel) domains of the murine anti-CD3 monoclonal Ab UCHT1 (muxCD3, Shalaby et al., *J. Exp. Med.* 175, 217–225 (1992) with a humanized variant of this antibody (huxCD3v1). Also shown are consensus sequences (most commonly occurring residue or pair of residues) of the most abundant human subgroups, namely $V_L$ κ1 and $V_H$ III upon which the humanized sequences are based (Kabat, E. A. et al., *Sequences of Proteins of Immunological Interest*, 5th edition, National Institutes of Health, Bethesda, Md., USA (1991)). The light chain sequences—muxCD3v1 and huκl—correspond to SEQ.ID.NOs 16, 17, and 18, respectively. The heavy chain sequences—muxCD3, huxCD3v1 and huIII—correspond to SEQ.ID.NOs 19, 26, and 21, respectively. Residues which differ between muxCD3 and huxCD3v1 are identified by an asterisk (*), whereas those which differ between humanized and consensus sequences are identified by a sharp sign (#). A bullet (•) denotes that a residue at this position has been found to contact antigen in one or more crystallographic structures of antibody/antigen complexes (Kabat et al., 1991; Mian, I. S. et al., *J. Mol. Biol.* 217, 133–151 (1991)). The location of CDR residues according to a sequence definition (Kabat et al., 1991) and a structural definition (Chothia and Lesk, supra 1987) are shown by a line and carats (^) beneath the sequences respectively.

FIGS. 6A-1 and 6A-2 compare murine and humanized amino acid sequences for the heavy chain of an anti-CD18 antibody. H52H4-160 (SEQ. ID. NO. 22) is the murine sequence, and pH52–8.0 (SEQ. ID. NO. 23) is the humanized heavy chain sequence. pH52–8.0 residue 143S is the final amino acid in the variable heavy chain domain $V_H$, and residue 144A is the first amino acid in the constant heavy chain domain $C_{H1}$.

FIG. 6B compares murine and humanized amino acid sequences for the light chain of an anti-CD18 antibody.

Figure 2:
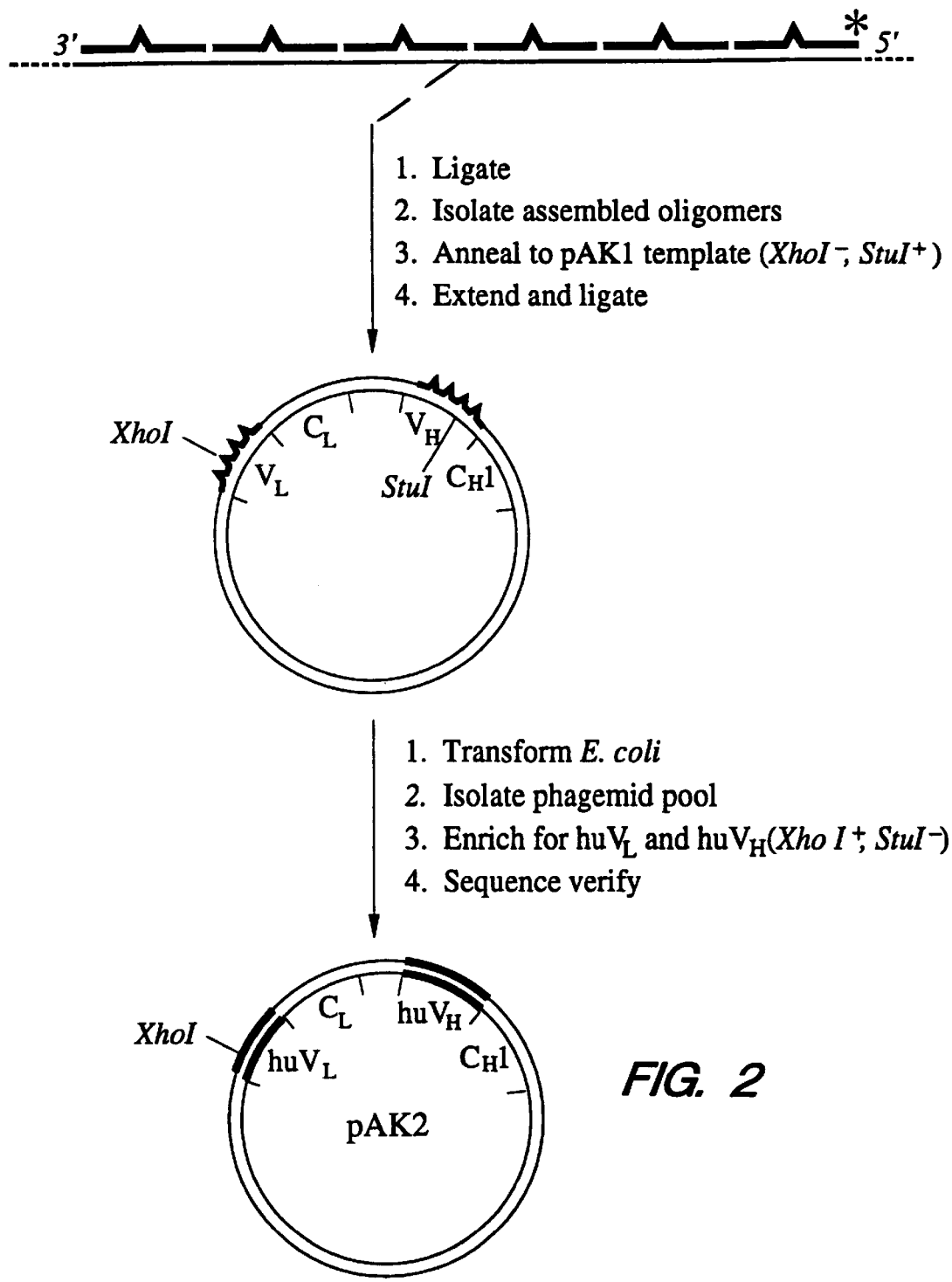
FIG. 2 shows a scheme for humanization of muMAb4D5 $V_L$ and $V_H$ by gene conversion mutagenesis.

H52L6-158 (SEQ. ID. NO.24) is the murine sequence, and pH52–9.0 (SEQ. ID. NO. 25) is the humanized light chain sequence. pH52–9.0 residue 128T is the final amino acid in the light chain variable domain $V_L$, and residue 129V is the first amino acid in the light chain constant domain $C_L$.

DETAILED DESCRIPTION OF THE INVENTION

Definitions

In general, the following words or phrases have the indicated definitions when used in the description, examples, and claims:

The murine monoclonal antibody known as muMAb4D5 (Fendly, B. M. et al., *Cancer Res.* 50:1550–1558 (1990)) is directed against the extracellular domain (ECD) of p185[HER2]. The muMAb4D5 and its uses are described in PCT application WO 89/06692 published Jul. 27, 1989. This murine antibody was deposited with the ATCC and designated ATCC CRL 10463. In this description and claims, the terms muMAb4D5, chMAb4D5 and huMAb4D5 represent murine, chimerized and humanized versions of the monoclonal antibody 4D5, respectively.

A humanized antibody for the purposes herein is an immunoglobulin amino acid sequence variant or fragment thereof which is capable of binding to a predetermined antigen and which comprises a FR region having substantially the amino acid sequence of a human immunoglobulin and a CDR having substantially the amino acid sequence of a non-human immunoglobulin.

Generally, a humanized antibody has one or more amino acid residues introduced into it from a source which is non-human. These non-human amino acid residues are referred to herein as "import" residues, which are typically taken from an "import" antibody domain, particularly a variable domain. An import residue, sequence, or antibody has a desired affinity and/or specificity, or other desirable antibody biological activity as discussed herein.

In general, the humanized antibody will comprise substantially all of at least one, and typically two, variable domains (Fab, Fab', F(ab')$_2$, Fabc, Fv) in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. Ordinarily, the antibody will contain both the light chain as well as at least the variable domain of a heavy chain. The antibody also may include the CH1, hinge, CH2, CH3, and CH4 regions of the heavy chain.

The humanized antibody will be selected from any class of immunoglobulins, including IgM, IgG, IgD, IgA and IgE, and any isotype, including IgG1, IgG2, IgG3 and IgG4. Usually the constant domain is a complement fixing constant domain where it is desired that the humanized antibody exhibit cytotoxic activity, and the class is typically IgG$_1$. Where such cytotoxic activity is not desirable, the constant domain may be of the IgG$_2$ class. The humanized antibody may comprise sequences from more than one class or isotype, and selecting particular constant domains to optimize desired effector functions is within the ordinary skill in the art.

The FR and CDR regions of the humanized antibody need not correspond precisely to the parental sequences, e.g., the import CDR or the consensus FR may be mutagenized by substitution, insertion or deletion of at least one residue so that the CDR or FR residue at that site does not correspond to either the consensus or the import antibody. Such mutations, however, will not be extensive. Usually, at least 75% of the humanized antibody residues will correspond to those of the parental FR and CDR sequences, more often 90%, and most preferably greater than 95%.

In general, humanized antibodies prepared by the method of this invention are produced by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen.

Residues that influence antigen binding are defined to be residues that are substantially responsible for the antigen affinity or antigen specificity of a candidate immunoglobulin, in a positive or a negative sense. The invention is directed to the selection and combination of FR residues from the consensus and import sequence so that the desired immunoglobulin characteristic is achieved. Such desired characteristics include increases in affinity and greater specificity for the target antigen, although it is conceivable that in some circumstances the opposite effects might be desired. In general, the CDR residues are directly and most substantially involved in influencing antigen binding (although not all CDR residues are so involved and therefore need not be substituted into the consensus sequence). However, FR residues also have a significant effect and can exert their influence in at least three ways: They may noncovalently directly bind to antigen, they may interact with CDR residues and they may affect the interface between the heavy and light chains.

A residue that noncovalently directly binds to antigen is one that, by three dimensional analysis, is reasonably expected to noncovalently directly bind to antigen. Typically, it is necessary to impute the position of antigen from the spatial location of neighboring CDRs and the dimensions and structure of the target antigen. In general, only those humanized antibody residues that are capable of forming salt bridges, hydrogen bonds, or hydrophobic interactions are likely to be involved in non-covalent antigen binding, however residues which have atoms which are separated from antigen spatially by 3.2 Angstroms or less may also non-covalently interact with antigen. Such residues typically are the relatively larger amino acids having the side chains with the greatest bulk, such as tyrosine, arginine, and lysine. Antigen-binding FR residues also typically will have side chains that are oriented into an envelope surrounding the solvent oriented face of a CDR which extends about 7 Angstroms into the solvent from the CDR domain and about 7 Angstroms on either side of the CDR domain, again as visualized by three dimensional modeling.

A residue that interacts with a CDR generally is a residue that either affects the conformation of the CDR polypeptide backbone or forms a noncovalent bond with a CDR residue side chain. Conformation-affecting residues ordinarily are those that change the spatial position of any CDR backbone atom (N, C$\alpha$, C, O, C$\beta$) by more than about 0.2 Angstroms. Backbone atoms of CDR sequences are displaced for example by residues that interrupt or modify organized structures such as beta sheets, helices or loops. Residues that can exert a profound affect on the conformation of neighboring sequences include proline and glycine, both of which are capable of introducing bends into the backbone. Other residues that can displace backbone atoms are those that are capable of participating in salt bridges and hydrogen bonds.

A residue that interacts with a CDR side chain is one that is reasonably expected to form a noncovalent bond with a CDR side chain, generally either a salt bridge or hydrogen bond. Such residues are identified by three dimensional positioning of their side chains. A salt or ion bridge could be expected to form between two side chains positioned within about 2.5–3.2 Angstroms of one another that bear opposite charges, for example a lysinyl and a glutamyl pairing. A hydrogen bond could be expected to form between the side chains of residue pairs such as seryl or threonyl with aspartyl or glutamyl (or other hydrogen accepting residues). Such pairings are well known in the protein chemistry art and will be apparent to the artisan upon three dimensional modeling of the candidate immunoglobulin.

Immunoglobulin residues that affect the interface between heavy and light chain variable regions ("the $V_L$–$V_H$ interface") are those that affect the proximity or orientation of the two chains with respect to one another. Certain residues involved in interchain interactions are already known and include $V_L$ residues 34, 36, 38, 44, 46, 87, 89, 91, 96, and 98 and $V_H$ residues 35, 37, 39, 45, 47, 91, 93, 95, 100, and 103 (utilizing the nomenclature set forth in Kabat et al., *Sequences of Proteins of Immunological Interest* (National Institutes of Health, Bethesda, Md., 1987)). Additional residues are newly identified by the inventors herein, and include 43L, 85L, 43H and 60H. While these residues are indicated for IgG only, they are applicable across species. In the practice of this invention, import antibody residues that are reasonably expected to be involved in interchain interactions are selected for substitution into the consensus sequence. It is believed that heretofore no humanized antibody has been prepared with an intrachain-affecting residue selected from an import antibody sequence.

Since it is not entirely possible to predict in advance what the exact impact of a given substitution will be it may be necessary to make the substitution and assay the candidate antibody for the desired characteristic. These steps, however, are per se routine and well within the ordinary skill of the art.

CDR and FR residues are determined according to a standard sequence definition (Kabat et al., *Sequences of Proteins of Immunological Interest*, National Institutes of Health, Bethesda Md. (1987), and a structural definition (as in Chothia and Lesk, *J. Mol. Biol.* 196:901–917 (1987). Where these two methods result in slightly different identifications of a CDR, the structural definition is preferred, but the residues identified by the sequence definition method are considered important FR residues for determination of which framework residues to import into a consensus sequence.

Throughout this description, reference is made to the numbering scheme from Kabat, E. A., et al., *Sequences of Proteins of Immunological Interest* (National Institutes of Health, Bethesda, Md. (1987) and (1991). In these compendiums, Kabat lists many amino acid sequences for antibodies for each subclass, and lists the most commonly occurring amino acid for each residue position in that subclass. Kabat uses a method for assigning a residue number to each amino acid in a listed sequence, and this method for assigning residue numbers has become standard in the field. The Kabat numbering scheme is followed in this description.

For purposes of this invention, to assign residue numbers to a candidate antibody amino acid sequence which is not included in the Kabat compendium, one follows the following steps. Generally, the candidate sequence is aligned with any immunoglobulin sequence or any consensus sequence in Kabat. Alignment may be done by hand, or by computer using commonly accepted computer programs; an example of such a program is the Align 2 program discussed in this description. Alignment may be facilitated by using some amino acid residues which are common to most Fab sequences. For example, the light and heavy chains each typically have two cysteines which have the same residue numbers; in $V_L$ domain the two cysteines are typically at residue numbers 23 and 88, and in the $V_H$ domain the two cysteine residues are typically numbered 22 and 92. Framework residues generally, but not always, have approximately the same number of residues, however the CDRs will vary in size. For example, in the case of a CDR from a candidate sequence which is longer than the CDR in the sequence in Kabat to which it is aligned, typically suffixes are added to the residue number to indicate the insertion of additional residues (see, e.g. residues 100abcde in FIG. 5). For candidate sequences which, for example, align with a Kabat sequence for residues 34 and 36 but have no residue between them to align with residue 35, the number 35 is simply not assigned to a residue.

Thus, in humanization of an import variable sequence, where one cuts out an entire human or consensus CDR and replaces it with an import CDR sequence, (a) the exact number of residues may be swapped, leaving the numbering the same, (b) fewer import amino acid residues may be introduced than are cut, in which case there will be a gap in the residue numbers, or (c) a larger number of amino acid residues may be introduced then were cut, in which case the numbering will involve the use of suffixes such as 100abcde.

The terms "consensus sequence" and "consensus antibody" as used herein refers to an amino acid sequence which comprises the most frequently occurring amino acid residues at each location in all immunoglobulins of any particular subclass or subunit structure. The consensus sequence may be based on immunoglobulins of a particular species or of many species. A "consensus" sequence, structure, or antibody is understood to encompass a consensus human sequence as described in certain embodiments of this invention, and to refer to an amino acid sequence which comprises the most frequently occurring amino acid residues at each location in all human immunoglobulins of any particular subclass or subunit structure. This invention provides consensus human structures and consensus structures which consider other species in addition to human.

The subunit structures of the five immunoglobulin classes in humans are as follows:

| Class | Heavy Chain | Subclasses | Light Chain | Molecular Formula |
|---|---|---|---|---|
| IgG | γ | γ1, γ2, γ3, γ4 | κ or λ | $(\gamma_2\kappa_2), (\gamma_2\lambda_2)$ |
| IgA | α | α1, α2 | κ or λ | $(\alpha_2\kappa_2)_n{}^a, (\alpha_2\lambda_2)_n{}^a$ |
| IgM | μ | none | κ or λ | $(\mu_2\kappa_2)_5, (\mu_2\lambda_2)_5$ |
| IgD | δ | none | κ or λ | $(\delta_2\kappa_2), (\delta_2\lambda_2)$ |
| IgE | ε | none | κ or λ | $(\epsilon_2\kappa_2), (\epsilon_2\lambda_2)$ |

($_n{}^a$ may equal 1, 2, or 3)

In preferred embodiments of an IgGγ1 human consensus sequence, the consensus variable domain sequences are derived from the most abundant subclasses in the sequence compilation of Kabat et al., *Sequences of Proteins of Immunological Interest*, National Institutes of Health, Bethesda Md, (1987), namely $V_L$ κ subgroup I and $V_H$ group III. In such preferred embodiments, the $V_L$ consensus domain has the amino acid sequence:

DIQMTQSPSSLSASVGDRVTITCRASQD-
VSSYLAWYQQKPGKAPKLLIYAASSLES-
GVPSRFSG SGSGTDFTLTISSLOPEDFATYYC-
QQYNSLPYTFGQGTKVEIKRT (SEQ. ID NO. 3);

the $V_H$ consensus domain has the amino acid sequence:

EVQLVESGGGLVQPGGSLRLSCAASG-
FTFSDYAMSWVRQAPGK-
GLEWVAVISENGSDTYYADS VKGRFTIS-
RDDSKNTLYLQMNSLRAEDTAVYYCARDRGG
AVSYFDVWGQGTLVTVSS.

These sequences include consensus CDRs as well as consensus FR residues (see for example in FIG. 1).

While not wishing to be limited to any particular theories, it may be that these preferred embodiments are less likely to be immunogenic in an individual than less abundant subclasses. However, in other embodiments, the consensus sequence is derived from other subclasses of human immunoglobulin variable domains. In yet other embodiments, the consensus sequence is derived from human constant domains.

Identity or homology with respect to a specified amino acid sequence of this invention is defined herein as the percentage of amino acid residues in a candidate sequence that are identical with the specified residues, after aligning the sequences and introducing gaps, if necessary, to achieve the maximum percent homology, and not considering any conservative substitutions as part of the sequence identity. None of N-terminal, C-terminal or internal extensions, deletions, or insertions into the specified sequence shall be construed as affecting homology. All sequence alignments called for in this invention are such maximal homology alignments. While such alignments may be done by hand using conventional methods, a suitable computer program is the "Align 2" program for which protection is being sought from the U.S. Register of Copyrights (Align 2, by Genentech, Inc., application filed Dec. 9, 1991).

"Non-homologous" import antibody residues are those residues which are not identical to the amino acid residue at the analogous or corresponding location in a consensus sequence, after the import and consensus sequences are aligned.

The term "computer representation" refers to information which is in a form that can be manipulated by a computer. The act of storing a computer representation refers to the act of placing the information in a form suitable for manipulation by a computer.

This invention is also directed to novel polypeptides, and in certain aspects, isolated novel humanized anti-p185$^{HER2}$ antibodies are provided. These novel anti-p185$^{HER2}$ antibodies are sometimes collectively referred to herein as huMAb4D5, and also sometimes as the light or heavy chain variable domains of huMAb4D5, and are defined herein to be any polypeptide sequence which possesses a biological property of a polypeptide comprising the following polypeptide sequence:

DIQMTQSPSSLSASVGDRVTITCRASQD-
VNTAVAWYQQKPGKAPKLLIYSASFLESGVP
SRFSGSRSGTDFTLTISSLQPEDFATYY-
CQQHYTTPPTFGQGTKVEIKRT (SEQ. ID NO. 1, which is the light chain variable domain of huMAb4D5); or

EVQLVESGGGLVQPGGSLRLSCAASG-
FNIKDTYIHWVRQAPGKGLEWVARIYPTNGYTR

YADSVKGRFTISADTSKNTAYLQMNSL-
RAEDTAVYYCSRWGGDGFYAMDVWGQGTLV
TVSS (SEQ. ID NO. 2, which is the heavy chain
variable domain of huMAb4D5).

"Biological property", as relates for example to anti-p185$^{HER2}$, for the purposes herein means an in vivo effector or antigen-binding function or activity that is directly or indirectly performed by huMAb4D5 (whether in its native or denatured conformation). Effector functions include p185$^{HER2}$ binding, any hormonal or hormonal antagonist activity, any mitogenic or agonist or antagonist activity, any cytotoxic activity. An antigenic function means possession of an epitope or antigenic site that is capable of cross-reacting with antibodies raised against the polypeptide sequence of huMAb4D5.

Biologically active huMAb4D5 is defined herein as a polypeptide that shares an effector function of huMAb4D5. A principal known effector function of huMAb4D5 is its ability to bind to p185$^{HER2}$.

Thus, the biologically active and antigenically active huMAb4D5 polypeptides that are the subject of certain embodiments of this invention include the sequence of the entire translated nucleotide sequence of huMAb4D5; mature huMAb4D5; fragments thereof having a consecutive sequence of at least 5, 10, 15, 20, 25, 30 or 40 amino acid residues comprising sequences from muMAb4D5 plus residues from the human FR of huMAb4D5; amino acid sequence variants of huMAb4D5 wherein an amino acid residue has been inserted N- or C-terminal to, or within, huMAb4D5 or its fragment as defined above; amino acid sequence variants of huMAb4D5 or its fragment as defined above wherein an amino acid residue of huMAb4D5 or its fragment as defined above has been substituted by another residue, including predetermined mutations by, e.g., site-directed or PCR mutagenesis; derivatives of huMAb4D5 or its fragments as defined above wherein huMAb4D5 or its fragments have been covalent modified, by substitution, chemical, enzymatic, or other appropriate means, with a moiety other than a naturally occurring amino acid; and glycosylation variants of huMAb4D5 (insertion of a glycosylation site or deletion of any glycosylation site by deletion, insertion or substitution of suitable residues). Such fragments and variants exclude any polypeptide heretofore identified, including muMAb4D5 or any known polypeptide fragment, which are anticipatory order 35 U.S.C. 102 as well as polypeptides obvious thereover under 35 U.S.C. 103.

An "isolated" polypeptide means polypeptide which has been identified and separated and/or recovered from a component of its natural environment. Contaminant components of its natural environment are materials which would interfere with diagnostic or therapeutic uses for the polypeptide, and may include enzymes, hormones, and other proteinaceous or nonproteinaceous solutes. In preferred embodiments, for example, a polypeptide product comprising huMAb4D5 will be purified from a cell culture or other synthetic environment (1) to greater than 95% by weight of protein as determined by the Lowry method, and most preferably more than 99% by weight, (2) to a degree sufficient to obtain at least 15 residues of N-terminal or internal amino acid sequence by use of a gas- or liquid-phase sequenator (such as a commercially available Applied Biosystems sequenator Model 470, 477, or 473), or (3) to homogeneity by SDS-PAGE under reducing or nonreducing conditions using Coomassie blue or, preferably, silver stain. Isolated huMAb4D5 includes huMAb4D5 in situ within recombinant cells since at least one component of the huMAb4D5 natural environment will not be present. Ordinarily, however, isolated huMAb4D5 will be prepared by at least one purification step.

In accordance with this invention, huMAb4D5 nucleic acid is RNA or DNA containing greater than ten bases that encodes a biologically or antigenically active huMAb4D5, is complementary to nucleic acid sequence encoding such huMAb4D5, or hybridizes to nucleic acid sequence encoding such huMAb4D5 and remains stably bound to it under stringent conditions, and comprises nucleic acid from a muMAb4D5 CDR and a human FR region.

Preferably, the huMAb4D5 nucleic acid encodes a polypeptide sharing at least 75% sequence identity, more preferably at least 80%, still more preferably at least 85%, even more preferably at 90%, and most preferably 95%, with the huMAb4D5 amino acid sequence. Preferably, a nucleic acid molecule that hybridizes to the huMAb4D5 nucleic acid contains at least 20, more preferably 40, and most preferably 90 bases. Such hybridizing or complementary nucleic acid, however, is further defined as being novel under 35 U.S.C. 102 and unobvious under 35 U.S.C. 103 over any prior art nucleic acid.

Stringent conditions are those that (1) employ low ionic strength and high temperature for washing, for example, 0.015 M NaCl/0.0015 M sodium citrate/0/1% NaDodSO$_4$ at 50° C.; (2) employ during hybridization a denaturing agent such as formamide, for example, 50% (vol/vol) formamide with 0.1% bovine serum albumin/0/1% Ficoll/0/1% polyvinylpyrrolidone/50 mM sodium phosphate buffer at pH 6.5 with 750 mM NaCl, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 g/ml), 0.1% SDS, and 10% dextran sulfate at 42 C, with washes at 42 C in 0.2×SSC and 0.1% SDS.

The term "control sequences" refers to DNA sequences necessary for the expression of an operably linked coding sequence in a particular host organism. The control sequences that are suitable for prokaryotes, for example, include a promoter, optionally an operator sequence, a ribosome binding site, and possibly, other as yet poorly understood sequences. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However enhancers do not have to be contiguous. Linking is accomplished by ligation at convenient restriction sites. If such sites do not exist, then synthetic oligonucleotide adaptors or linkers are used in accord with conventional practice.

An "exogenous" element is defined herein to mean nucleic acid sequence that is foreign to the cell, or homologous to the cell but in a position within the host cell nucleic acid in which the element is ordinarily not found.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

"Oligonucleotides" are short-length, single- or double-stranded polydeoxynucleotides that are chemically synthesized by known methods (such as phosphotriester, phosphite, or phosphoramidite chemistry, using solid phase techniques such as described in EP 266,032 published May 4, 1988, or via deoxynucleoside H-phosphonate intermediates as described by Froehler et al., *Nucl. Acids Res.*, 14: 5399–5407 119861). They are then purified on polyacrylamide gels.

The technique of "polymerase chain reaction," or "PCR," as used herein generally refers to a procedure wherein minute amounts of a specific piece of nucleic acid, RNA and/or DNA, are amplified as described in U.S. Pat. No. 4,683,195 issued Jul. 28, 1987. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al., *Cold Spring Harbor Symp. Quant. Biol.*, 51: 263 (1987); Erlich, ed., *PCR Technology*, (Stockton Press, NY, 1989). As used herein, PCR is considered to be one, but not the only, example of a nucleic acid polymerase reaction method for amplifying a nucleic acid test sample, comprising the use of a known nucleic acid (DNA or RNA) as a primer and utilizes a nucleic acid polymerase to amplify or generate a specific piece of nucleic acid or to amplify or generate a specific piece of nucleic acid which is complementary to a particular nucleic acid.

Suitable Methods for Practicing the Invention

Some aspects of this invention include obtaining an import, non-human antibody variable domain, producing a desired humanized antibody sequence and for humanizing an antibody gene sequence are described below. A particularly preferred method of changing a gene sequence, such as gene conversion from a non-human or consensus sequence into a humanized nucleic acid sequence, is the cassette mutagenesis procedure described in Example 1. Additionally, methods are given for obtaining and producing antibodies generally, which apply equally to native non-human antibodies as well as to humanized antibodies.

Generally, the antibodies and antibody variable domains of this invention are conventionally prepared in recombinant cell culture, as described in more detail below. Recombinant synthesis is preferred for reasons of safety and economy, but it is known to prepare peptides by chemical synthesis and to purify them from natural sources; such preparations are included within the definition of antibodies herein.

Molecular Modeling

An integral step in our approach to antibody humanization is construction of computer graphics models of the import and humanized antibodies. These models are used to determine if the six complementarity-determining regions (CDRs) can be successfully transplanted from the import framework to a human one and to determine which framework residues from the import antibody, if any, need to be incorporated into the humanized antibody in order to maintain CDR conformation. In addition, analysis of the sequences of the import and humanized antibodies and reference to the models can help to discern which framework residues are unusual and thereby might be involved in antigen binding or maintenance of proper antibody structure.

All of the humanized antibody models of this invention are based on a single three-dimensional computer graphics structure hereafter referred to as the consensus structure. This consensus structure is a key distinction from the approach of previous workers in the field, who typically begin by selecting a human antibody structure which has an amino acid sequence which is similar to the sequence of their import antibody.

The consensus structure of one embodiment of this invention was built in five steps as described below.

Step 1: Seven Fab X-ray crystal structures from the Brookhaven Protein Data Bank were used (entries 2FB4, 2RHE, 3FAB, and 1REI which are human structures, and 2MCP, 1FBJ, and 2HFL which are murine structures). For each structure, protein mainchain geometry and hydrogen bonding patterns were used to assign each residue to one of three secondary structure types: alpha-helix, beta-strand or other (i.e. non-helix and non-strand). The immunoglobulin residues used in superpositioning and those included in the consensus structure are shown in Table 1.

TABLE I

Immunoglobulin Residues Used in Superpositioning and Those Included in the Consensus Structure

| $Ig^a$ | $V_L\kappa$ domain | | | | | | | |
|---|---|---|---|---|---|---|---|---|
|  | 2FB4 | 2RHE | 2MCP | 3FAB | 1FBJ | 2HFL | 1REI | Consensus[b] |
|  |  |  |  |  |  |  |  | 2–11 |
|  | 18–24 | 18–24 | 19–25 | 18–24 | 19–25 | 19–25 | 19–25 | 16–27 |
|  | 32–37 | 34–39 | 39–44 | 32–37 | 32–37 | 32–37 | 33–38 | 33–39 |
|  |  |  |  |  |  |  |  | 41–49 |
|  | 60–66 | 62–68 | 67–72 | 53–66 | 60–65 | 60–65 | 61–66 | 59–77 |
|  | 69–74 | 71–76 | 76–81 | 69–74 | 69–74 | 69–74 | 70–75 |  |
|  | 84–88 | 86–90 | 91–95 | 84–88 | 84–88 | 84–88 | 85–89 | 82–91 |
|  |  |  |  |  |  |  |  | 101–105 |
| $RMS^c$ |  | 0.40 | 0.60 | 0.53 | 0.54 | 0.48 | 0.50 |  |

TABLE I-continued

Immunoglobulin Residues Used in Superpositioning and Those Included in the Consensus Structure

| | | | $V_H$ domain | | | | |
|---|---|---|---|---|---|---|---|
| | Ig[a] | 2FB4 | 2MCP | 3FAB | 1FBJ | 2HFL | Consensus[b] |
| | | | | | | | 3–8 |
| | | 18–25 | 18–25 | 18–25 | 18–25 | 18–25 | 17–23 |
| | | 34–39 | 34–39 | 34–39 | 34–39 | 34–39 | 33–41 |
| | | 46–52 | 46–52 | 46–52 | 46–52 | 46–52 | 45–51 |
| | | 57–61 | 59–63 | 56–60 | 57–61 | 57–61 | 57–61 |
| | | 68–71 | 70–73 | 67–70 | 68–71 | 68–71 | 66–71 |
| | | 78–84 | 80–86 | 77–83 | 78–84 | 78–84 | 75–82 |
| | | 92–99 | 94–101 | 91–98 | 92–99 | 92–99 | 88–94 |
| | | | | | | | 102–108 |
| | RMS[c] | | 0.43 | 0.85 | 0.62 | 0.91 | |
| | RMS[d] | 0.91 | 0.73 | 0.77 | 0.92 | | |

[a]Four-letter code for Protein Data Bank file.
[b]Residue numbers for the crystal structures are taken from the Protein Data Bank files. Residue numbers for the consensus structure are according to Kabat et al.
[c]Root-mean-square deviation in Å for (N,Cα,C) atoms superimposed on 2FB4.
[d]Root-mean-square deviation in Å for (N,Cα,C) atoms superimposed on 2HFL.

Step 2: Having identified the alpha-helices and beta-strands in each of the seven structures, the structures were superimposed on one another using the INSIGHT computer program (Biosym Technologies, San Diego, Calif.) as follows: The 2FB4 structure was arbitrarily chosen as the template (or reference) structure. The 2FB4 was held fixed in space and the s other six structures rotated and translated in space so that their common secondary structural elements (i.e. alpha-helices and beta-strands) were oriented such that these common elements were as close in position to one another as possible. (This superpositioning was performed using accepted mathematical formulae rather than actually physically moving the structures by hand.)

Step 3: With the seven structures thus superimposed, for each residue in the template (2FB4) Fab one calculates the distance from the template alpha-carbon atom (Cα) to the analogous Cα atom in each of the other six superimposed structures. This results in a table of Cα-Cα distances for each residue position in the sequence. Such a table is necessary in order to determine which residue positions will be included in the consensus model. Generally, if all Cα-Cα distances for a given residue position were ≦1.0 Å, that position was included in the consensus structure. If for a given position only one Fab crystal structure was >1.0 Å, the position was included but the outlying crystal structure was not included in the next step (for this position only). In general, the seven β-strands were included in the consensus structure while some of the loops connecting the β-strands, e.g. complementarity-determining regions (CDRs), were not included in view of Cα divergence.

Step 4: For each residue which was included in the consensus structure after step 3, the average of the coordinates for individual mainchain N, Cα, C, O and Cβ atoms were calculated. Due to the averaging procedure, as well as variation in bond length, bond angle and dihedral angle among the crystal structures, this "average" structure contained some bond lengths and angles which deviated from standard geometry. For purposes of this invention, "standard geometry" is understood to include geometries commonly accepted as typical, such as the compilation of bond lengths and angles from small molecule structures in Weiner, S. J. et. al., *J. Amer. Chem. Soc.*, 106: 765–784 (1984).

Step 5: In order to correct these deviations, the final step was to subject the "average" structure to 50 cycles of energy minimization (DISCOVER program, Biosym Technologies) using the AMBER (Weiner, S. J. et. al., *J. Amer. Chem. Soc.*, 106: 765–784 (1984)) parameter set with only the Cα coordinates fixed (i.e. all other atoms are allowed to move) (energy minimization is described below). This allowed any deviant bond lengths and angles to assume a standard (chemically acceptable) geometry. See Table II.

TABLE II

Average Bond Lengths and Angles for "Average" (Before) and Energy-Minimized Consensus (After 50 Cycles) Structures

| | $V_L\kappa$ before (Å) | $V_L\kappa$ after (Å) | $V_H$ before (Å) | $V_H$ after (Å) | Standard Geometry (Å) |
|---|---|---|---|---|---|
| N—Cα | 1.459 (0.012) | 1.451 (0.004) | 1.451 (0.023) | 1.452 (0.004) | 1.449 |
| Cα—C | 1.515 (0.012) | 1.523 (0.005) | 1.507 (0.033) | 1.542 (0.005) | 1.522 |
| O=C | 1.208 (0.062) | 1.229 (0.003) | 1.160 (0.177) | 1.231 (0.003) | 1.229 |
| C—N | 1.288 (0.049) | 1.337 (0.002) | 1.282 (0.065) | 1.335 (0.004) | 1.335 |
| Cα—Cβ | 1.508 (0.026) | 1.530 (0.002) | 1.499 (0.039) | 1.530 (0.002) | 1.526 |
| | (°) | (°) | (°) | (°) | (°) |
| C—N—Cα | 123.5 (4.2) | 123.8 (1.1) | 125.3 (4.6) | 124.0 (1.1) | 121.9 |

TABLE II-continued

Average Bond Lengths and Angles for "Average" (Before) and Energy-Minimized Consensus (After 50 Cycles) Structures

| N—Cα—C  | 110.0 (4.0) | 109.5 (1.9) | 110.3 (2.8) | 109.5 (1.6) | 110.1 |
|---------|-------------|-------------|-------------|-------------|-------|
| Cα—C—N  | 116.6 (4.0) | 116.6 (1.2) | 117.6 (5.2) | 116.6 (0.8) | 116.6 |
| O=C—N   | 123.1 (4.1) | 123.4 (0.6) | 122.2 (4.9) | 123.3 (0.4) | 122.9 |
| N—Cα—Cβ | 110.3 (2.1) | 109.8 (0.7) | 110.6 (2.5) | 109.8 (0.6) | 109.5 |
| Cβ—Cα—C | 311.4 (2.4) | 111.1 (0.7) | 111.2 (2.2) | 111.1 (0.6) | 111.1 |

Values in parentheses are standard deviations. Note that while some bond length and angle averages did Dot change appreciably after energy-minimization, the corresponding standard deviations are reduced due to deviant geometries assuming standard values after energy-minimization. Standard geometry values are from the AMBER forcefield as implemented in DISCOVER (Biosym Technologies).

The consensus structure might conceivably be dependent upon which crystal structure was chosen as the template on which the others were superimposed. As a test, the entire procedure was repeated using the crystal structure with the worst superposition versus 2FB4, i.e. the 2HFL Fab structure, as the new template (reference). The two consensus structures compare favorably (root-mean-squared deviation of 0.11 Å for all N, Cα and C atoms).

Note that the consensus structure only includes mainchain (N, Cα, C, O, Cβ atoms) coordinates for only those residues which are part of a conformation common to all seven X-ray crystal structures. For the Fab structures, these include the common β-strands (which comprise two β-sheets) and a few non-CDR loops which connect these β-strands. The consensus structure does not include CDRs or sidechains, both of which vary in their conformation among the seven structures. Also, note that the consensus structure includes only the VL and VH domains.

This consensus structure is used as the archetype. It is not particular to any species, and has only the basic shape without side chains. Starting with this consensus structure the model of any import, human, or humanized Fab can be constructed as follows. Using the amino acid sequence of the particular antibody VL and VH domains of interest, a computer graphics program (such as INSIGHT, Biosym Technologies) is used to add sidechains and CDRs to the consensus structure. When a sidechain is added, its conformation is chosen on the basis of known Fab crystal structures (see the Background section for publications of such crystal structures) and rotamer libraries (Ponder, J. W. & Richards, F. M., *J. Mol. Biol.* 193: 775–791 (1987)). The model also is constructed so that the atoms of the sidechain are positioned so as to not collide with other atoms in the Fab.

CDRs are added to the model (now having the backbone plus side chains) as follows. The size (i.e. number of amino acids) of each import CDR is compared to canonical CDR structures tabulated by Chothia et al., *Nature*, 342:877–883 (1989)) and which were derived from Fab crystals. Each CDR sequence is also reviewed for the presence or absence of certain specific amino acid residues which are identified by Chothia as structurally important: e.g. light chain residues 29 (CDR1) and 95 (CDR3), and heavy chain residues 26, 27, 29 (CDR1) and 55 (CDR2). For light chain CDR2, and heavy chain CDR3, only the size of the CDR is compared to the Chothia canonical structure. If the size and sequence (i.e. inclusion of the specific, structurally important residues as denoted by Chothia et al.) of the import CDR agrees in size and has the same structurally important residues as those of a canonical CDR, then the mainchain conformation of the import CDR in the model is taken to be the same as that of the canonical CDR. This means that the import sequence is assigned the structural configuration of the canonical CDR, which is then incorporated in the evolving model.

However, if no matching canonical CDR can be assigned for the import CDR, then one of two options can be exercised. First, using a program such as INSIGHT (Biosym Technologies), the Brookhaven Protein Data Bank can be searched for loops with a similar size to that of the import CDR and these loops can be evaluated as possible conformations for the import CDR in the model. Minimally, such loops must exhibit a conformation in which no loop atom overlaps with other protein atoms. Second, one can use available programs which calculate possible loop conformations, assuming a given loop size, using methods such as described by Bruccoleri et al., *Nature* 335: 564–568 (1988).

When all CDRs and sidechains have been added to the consensus structure to give the final model (import, human or humanized), the model is preferably subjected to energy minimization using programs which are available commercially (e.g. DISCOVER, Biosym Technologies). This technique uses complex mathematical formulae to refine the model by performing such tasks as checking that all atoms are within appropriate distances from one another and checking that bond lengths and angles are within chemically acceptable limits.

Models of a humanized, import or human antibody sequence are used in the practice of this invention to understand the impact of selected amino acid residues of the activity of the sequence being modeled. For example, such a model can show residues which may be important in antigen binding, or for maintaining the conformation of the antibody, as discussed in more detail below. Modeling can also be used to explore the potential impact of changing any amino acid residue in the antibody sequence.

Methods for Obtaining a Humanized Antibody Sequence

In the practice of this invention, the first step in humanizing an import antibody is deriving a consensus amino acid sequence into which to incorporate the import sequences. Next a model is generated for these sequences using the methods described above. In certain embodiments of this invention, the consensus human sequences are derived from the most abundant subclasses in the sequence compilation of Kabat et al. (Kabat, E. A. et al., *Sequences of Proteins of Immunological Interest* (National Institutes of Health, Bethesda, Md., 1987)), namely $V_L$ κ subgroup I and $V_H$ group III, and have the sequences indicated in the definitions above.

While these steps may be taken in different order, typically a structure for the candidate humanized antibody is created by transferring the at least one CDR from the non-human, import sequence into the consensus human structure, after the entire corresponding human CDR has been removed. The humanized antibody may contain human replacements of the non-human import residues at positions within CDRs as defined by sequence variability (Kabat, E. A. et al., *Sequences of Proteins of Immunological Interest* (National Institutes of Health, Bethesda, Md., 1987)) or as defined by structural variability (Chothia, C. & Lesk, A. M., *J. Mol. Biol.* 196:901–917 (1987)). For example, huMAb4D5 contains human replacements of the muMAb4D5 residues at three positions within CDRs as defined by sequence variability (Kabat, E. A. et al., *Sequences of Proteins of Immunological Interest* (National Institutes of Health, Bethesda, Md., 1987)) but not as defined by structural variability (Chothia, C. & Lesk, A. M., *J. Mol. Biol.* 196:901–917 (1987)): $V_L$-CDR1 K24R, $V_L$-CDR2 R54L and $V_L$-CDR2 T56S.

Differences between the non-human import and the human consensus framework residues are individually investigated to determine their possible influence on CDR conformation and/or binding to antigen. Investigation of such possible influences is desirably performed through modeling, by examination of the characteristics of the amino acids at particular locations, or determined experimentally through evaluating the effects of substitution or mutagenesis of particular amino acids.

In certain preferred embodiments of this invention, a humanized antibody is made comprising amino acid sequence of an import, non-human antibody and a human antibody, utilizing the steps of:
  a. obtaining the amino acid sequences of at least a portion of an import antibody variable domain and of a consensus human variable domain;
  b. identifying Complementarity Determining Region (CDR) amino acid sequences in the import and the human variable domain sequences;
  c. substituting an import CDR amino acid sequence for the corresponding human CDR amino acid sequence;
  d. aligning the amino acid sequences of a Framework Region (FR) of the import antibody and the corresponding FR of the consensus antibody;
  e. identifying import antibody FR residues in the aligned FR sequences that are non-homologous to the corresponding consensus antibody residues;
  f. determining if the non-homologous import amino acid residue is reasonably expected to have at least one of the following effects:
    1. non-covalently binds antigen directly,
    2. interacts with a CDR; or
    3. participates in the $V_L$–$V_H$ interface; and
  g. for any non-homologous import antibody amino acid residue which is reasonably expected to have at least one of these effects, substituting that residue for the corresponding amino acid residue in the consensus antibody FR sequence.

Optionally, one determines if any non-homologous residues identified in step (e) are exposed on the surface of the domain or buried within it, and if the residue is exposed but has none of the effects identified in step (f), one may retain the consensus residue.

Additionally, in certain embodiments the corresponding consensus antibody residues identified in step (e) above are selected from the group consisting of 4L, 35L, 36L, 38L, 43L, 44L, 46L, 58L, 62L, 63L, 64L, 65L, 66L, 67L, 68L, 69L, 70L, 71L, 73L, 85L, 87L, 98L, 2H, 4H, 24H, 36H, 37H, 39H, 43H, 45H, 49H, 58H, 60H, 67H, 68H, 69H, 70H, 73H, 74H, 75H, 76H, 78H, 91H, 92H, 93H, and 103H (utilizing the numbering system set forth in Kabat, E. A. et al., *Sequences of Proteins of Immunological Interest* (National Institutes of Health, Bethesda, Md., 1987)).

In preferred embodiments, the method of this invention comprises the additional steps of searching either or both of the import, non-human and the consensus variable domain sequences for glycosylation sites, determining if the glycosylation is reasonably expected to be important for the desired antigen binding and biological activity of the antibody (i.e., determining if the glycosylation site binds to antigen or changes a side chain of an amino acid residue that binds to antigen, or if the glycosylation enhances or weakens antigen binding, or is important for maintaining antibody affinity). If the import sequence bears the glycosylation site, it is preferred to substitute that site for the corresponding residues in the consensus human sequence if the glycosylation site is reasonably expected to be important. If only the consensus sequence, and not the import, bears the glycosylation site, it is preferred to eliminate that glycosylation site or substitute therefor the corresponding amino acid residues from the import sequence.

Another preferred embodiment of the methods of this invention comprises aligning import antibody and the consensus antibody FR sequences, identifying import antibody FR residues which are non-homologous with the aligned consensus FR sequence, and for each such non-homologous import antibody FR residue, determining if the corresponding consensus antibody residue represents a residue which is highly conserved across all species at that site, and if it is so conserved, preparing a humanized antibody which comprises the consensus antibody amino acid residue at that site.

In certain alternate embodiments, one need not utilize the modeling and evaluation steps described above, and may instead proceed with the steps of obtaining the amino acid sequence of at least a portion of an import, non-human antibody variable domain having a CDR and a FR, obtaining the amino acid sequence of at least a portion of a consensus human antibody variable domain having a CDR and a FR, substituting the non-human CDR for the human CDR in the consensus human antibody variable domain, and then substituting an amino acid residue for the consensus amino acid residue at at least one of the following sites:
  a. (in the FR of the variable domain of the light chain) 4L, 35L, 36L, 38L, 43L, 44L, 58L, 46L, 62L, 63L, 64L, 65L, 66L, 67L, 68L, 69L, 70L, 71L, 87L, 98L, or
  b. (in the FR of the variable domain of the heavy chain) 2H, 4H, 24H, 36H, 37H, 39H, 43H, 45H, 49H, 58H, 60H, 67H, 68H, 69H, 70H, 73H, 74H, 75H, 76H, 78H, 91H, 92H, 93H, and 103H.

Preferably, the non-CDR residue substituted at the consensus FR site is the residue found at the corresponding location of the non-human antibody. If desired, one may utilize the other method steps described above for determining whether a particular amino acid residue can reasonably be expected to have undesirable effects, and remedying those effects.

If after making a humanized antibody according to the steps above and testing its activity one is not satisfied with the humanized antibody, one preferably reexamines the potential effects of the amino acids at the specific locations recited above. Additionally, it is desirable to reinvestigate any buried residues which are reasonably expected to affect the $V_L$–$V_H$ interface but may not directly affect CDR conformation. It is also desirable to reevaluate the humanized antibody utilizing the steps of the methods claimed herein.

In certain embodiments of this invention, amino acid residues in the consensus human sequence are substituted for by other amino acid residues. In preferred embodiments, residues from a particular non-human import sequence are substituted, however there are circumstances where it is desired to evaluate the effects of other amino acids. For example, if after making a humanized antibody according to the steps above and testing its activity one is not satisfied with the humanized antibody, one may compare the sequences of other classes or subgroups of human antibodies, or classes or subgroups of antibodies from the particular non-human species, and determine which other amino acid side chains and amino acid residues are found at particular locations and substituting such other residues.

Antibodies

Certain aspects of this invention are directed to natural antibodies and to monoclonal antibodies, as illustrated in the Examples below and by antibody hybridomas deposited with the ATCC (as described below). Thus, the references throughout this description to the use of monoclonal antibodies are intended to include the use of natural or native antibodies as well as humanized and chimeric antibodies. As used herein, the term "antibody" includes the antibody variable domain and other separable antibody domains unless specifically excluded.

In accordance with certain aspects of this invention, antibodies to be humanized (import antibodies) are isolated from continuous hybrid cell lines formed by the fusion of antigen-primed immune lymphocytes with myeloma cells.

In certain embodiments, the antibodies of this invention are obtained by routine screening. Polyclonal antibodies to an antigen generally are raised in animals by multiple subcutaneous (sc) or intraperitoneal (ip) injections of the antigen and an adjuvant. It may be useful to conjugate the antigen or a fragment containing the target amino acid sequence to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

The route and schedule of the host animal or cultured antibody-producing cells therefrom are generally in keeping with established and conventional techniques for antibody stimulation and production. While mice are frequently employed as the test model, it is contemplated that any mammalian subject including human subjects or antibody-producing cells obtained therefrom can be manipulated according to the processes of this invention to serve as the basis for production of mammalian, including human, hybrid cell lines.

Animals are typically immunized against the immunogenic conjugates or derivatives by combining 1 mg or 1 μg of conjugate (for rabbits or mice, respectively) with 3 volumes of Freund's complete adjuvant and injecting the solution intradermally at multiple sites. One month later the animals are boosted with 1/5 to 1/10 the original amount of conjugate in Freund's complete adjuvant (or other suitable adjuvant) by subcutaneous injection at multiple sites. 7 to 14 days later animals are bled and the serum is assayed for antigen titer. Animals are boosted until the titer plateaus. Preferably, the animal is boosted with the conjugate of the same antigen, but conjugated to a different protein and/or through a different cross-linking agent. Conjugates also can be made in recombinant cell culture as protein fusions. Also, aggregating agents such as alum are used to enhance the immune response.

After immunization, monoclonal antibodies are prepared by recovering immune lymphoid cells—typically spleen cells or lymphocytes from lymph node tissue—from immunized animals and immortalizing the cells in conventional fashion, e.g. by fusion with myeloma cells or by Epstein-Barr (EB)-virus transformation and screening for clones expressing the desired antibody.

The hybridoma technique described originally by Kohler and Milstein, *Eur. J. Immunol.* 6:511 (1976) has been widely applied to produce hybrid cell lines that secrete high levels of monoclonal antibodies against many specific antigens.

It is possible to fuse cells of one species with another. However, it is preferable that the source of the immunized antibody producing cells and the myeloma be from the same species.

The hybrid cell lines can be maintained in culture in vitro in cell culture media. The cell lines of this invention can be selected and/or maintained in a composition comprising the continuous cell line in hypoxanthine-aminopterin thymidine (HAT) medium. In fact, once the hybridoma cell line is established, it can be maintained on a variety of nutritionally adequate media. Moreover, the hybrid cell lines can be stored and preserved in any number of conventional ways, including freezing and storage under liquid nitrogen. Frozen cell lines can be revived and cultured indefinitely with resumed synthesis and secretion of monoclonal antibody. The secreted antibody is recovered from tissue culture supernatant by conventional methods such as precipitation, Ion exchange chromatography, affinity chromatography, or the like. The antibodies described herein are also recovered from hybridoma cell cultures by conventional methods for purification of IgG or IgM as the case may be that heretofore have been used to purify these immunoglobulins from pooled plasma, e.g. ethanol or polyethylene glycol precipitation procedures. The purified antibodies are sterile filtered, and optionally are conjugated to a detectable marker such as an enzyme or spin label for use in diagnostic assays of the antigen in test samples.

While routinely rodent monoclonal antibodies are used as the source of the import antibody, the invention is not limited to any species. Additionally, techniques developed for the production of chimeric antibodies (Morrison et al., *Proc. Natl. Acad. Sci.*, 81:6851 (1984); Neuberger et al., *Nature* 312:604 (1984); Takeda et al., *Nature* 314:452 (1985)) by splicing the genes from a mouse antibody molecule of appropriate antigen specificity together with genes from a human antibody molecule of appropriate biological activity (such as ability to activate human complement and mediate ADCC) can be used; such antibodies are within the scope of this invention.

Techniques for creating recombinant DNA versions of the antigen-binding regions of antibody molecules (known as Fab fragments) which bypass the generation of monoclonal antibodies are encompassed within the practice of this invention. One extracts antibody-specific messenger RNA molecules from immune system cells taken from an immunized animal, transcribes these into complementary DNA (cDNA), and clones the cDNA into a bacterial expressions system. One example of such a technique suitable for the practice of this invention was developed by researchers at Scripps/Stratagene, and incorporates a proprietary bacteriophage lambda vector system which contains a leader sequence that causes the expressed Fab protein to migrate to the periplasmic space (between the bacterial cell membrane and the cell wall) or to be secreted. One can rapidly generate and screen great numbers of functional FAb fragments for those which bind the antigen. Such FAb fragments with specificity for the antigen are specifically encompassed within the term "antibody" as it is defined, discussed, and claimed herein.

Amino Acid Sequence Variants

Amino acid sequence variants of the antibodies and polypeptides of this invention (referred to in herein as the target polypeptide) are prepared by introducing appropriate nucleotide changes into the DNA encoding the target polypeptide, or by in vitro synthesis of the desired target polypeptide. Such variants include, for example, humanized variants of non-human antibodies, as well as deletions from, or insertions or substitutions of, residues within particular amino acid sequences. Any combination of deletion, insertion, and substitution can be made to arrive at the final construct, provided that the final construct possesses the desired characteristics. The amino acid changes also may alter post-translational processes of the target polypeptide, such as changing the number or position of glycosylation sites, altering any membrane anchoring characteristics, and/or altering the intra-cellular location of the target polypeptide by inserting, deleting, or otherwise affecting any leader sequence of the native target polypeptide.

In designing amino acid sequence variants of target polypeptides, the location of the mutation site and the nature of the mutation will depend on the target polypeptide characteristic(s) to be modified. The sites for mutation can be modified individually or in series, e.g., by (1) substituting first with conservative amino acid choices and then with more radical selections depending upon the results achieved, (2) deleting the target residue, or (3) inserting residues of the same or a different class adjacent to the located site, or combinations of options 1–3. In certain embodiments, these choices are guided by the methods for creating humanized sequences set forth above.

A useful method for identification of certain residues or regions of the target polypeptide that are preferred locations for mutagenesis is called "alanine scanning mutagenesis" as described by Cunningham and Wells (*Science*, 244: 1081–1085 [1989]). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with the surrounding aqueous environment in or outside the cell. Those domains demonstrating functional sensitivity to the substitutions then are refined by introducing further or other variants at or for the sites of substitution. Thus, while the site for introducing an amino acid sequence variation is predetermined, the nature of the mutation per se need not be predetermined. For example, to optimize the performance of a mutation at a given site, ala scanning or random mutagenesis may be conducted at the target codon or region and the expressed target polypeptide variants are screened for the optimal combination of desired activity.

There are two principal variables in the construction of amino acid sequence variants: the location of the mutation site and the nature of the mutation. In general, the location and nature of the mutation chosen will depend upon the target polypeptide characteristic to be modified.

Amino acid sequence deletions of antibodies are generally not preferred, as maintaining the generally configuration of an antibody is believed to be necessary for its activity. Any deletions will be selected so as to preserve the structure of the target antibody.

Amino acid sequence insertions include amino- and/or carboxyl-terminal fusions ranging in length from one residue to polypeptides containing a hundred or more residues, as well as intrasequence insertions of single or multiple amino acid residues. Intrasequence insertions (i.e., insertions within the target polypeptide sequence) may range generally from about 1 to 10 residues, more preferably 1 to 5, most preferably 1 to 3. Examples of terminal insertions include the target polypeptide with an N-terminal methionyl residue, an artifact of the direct expression of target polypeptide in bacterial recombinant cell culture, and fusion of a heterologous N-terminal signal sequence to the N-terminus of the target polypeptide molecule to facilitate the secretion of the mature target polypeptide from recombinant host cells. Such signal sequences generally will be obtained from, and thus homologous to, the intended host cell species. Suitable sequences include STII or Ipp for *E. coli*, alpha factor for yeast, and viral signals such as herpes gD for mammalian cells.

Other insertional variants of the target polypeptide include the fusion to the N- or C-terminus of the target polypeptide of immunogenic polypeptides, e.g., bacterial polypeptides such as beta-lactamase or an enzyme encoded by the *E. coli* trp locus, or yeast protein, and C-terminal fusions with proteins having a long half-life such as immunoglobulin constant regions (or other immunoglobulin regions), albumin, or ferritin, as described in WO 89/02922 published Apr. 6, 1989.

Another group of variants are amino acid substitution variants. These variants have at least one amino acid residue in the target polypeptide molecule removed and a different residue inserted in its place. The sites of greatest interest for substitutional mutagenesis include sites identified as the active site(s) of the target polypeptide, and sites where the amino acids found in the target polypeptide from various species are substantially different in terms of side-chain bulk, charge, and/or hydrophobicity. Other sites for substitution are described infra, considering the effect of the substitution of the antigen binding, affinity and other characteristics of a particular target antibody.

Other sites of interest are those in which particular residues of the target polypeptides obtained from various species are identical. These positions may be important for the biological activity of the target polypeptide. These sites, especially those falling within a sequence of at least three other identically conserved sites, are substituted in a relatively conservative manner. If such substitutions result in a change in biological activity, then other changes are introduced and the products screened until the desired effect is obtained.

Substantial modifications in function or immunological identity of the target polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side chain properties:

(1) hydrophobic: norleucine, met, ala, val, leu, ile;
(2) neutral hydrophilic: cys, ser, thr;
(3) acidic: asp, glu;
(4) basic: asn, gin, his, lys, arg;

(5) residues that influence chain orientation: gly, pro; and
(6) aromatic: trp, tyr, phe.

Non-conservative substitutions will entail exchanging a member of one of these classes for another. Such substituted residues may be introduced into regions of the target polypeptide that are homologous with other antibodies of the same class or subclass, or, more preferably, into the non-homologous regions of the molecule.

Any cysteine residues not involved in maintaining the proper conformation of target polypeptide also may be substituted, generally with serine, to improve the oxidative stability of the molecule and prevent aberrant crosslinking.

DNA encoding amino acid sequence variants of the target polypeptide is prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the target polypeptide. A particularly preferred method of gene conversion mutagenesis is described below in Example 1. These techniques may utilized target polypeptide nucleic acid (DNA or RNA), or nucleic acid complementary to the target polypeptide nucleic acid.

Oligonucleotide-mediated mutagenesis is a preferred method for preparing substitution, deletion, and insertion variants of target polypeptide DNA. This technique is well known in the art as described by Adelman et al., *DNA*, 2: 183 (1983). Briefly, the target polypeptide DNA is altered by hybridizing an oligonucleotide encoding the desired mutation to a DNA template, where the template is the single-stranded form of a plasmid or bacteriophage containing the unaltered or native DNA sequence of the target polypeptide. After hybridization, a DNA polymerase is used to synthesize an entire second complementary strand of the template that will thus incorporate the oligonucleotide primer, and will code for the selected alteration in the target polypeptide DNA.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et a. (*Proc. Natl. Acad. Sci. USA*, 75: 5765 [1978]).

Single-stranded DNA template may also be generated by denaturing double-stranded plasmid (or other) DNA using standard techniques.

For alteration of the native DNA sequence (to generate amino acid sequence variants, for example), the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the mutated form of the target polypeptide, and the other strand (the original template) encodes the native, unaltered sequence of the target polypeptide. This heteroduplex molecule is then transformed into a suitable host cell, usually a prokaryote such as *E. coli* JM101. After the cells are grown, they are plated onto agarose plates and screened using the oligonucleotide primer radiolabeled with 32-phosphate to identify the bacterial colonies that contain the mutated DNA. The mutated region is then removed and placed in an appropriate vector for protein production, generally an expression vector of the type typically employed for transformation of an appropriate host.

The method described immediately above may be modified such that a homoduplex molecule is created wherein both strands of the plasmid contain the mutationis). The modifications are as follows: The single-stranded oligonucleotide is annealed to the single-stranded template as described above. A mixture of three deoxyribonucleotides, deoxyriboadenosine (dATP), deoxyriboguanosine (dGTP), and deoxyribothymidine (dTTP), is combined with a modified thio-deoxyribocytosine called dCTP-(aS) (which can be obtained from Amersham Corporation). This mixture is added to the template-oligonucleotide complex. Upon addition of DNA polymerase to this mixture, a strand of DNA identical to the template except for the mutated bases is generated. In addition, this new strand of DNA will contain dCTP-(aS) instead of dCTP, which serves to protect it from restriction endonuclease digestion.

After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as *E. coli* JM101, as described above.

DNA encoding target polypeptide variants with more than one amino acid to be substituted may be generated in one of several ways. If the amino acids are located close together in the polypeptide chain, they may be mutated simultaneously using one oligonucleotide that codes for all of the desired amino acid substitutions. If, however, the amino acids are located some distance from each other (separated by more than about ten amino acids), it is more difficult to generate a single oligonucleotide that encodes all of the desired changes. Instead, one of two alternative methods may be employed.

In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions.

The alternative method involves two or more rounds of mutagenesis to produce the desired mutant. The first round is as described for the single mutants: wild-type DNA is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

PCR mutagenesis is also suitable for making amino acid variants of target polypeptide. While the following discussion refers to DNA, it is understood that the technique also finds application with RNA. The PCR technique generally refers to the following procedure (see Erlich, supra, the chapter by R. Higuchi, p. 61–70): When small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template. For introduction of a mutation into a plasmid DNA, one of the primers is designed to overlap the position of the mutation and to contain the mutation; the sequence of the other primer must be identical to a stretch of sequence of the opposite strand of the plasmid, but this sequence can be located anywhere along the plasmid DNA. It is preferred, however, that the sequence of the second primer is located within 200 nucleotides from that of the first, such that in the end the entire amplified region of DNA bounded by the primers can be easily sequenced. PCR amplification using a primer pair like the one just described results in a population of DNA fragments that differ at the position of the mutation specified by the primer, and possibly at other positions, as template copying is somewhat error-prone.

If the ratio of template to product material is extremely low, the vast majority of product DNA fragments incorporate the desired mutation(s). This product material is used to replace the corresponding region in the plasmid that served as PCR template using standard DNA technology. Mutations at separate positions can be introduced simultaneously by either using a mutant second primer, or performing a second PCR with different mutant primers and ligating the two resulting PCR fragments simultaneously to the vector fragment in a three (or more)-part ligation.

In a specific example of PCR mutagenesis, template plasmid DNA (1 μg) is linearized by digestion with a restriction endonuclease that has a unique recognition site in the plasmid DNA outside of the region to be amplified. Of this material, 100 ng is added to a PCR mixture containing PCR buffer, which contains the four deoxynucleotide triphosphates and is included in the GeneAmp® kits (obtained from Perkin-Elmer Cetus, Norwalk, Conn. and Emeryville, Calif.), and 25 pmole of each oligonucleotide primer, to a final volume of 50 μl. The reaction mixture is overlayed with 35 μl mineral oil. The reaction is denatured for 5 minutes at 100° C., placed briefly on ice, and then 1 μl *Thermus aquaticus* (*Taq*) DNA polymerase (5 units/μl, purchased from Perkin-Elmer Cetus, Norwalk, Conn. and Emeryville, Calif.) is added below the mineral oil layer. The reaction mixture is then inserted into a DNA Thermal Cycler (purchased from Perkin-Elmer Cetus) programmed as follows: 2 min. at 55° C., then 30 sec. at 72° C., then 19 cycles of the following: 30 sec. at 94° C., 30 sec. at 55° C., and 30 sec. at 72° C.

At the end of the program, the reaction vial is removed from the thermal cycler and the aqueous phase transferred to a new vial, extracted with phenol/chloroform (50:50:vol), and ethanol precipitated, and the DNA is recovered by standard procedures. This material is subsequently subjected to the appropriate treatments for insertion into a vector.

Another method for preparing variants, cassette mutagenesis, is based on the technique described by Wells et al. (*Gene*, 315 [1985]). The starting material is the plasmid (or other vector) comprising the target polypeptide DNA to be mutated. The codon(s) in the target polypeptide DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the target polypeptide DNA. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are compatible with the ends of the linearized plasmid, such that it can be directly ligated to the plasmid. This plasmid now contains the mutated target polypeptide DNA sequence.

Insertion of DNA into a Cloning Vehicle

The cDNA or genomic DNA encoding the target polypeptide is inserted into a replicable vector for further cloning (amplification of the DNA) or for expression. Many vectors are available, and selection of the appropriate vector will depend on 1) whether it is to be used for DNA amplification or for DNA expression, 2) the size of the DNA to be inserted into the vector, and 3) the host cell to be transformed with the vector. Each vector contains various components depending on its function (amplification of DNA or expression of DNA) and the host cell for which it is compatible. The vector components generally include, but are not limited to, one or more of the following: a signal sequence, an origin of replication, one or more marker genes, an enhancer element, a promoter, and a transcription termination sequence.

(a) Signal Sequence Component

In general, the signal sequence may be a component of the vector, or it may be a part of the target polypeptide DNA that is inserted into the vector.

The target polypeptides of this invention may be expressed not only directly, but also as a fusion with a heterologous polypeptide, preferably a signal sequence or other polypeptide having a specific cleavage site at the N-terminus of the mature protein or polypeptide. In general, the signal sequence may be a component of the vector, or it may be a part of the target polypeptide DNA that is inserted into the vector. Included within the scope of this invention are target polypeptides with any native signal sequence deleted and replaced with a heterologous signal sequence. The heterologous signal sequence selected should be one that is recognized and processed (i.e. cleaved by a signal peptidase) by the host cell. For prokaryotic host cells that do not recognize and process the native target polypeptide signal sequence, the signal sequence is substituted by a prokaryotic signal sequence selected, for example, from the group of the alkaline phosphatase, penicillinase, Ipp, or heat-stable enterotoxin II leaders. For yeast secretion the native target polypeptide signal sequence may be substituted by the yeast invertase, alpha factor, or acid phosphatase leaders. In mammalian cell expression the native signal sequence is satisfactory, although other mammalian signal sequences may be suitable.

(b) Origin of Replication Component

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Most expression vectors are "shuttle" vectors, i.e. they are capable of replication in at least one class of organisms but can be transfected into another organism for expression. For example, a vector is cloned in *E. coli* and then the same vector is transfected into yeast or mammalian cells for expression even though it is not capable of replicating independently of the host cell chromosome.

DNA may also be amplified by insertion into the host genome. This is readily accomplished using Bacillus species as hosts, for example, by including in the vector a DNA sequence that is complementary to a sequence found in Bacillus genomic DNA. Transfection of Bacillus with this vector results in homologous recombination with the genome and insertion of the target polypeptide DNA. However, the recovery of genomic DNA encoding the target polypeptide is more complex than that of an exogenously replicated vector because restriction enzyme digestion is required to excise the target polypeptide DNA.

(c) Selection Gene Component

Expression and cloning vectors should contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g. ampicillin, neomycin, methotrexate, or tetracycline, (b) complement auxotrophic deficiencies, or (c) supply critical nutrients not available from complex media, e.g. the gene encoding D-alanine racemase for Bacilli.

One example of a selection scheme utilizes a drug to arrest growth of a host cell.

Those cells that are successfully transformed with a heterologous gene express a protein conferring drug resistance and thus survive the selection regimen. Examples of such dominant selection use the drugs neomycin (Southern et al., *J. Molec. Appl. Genet.*, 1: 327 [1982]), mycophenolic acid (Mulligan et al., *Science*, 209: 1422 [1980]) or hygromycin (Sugden et al., *Mol. Cell. Biol.*, 5: 410–413 [1985]). The three examples given above employ bacterial genes under eukaryotic control to convey resistance to the appropriate drug G418 or neomycin (geneticin), xgpt (mycophenolic acid), or hygromycin, respectively.

Another example of suitable selectable markers for mammalian cells are those that enable the identification of cells competent to take up the target polypeptide nucleic acid, such as dihydrofolate reductase (DHFR) or thymidine kinase. The mammalian cell transformants are placed under selection pressure which only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes the target polypeptide. Amplification is the process by which genes in greater demand for the production of a protein critical for growth are reiterated in tandem within the chromosomes of successive generations of recombinant cells. Increased quantities of the target polypeptide are synthesized from the amplified DNA.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity, prepared and propagated as described by Urlaub and Chasin, *Proc. Natl. Acad. Sci. USA*, 77: 4216 [1980]. The transformed cells are then exposed to increased levels of methotrexate. This leads to the synthesis of multiple copies of the DHFR gene, and, concomitantly, multiple copies of other DNA comprising the expression vectors, such as the DNA encoding the target polypeptide. This amplification technique can be used with any otherwise suitable host, e.g., ATCC No. CCL61 CHO-K1, notwithstanding the presence of endogenous DHFR if, for example, a mutant DHFR gene that is highly resistant to Mtx is employed (EP 117,060). Alternatively, host cells (particularly wild-type hosts that contain endogenous DHFR) transformed or co-transformed with DNA sequences encoding the target polypeptide, wild-type DHFR protein, and another selectable marker such as aminoglycoside 3' phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., *Nature*, 282: 39 [1979]; Kingsman et al., *Gene*, 7: 141 [1979]; or Tschemper et al., *Gene*, 10: 157 [1980]). The trp1 gene provides a selection marker for a mutant strain of yeast lacking the ability to grow in tryptophan, for example, ATCC No. 44076 or PEP4-1 (Jones, *Genetics*, 8: 12 [1977]). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

(d) Promoter Component

Expression and cloning vectors usually contain a promoter that is recognized by the host organism and is operably linked to the target polypeptide nucleic acid. Promoters are untranslated sequences located upstream (5') to the start codon of a structural gene (generally within about 100 to 1000 bp) that control the transcription and translation of a particular nucleic acid sequence, such as that encoding the target polypeptide, to which they are operably linked. Such promoters typically fall into two classes, inducible and constitutive. Inducible promoters are promoters that initiate increased levels of transcription from DNA under their control in response to some change in culture conditions, e.g. the presence or absence of a nutrient or a change in temperature. At this time a large number of promoters recognized by a variety of potential host cells are well known. These promoters are operably linked to DNA encoding the target polypeptide by removing the promoter from the source DNA by restriction enzyme digestion and inserting the isolated promoter sequence into the vector. Both the native target polypeptide promoter sequence and many heterologous promoters may be used to direct amplification and/or expression of the target polypeptide DNA. However, heterologous promoters are preferred, as they generally permit greater transcription and higher yields of expressed target polypeptide as compared to the native target polypeptide promoter.

Promoters suitable for use with prokaryotic hosts include the β-lactamase and lactose promoter systems (Chang et al., *Nature*, 275: 615 [1978]; and Goeddel et al., *Nature*, 281: 544 [1979]), alkaline phosphatase, a tryptophan (trp) promoter system (Goeddel, *Nucleic Acids Res.*, 8: 4057 [1980] and EP 36,776) and hybrid promoters such as the tac promoter (deBoer et al., *Proc. Natl. Acad. Sci. USA*, 80: 21–25 [1983]). However, other known bacterial promoters are suitable. Their nucleotide sequences have been published, thereby enabling a skilled worker operably to ligate them to DNA encoding the target polypeptide (Siebenlist et al., *Cell*, 20: 269 [1980]) using linkers or adaptors to supply any required restriction sites. Promoters for use in bacterial systems also generally will contain a Shine-Dalgarno (S.D.) sequence operably linked to the DNA encoding the target polypeptide.

Suitable promoting sequences for use with yeast hosts include the promoters for 3-phosphoglycerate kinase (Hitzeman et al., *J. Biol. Chem.*, 255: 2073 [1980]) or other glycolytic enzymes (Hess et al., *J. Adv. Enzyme Reg.*, 7: 149 [1968]; and Holland, *Biochemistry*, 17:4900[1978]), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in Hitzeman et al., EP 73,657A. Yeast enhancers also are advantageously used with yeast promoters. Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence that may be the signal for addition of the poly A tail to the 3' end of the coding sequence. All of these sequences are suitably inserted into mammalian expression vectors.

Target polypeptide transcription from vectors in mammalian host cells is controlled by promoters obtained from the genomes of viruses such as polyoma virus, fowlpox virus (UK 2,211,504 published Jul. 5, 1989), adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g. the actin promoter or an immunoglobulin promoter, from heat-shock promoters, and from the promoter normally associated with the target polypeptide sequence, provided such promoters are compatible with the host cell systems.

The early and late promoters of the SV40 virus are conveniently obtained as an SV40 restriction fragment that also contains the SV40 viral origin of replication. Fiers et al., *Nature*, 273:113 (1978); Mulligan and Berg, *Science*, 2: 1422–1427 (1980); Pavlakis et al., *Proc. Natl. Acad. Sci. USA*, 78: 7398–7402 (1981). The immediate early promoter of the human cytomegalovirus is conveniently obtained as a HindIII E restriction fragment. Greenaway et al., *Gene*, 18: 355–360 (1982). A system for expressing DNA in mammalian hosts using the bovine papilloma virus as a vector is disclosed in U.S. Pat. No. 4,419,446. A modification of this system is described in U.S. Pat. No. 4,601,978. See also Gray et al., *Nature*, 295: 503–508 (1982) on expressing cDNA encoding immune interferon in monkey cells; , Reyes et al., *Nature*, 297: 598–601 (1982) on expression of human β-interferon cDNA in mouse cells under the control of a thymidine kinase promoter from herpes simplex virus, Canaani and Berg, *Proc. Natl. Acad. Sci. USA*, 79: 5166–5170 (1982) on expression of the human interferon β1 gene in cultured mouse and rabbit cells, and Gorman et al., *Proc. Natl. Acad. Sci. USA*, 79: 6777–6781 (1982) on expression of bacterial CAT sequences in CV-1 monkey kidney cells, chicken embryo fibroblasts, Chinese hamster ovary cells, HeLa cells, and mouse NIH-3T3 cells using the Rous sarcoma virus long terminal repeat as a promoter.

(e) Enhancer Element Component

Transcription of DNA encoding the target polypeptide of this invention by higher eukaryotes is often increased by inserting an enhancer sequence into the vector. Enhancers are cis-acting elements of DNA, usually about from 10–300 bp, that act on a promoter to increase its transcription. Enhancers are relatively orientation and position independent having been found 5' (Laimins et al., *Proc. Natl. Acad. Sci. USA*, 78: 993 [1981]) and 3' (Lusky et al., *Mol. Cell Bio.*, 3: 1108 [1983]) to the transcription unit, within an intron (Banerji et al., *Cell*, 33: 729 [1983]) as well as within the coding sequence itself (Osborne et al., *Mol. Cell Bio.*, 4: 1293 [1984]). Many enhancer sequences are now known from mammalian genes (globin, elastase, albumin, α-fetoprotein and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. See also Yaniv, *Nature*, 297: 17–18 (1982) on enhancing elements for activation of eukaryotic promoters. The enhancer may be spliced into the vector at a position 5' or 3' to the target polypeptide DNA, but is preferably located at a site 5' from the promoter.

(f) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3' untranslated regions of eukaryotic or viral DNA or cDNAs. These regions contain nucleotide segments transcribed as polyadenylated fragments in the untranslated portion of the mRNA encoding the target polypeptide. The 3' untranslated regions also include transcription termination sites.

Construction of suitable vectors containing one or more of the above listed components the desired coding and control sequences employs standard ligation techniques. Isolated plasmids or DNA fragments are cleaved, tailored, and religated in the form desired to generate the plasmids required.

For analysis to confirm correct sequences in plasmids constructed, the ligation mixtures are used to transform *E. coli* K12 strain 294 (ATCC 31,446) and successful transformants selected by ampicillin or tetracycline resistance where appropriate. Plasmids from the transformants are prepared, analyzed by restriction endonuclease digestion, and/or sequenced by the method of Messing et al., *Nucleic Acids Res.*, 9: 309 (1981) or by the method of Maxam et al., *Methods in Enzymology*, 65: 499 (1980).

Particularly useful in the practice of this invention are expression vectors that provide for the transient expression in mammalian cells of DNA encoding the target polypeptide. In general, transient expression involves the use of an expression vector that is able to replicate efficiently in a host cell, such that the host cell accumulates many copies of the expression vector and, in turn, synthesizes high levels of a desired polypeptide encoded by the expression vector. Transient expression systems, comprising a suitable expression vector and a host cell, allow for the convenient positive identification of polypeptides encoded by cloned DNAs, as well as for the rapid screening of such polypeptides for desired biological or physiological properties. Thus, transient expression systems are particularly useful in the invention for purposes of identifying analogs and variants of the target polypeptide that have target polypeptide-like activity.

Other methods, vectors, and host cells suitable for adaptation to the synthesis of the target polypeptide in recombinant vertebrate cell culture are described in Gething et al., Nature, 293: 620–625 [1981]; Mantei et al., Nature, 281: 4046 [1979]; Levinson et al.; EP 117,060; and EP 117,058. A particularly useful plasmid for mammalian cell culture expression of the target polypeptide is pRK5 (EP pub. no. 307,247) or pSVI6B.

Selection and Transformation of Host Cells

Suitable host cells for cloning or expressing the vectors herein are the prokaryote, yeast, or higher eukaryote cells described above. Suitable prokaryotes include eubacteria, such as Gram-negative or Gram-positive organisms, for example, E. coli, Bacilli such as B. subtilis, Pseudomonas species such as P. aeruginosa, Salmonella typhimurium, or Serratia marcescans. One preferred E. coli cloning host is E. coli 294 (ATCC 31,446), although other strains such as E. coli B, E. coli $\chi$1776 (ATCC 31,537), and E. coli W3110 (ATCC 27,325) are suitable. These examples are illustrative rather than limiting. Preferably the host cell should secrete minimal amounts of proteolytic enzymes. Alternatively, in vitro methods of cloning, e.g. PCR or other nucleic acid polymerase reactions, are suitable.

In addition to prokaryotes, eukaryotic microbes such as filamentous fungi or yeast are suitable hosts for target polypeptide-encoding vectors. Saccharomyces cerevisiae, or common baker's yeast, is the most commonly used among lower eukaryotic host microorganisms. However, a number of other genera, species, and strains are commonly available and useful herein, such as Schizosaccharomyces pombe [Beach and Nurse, Nature, 29: 140 (1981); EP 139,383 published May 2, 1985], Kluyveromyces hosts (U.S. Pat. No. 4,943,529) such as, e.g., K. lactis [Louvencourt et al., J. Bacteriol., 737 (1983)], K. fragilis, K. bulgaricus, K. thermotolerans, and K. marxianus, yarrowia [EP 402,226], Pichia pastoris [EP 183,070; Sreekrishna et al., J. Basic Microbiol., 28: 265–278 (1988)], Candida, Trichoderma reesia [EP 244,234], Neurospora crassa [Case et al., Proc. Natl. Acad. Sci. USA, 76: 5259–5263 (1979)], and filamentous fungi such as, e.g, Neurospora, Penicillium, Tolypocladium [WO 91/00357 published Jan. 10, 1991], and Aspergillus hosts such as A. nidulans [Ballance et al., Biochem. Biophys. Res. Commun., 112: 284–289 (1983); Tilburn et al., Gene, 26: 205–221 (1983); Yelton et al., Proc. Natl. Acad. Sci. USA, 81: 1470–1474 (1984)] and A. niger [Kelly and Hynes, EMBO J., 4: 475–479 (1985)].

Suitable host cells for the expression of glycosylated target polypeptide are derived from multicellular organisms. Such host cells are capable of complex processing and glycosylation activities. In principle, any higher eukaryotic cell culture is workable, whether from vertebrate or invertebrate culture. Examples of invertebrate cells include plant and insect cells. Numerous baculoviral strains and variants and corresponding permissive insect host cells from hosts such as Spodoptera frugiperda (caterpillar), Aedes aegypti (mosquito), Aedes albopictus (mosquito), Drosophila melanogaster (fruitfly), and Bombyx mori host cells have been identified. See, e.g., Luckow et al., Bio/Technology, 6: 47–55 (1988); Miller et al., in Genetic Engineering, Setlow, J. K. et al., eds., Vol. 8 (Plenum Publishing, 1986), pp. 277–279; and Maeda et al., Nature, 315: 592–594 (1985). A variety of such viral strains are publicly available, e.g., the L-1 variant of Autographa calfomica NPV and the Bm-5 strain of Bombyx mori NPV, and such viruses may be used as the virus herein according to the present invention, particularly for transfection of Spodoptera frugiperda cells. Plant cell cultures of cotton, corn, potato, soybean, petunia, tomato, and tobacco can be utilized as hosts. Typically, plant cells are transfected by incubation with certain strains of the bacterium Agrobacterium tumefaciens, which has been previously manipulated to contain the target polypeptide DNA. During incubation of the plant cell culture with A. tumefaciens, the DNA encoding target polypeptide is transferred to the plant cell host such that it is transfected, and will, under appropriate conditions, express the target polypeptide DNA. In addition, regulatory and signal sequences compatible with plant cells are available, such as the nopaline synthase promoter and polyadenylation signal sequences. Depicker et al., J. Mol. Appl. Gen., 1: 561 (1982). In addition, DNA segments isolated from the upstream region of the T-DNA 780 gene are capable of activating or increasing transcription levels of plant-expressible genes in recombinant DNA-containing plant tissue. See EP 321,196 published Jun. 21, 1989.

However, interest has been greatest in vertebrate cells, and propagation of vertebrate cells in culture (tissue culture) has become a routine procedure in recent years [Tissue Culture, Academic Press, Kruse and Patterson, editors (1973)]. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol., 36: 59 [1977]); baby hamster kidney cells (BHK, ATCC CCL 10); Chinese hamster ovary cells/-DHFR (CHO, Urlaub and Chasin, Proc. Natl. Acad. Sci. USA, 77: 4216 [1980]); mouse sertoli cells (TM4, Mather, Biol. Reprod., 23: 243–251 [1980]); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383: 44–68 [1982]); MRC 5 cells; FS4 cells; and a human hepatoma cell line (Hep G2). Preferred host cells are human embryonic kidney 293 and Chinese hamster ovary cells.

Host cells are transfected and preferably transformed with the above-described expression or cloning vectors of this invention and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, $CaPO_4$ and electroporation. Successful transfection is generally recognized when any indication of the operation of this vector occurs within the host cell.

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in section 1.82 of Sambrook et al., supra, is generally used for prokaryotes or other cells that contain substantial cell-wall barriers. Infection with *Agrobacterium tumefaciens* is used for transformation of certain plant cells, as described by Shaw et al., *Gene*, 23: 315 (1983) and WO 89/05859 published Jun. 29, 1989. For mammalian cells without such cell walls, the calcium phosphate precipitation method described in sections 16.30–16.37 of Sambrook et al., supra, is preferred. General aspects of mammalian cell host system transformations have been described by Axel in U.S. Pat. No. 4,399,216 issued Aug. 16, 1983. Transformations into yeast are typically carried out according to the method of Van Solingen et al., *J. Bact.*, 130: 946 (1977) and Hsiao et al., *Proc. Natl. Acad. Sci.* (*USA*), 76: 3829 (1979). However, other methods for introducing DNA into cells such as by nuclear injection, electroporation, or protoplast fusion may also be used.

Culturing the Host Cells

Prokaryotic cells used to produce the target polypeptide of this invention are cultured in suitable media as described generally in Sambrook et al., supra.

The mammalian host cells used to produce the target polypeptide of this invention may be cultured in a variety of media. Commercially available media such as Ham's F10 (Sigma), Minimal Essential Medium ([MEM], Sigma), RPMI-1640 (Sigma), and Dulbecco's Modified Eagle's Medium ([DMEM], Sigma) are suitable for culturing the host cells. In addition, any of the media described in Ham and Wallace, *Meth. Enz.*, 5: 44 (1979), Barnes and Sato, *Anal. Biochem.*, 102: 255 (1980), U.S. Pat. Nos. 4,767,704; 4,657,866; 4,927,762; or 4,560,655; WO 90/03430; WO 87/00195; U.S. Pat. Re. 30,985, may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

The host cells referred to in this disclosure encompass cells in in vitro culture as well as cells that are within a host animal.

It is further envisioned that the target polypeptides of this invention may be produced by homologous recombination, or with recombinant production methods utilizing control elements introduced into cells already containing DNA encoding the target polypeptide currently in use in the field. For example, a powerful promoter/enhancer element, a suppressor, or an exogenous transcription modulatory element is inserted in the genome of the intended host cell in proximity and orientation sufficient to influence the transcription of DNA encoding the desired target polypeptide. The control element does not encode the target polypeptide of this invention, but the DNA is present in the host cell genome. One next screens for cells making the target polypeptide of this invention, or increased or decreased levels of expression, as desired.

Detecting Gene Amplification/Expression

Gene amplification and/or expression may be measured in a sample directly, for example, by conventional Southern blotting, northern blotting to quantitate the transcription of mRNA (Thomas, *Proc. Natl. Acad. Sci. USA*, 77: 5201–5205 [1980]), dot blotting (DNA analysis), or in situ hybridization, using an appropriately labeled probe, based on the sequences provided herein. Various labels may be employed, most commonly radioisotopes, particularly $^{32}P$. However, other techniques may also be employed, such as using biotin-modified nucleotides for introduction into a polynucleotide. The biotin then serves as the site for binding to avidin or antibodies, which may be labeled with a wide variety of labels, such as radionuclides, fluorescers, enzymes, or the like. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of tissue sections and assay of cell culture or body fluids, to quantitate directly the expression of gene product. With immunohistochemical staining techniques, a cell sample is prepared, typically by dehydration and fixation, followed by reaction with labeled antibodies specific for the gene product coupled, where the labels are usually visually detectable, such as enzymatic labels, fluorescent labels, luminescent labels, and the like. A particularly sensitive staining technique suitable for use in the present invention is described by Hsu et al., *Am. J. Clin. Path.*, 75: 734–738 (1980).

Antibodies useful for immunohistochemical staining and/or assay of sample fluids may be either monoclonal or polyclonal, and may be prepared in any mammal. Conveniently, the antibodies may be prepared against a native target polypeptide or against a synthetic peptide based on the DNA sequences provided herein as described further in Section 4 below.

Purification of the Target Polypeptide

The target polypeptide preferably is recovered from the culture medium as a secreted polypeptide, although it also may be recovered from host cell lysates when directly expressed without a secretory signal.

When the target polypeptide is expressed in a recombinant cell other than one of human origin, the target polypeptide is completely free of proteins or polypeptides of human origin. However, it is necessary to purify the target polypeptide from recombinant cell proteins or polypeptides to obtain preparations that are substantially homogeneous as to the target polypeptide. As a first step, the culture medium or lysate is centrifuged to remove particulate cell debris. The membrane and soluble protein fractions are then separated. The target polypeptide may then be purified from the soluble protein fraction and from the membrane fraction of the culture lysate, depending on whether the target polypeptide is membrane bound. The following procedures are exemplary of suitable purification procedures: fractionation on immunoaffinity or ion-exchange columns; ethanol precipitation; reverse phase HPLC; chromatography on silica or on a cation exchange resin such as DEAE; chromatofocusing; SDS-PAGE; ammonium sulfate precipitation; gel filtration using, for example, Sephadex G-75; and protein A Sepharose columns to remove contaminants such as IgG.

Target polypeptide variants in which residues have been deleted, inserted or substituted are recovered in the same fashion, taking account of any substantial changes in properties occasioned by the variation. For example, preparation of a target polypeptide fusion with another protein or polypeptide, e.g. a bacterial or viral antigen, facilitates purification; an immunoaffinity column containing antibody to the antigen (or containing antigen, where the target polypeptide is an antibody) can be used to adsorb the fusion. Immunoaffinity columns such as a rabbit polyclonal anti-target polypeptide column can be employed to absorb the target polypeptide variant by binding it to at least one remaining immune epitope. A protease inhibitor such as phenyl methyl sulfonyl fluoride (PMSF) also may be useful to inhibit proteolytic degradation during purification, and antibiotics may be included to prevent the growth of adventitious contaminants. One skilled in the art will appreciate that purification methods suitable for native target polypeptide may require modification to account for changes in the character of the target polypeptide or its variants upon expression in recombinant cell culture.

Covalent Modifications of Target Polypeptides

Covalent modifications of target polypeptides are included within the scope of this invention. One type of covalent modification included within the scope of this invention is a target polypeptide fragment. Target polypeptide fragments having up to about 40 amino acid residues may be conveniently prepared by chemical synthesis, or by enzymatic or chemical cleavage of the full-length target polypeptide or variant target polypeptide. Other types of covalent modifications of the target polypeptide or fragments thereof are introduced into the molecule by reacting specific amino acid residues of the target polypeptide or fragments thereof with an organic derivatizing agent that is capable of reacting with selected side chains or the N- or C-terminal residues.

Cysteinyl residues most commonly are reacted with o-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5–7.0 because this agent is relatively specific for the histidyl side chain. Para-bromophenacyl bromide also is useful; the reaction is preferably performed in 0.1 M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay, the chloramine T method described above being suitable.

Carboxyl side groups (aspartyl or glutamyl) are selectively modified by reaction with carbodiimides (R'—N=C=N—R'), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking target polypeptide to a water-insoluble support matrix or surface for use in the method for purifying anti-target polypeptide antibodies, and vice versa. Commonly used crosslinking agents include, e.g., 1,1-bis (diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidylpropionate), and bifunctional maleimides such as bis-N-maleimido-1,8-octane. Derivatizing agents such as methyl-3-[(p-azidophenyl)dithio]propioimidate yield photo-activatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues, respectively. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, *Proteins: Structure and Molecular ProDerties*, W.H. Freeman & Co., San Francisco, pp. 79–86 [1983]), acetylation of the N-terminal amine, and amidation of any C-terminal carboxyl group.

Another type of covalent modification of the target polypeptide included within the scope of this invention comprises altering the native glycosylation pattern of the polypeptide. By altering is meant deleting one or more carbohydrate moieties found in the native target polypeptide, and/or adding one or more glycosylation sites that are not present in the native target polypeptide.

Glycosylation of polypeptides is typically either N-linked or O-linked. N-linked refers to the attachment of the carbohydrate moiety to the side chain of an asparagine residue. The tri-peptide sequences asparagine-X-serine and asparagine-X-threonine, where X is any amino acid except proline, are the recognition sequences for enzymatic attachment of the carbohydrate moiety to the asparagine side chain. Thus, the presence of either of these tri-peptide sequences in a polypeptide creates a potential glycosylation site. O-linked glycosylation refers to the attachment of one of the sugars N-acetylgalactosamine, galactose, or xylose, to a hydroxyamino acid, most commonly serine or threonine, although 5-hydroxyproline or 5-hydroxylysine may also be used.

Addition of glycosylation sites to the target polypeptide is conveniently accomplished by altering the amino acid sequence such that it contains one or more of the above-described tri-peptide sequences (for N-linked glycosylation sites). The alteration may also be made by the addition of, or substitution by, one or more serine or threonine residues to the native target polypeptide sequence (for O-linked glycosylation sites). For ease, the target polypeptide amino acid sequence is preferably altered through changes at the DNA level, particularly by mutating the DNA encoding the target polypeptide at preselected bases such that codons are generated that will translate into the desired amino acids. The DNA mutation(s) may be made using methods described above under the heading of "Amino Acid Sequence Variants of Target Polypeptide".

Another means of increasing the number of carbohydrate moieties on the target polypeptide is by chemical or enzymatic coupling of glycosides to the polypeptide. These procedures are advantageous in that they do not require production of the polypeptide in a host cell that has glycosylation capabilities for N- and O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 published Sep. 11, 1987, and in Aplin and Wriston (*CRC Crit. Rev. Biochem.*, pp. 259–306 [1981]).

Removal of carbohydrate moieties present on the native target polypeptide may be accomplished chemically or enzymatically. Chemical deglycosylation requires exposure of the polypeptide to the compound trifluoromethanesulfonic acid, or an equivalent compound. This treatment results in the cleavage of most or, all sugars except the linking sugar (N-acetylglucosamine or N-acetylgalactosamine), while leaving the polypeptide intact. Chemical deglycosylation is described by Hakimuddin et al. (*Arch. Biochem. Bioohys.*, 259:52 [1987]) and by Edge et al. (*Anal. Biochem.*, 118:131 [1981]). Enzymatic cleavage of carbohydrate moieties on polypeptides can be achieved by the use of a variety of endo- and exo-glycosidases as described by Thotakura et al. (*Meth. Enzymol.*, 138:350 [1987]).

Glycosylation at potential glycosylation sites may be prevented by the use of the compound tunicamycin as described by Duskin et al. (*J. Biol. Chem.*, 257:3105 [1982]). Tunicamycin blocks the formation of protein-N-glycoside linkages.

Another type of covalent modification of the target polypeptide comprises linking the target polypeptide to various nonproteinaceous polymers, e.g. polyethylene glycol, polypropylene glycol or polyoxyalkylenes, in the manner set forth in U.S. Pat. Nos. 4,640,835; 4,496,689; 4,301,144; 4,670,417; 4,791,192 or 4,179,337.

The target polypeptide also may be entrapped in microcapsules prepared, for example, by coacervation techniques or by interfacial polymerization (for example, hydroxymethylcellulose or gelatin-microcapsules and poly-[methylmethacylate]microcapsules, respectively), in colloidal drug delivery systems (for example, liposomes, albumin microspheres, microemulsions, nano-particles and nanocapsules), or in macroemulsions. Such techniques are disclosed in *Reminaton's Pharmaceutical Sciences*, 16th edition, Osol, A., Ed., (1980).

Target polypeptide preparations are also useful in generating antibodies, for screening for binding partners, as standards in assays for the target polypeptide (e.g. by labeling the target polypeptide for use as a standard in a radioimmunoassay, enzyme-linked immunoassay, or radioreceptor assay), in affinity purification techniques, and in competitive-type receptor binding assays when labeled with radioiodine, enzymes, fluorophores, spin labels, and the like.

Since it is often difficult to predict in advance the characteristics of a variant target polypeptide, it will be appreciated that some screening of the recovered variant will be needed to select the optimal variant. For example, a change in the immunological character of the target polypeptide molecule, such as affinity for a given antigen or antibody, is measured by a competitive-type immunoassay. The variant is assayed for changes in the suppression or enhancement of its activity by comparison to the activity observed for the target polypeptide in the same assay. Other potential modifications of protein or polypeptide properties such as redox or thermal stability, hydrophobicity, susceptibility to proteolytic degradation, stability in recombinant cell culture or in plasma, or the tendency to aggregate with carriers or into multimers are assayed by methods well known in the art.

Diagnostic and Related Uses of the Antibodies

The antibodies of this invention are useful in diagnostic assays for antigen expression in specific cells or tissues. The antibodies are detectably labeled and/or are immobilized on an insoluble matrix.

The antibodies of this invention find further use for the affinity purification of the antigen from recombinant cell culture or natural sources. Suitable diagnostic assays for the antigen and its antibodies depend on the particular antigen or antibody. Generally, such assays include competitive and sandwich assays, and steric inhibition assays. Competitive and sandwich methods employ a phase-separation step as an integral part of the method while steric inhibition assays are conducted in a single reaction mixture. Fundamentally, the same procedures are used for the assay of the antigen and for substances that bind the antigen, although certain methods will be favored depending upon the molecular weight of the substance being assayed. Therefore, the substance to be tested is referred to herein as an analyte, irrespective of its status otherwise as an antigen or antibody, and proteins that bind to the analyte are denominated binding partners, whether they be antibodies, cell surface receptors, or antigens.

Analytical methods for the antigen or its antibodies all use one or more of the following reagents: labeled analyte analogue, immobilized analyte analogue, labeled binding partner, immobilized binding partner and steric conjugates. The labeled reagents also are known as "tracers."

The label used (and this is also useful to label antigen nucleic acid for use as a probe) is any detectable functionality that does not interfere with the binding of analyte and its binding partner. Numerous labels are known for use in immunoassay, examples including moieties that may be detected directly, such as fluorochrome, chemiluminescent, and radioactive labels, as well as moieties, such as enzymes, that must be reacted or derivatized to be detected. Examples of such labels include the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

Conventional methods are available to bind these labels covalently to proteins or polypeptides. For instance, coupling agents such as dialdehydes, carbodiimides, dimaleimides, bis-imidates, bis-diazotized benzidine, and the like may be used to tag the antibodies with the above-described fluorescent, chemiluminescent, and enzyme labels. See, for example, U.S. Pat. No. 3,940,475 (fluorimetry) and U.S. Pat. No. 3,645,090 (enzymes); Hunter et al., *Nature*, 144: 945 (1962); David et al., *Biochemistry*, 13: 1014–1021 (1974); Pain et al., *J. Immunol. Methods*, 40: 219–230 (1981); and Nygren, *J. Histochem. and Cytochem.*, 30: 407–412 (1982). Preferred labels herein are enzymes such as horseradish peroxidase and alkaline phosphatase.

The conjugation of such label, including the enzymes, to the antibody is a standard manipulative procedure for one of ordinary skill in immunoassay techniques. See, for example, O'Sullivan et al., "Methods for the Preparation of Enzyme-antibody Conjugates for Use in Enzyme Immunoassay," in *Methods in Enzymology*, ed. J. J. Langone and H. Van Vunakis, Vol. 73 (Academic Press, New York, N.Y., 1981), pp. 147–166. Such bonding methods are suitable for use with the antibodies and polypeptides of this invention.

Immobilization of reagents is required for certain assay methods. Immobilization entails separating the binding partner from any analyte that remains free in solution. This conventionally is accomplished by either insolubilizing the binding partner or analyte analogue before the assay procedure, as by adsorption to a water-insoluble matrix or surface (Bennich et al., U.S. Pat. No. 3,720,760), by covalent coupling (for example, using glutaraldehyde cross-linking), or by insolubilizing the partner or analogue afterward, e.g., by immunoprecipitation.

Other assay methods, known as competitive or sandwich assays, are well established and widely used in the commercial diagnostics industry.

Competitive assays rely on the ability of a tracer analogue to compete with the test sample analyte for a limited number of binding sites on a common binding partner. The binding partner generally is insolubilized before or after the competition and then the tracer and analyte bound to the binding partner are separated from the unbound tracer and analyte. This separation is accomplished by decanting (where the binding partner was preinsolubilized) or by centrifuging (where the binding partner was precipitated after the competitive reaction). The amount of test sample analyte is inversely proportional to the amount of bound tracer as measured by the amount of marker substance. Dose-response curves with known amounts of analyte are prepared and compared with the test results to quantitatively determine the amount of analyte present in the test sample. These assays are called ELISA systems when enzymes are used as the detectable markers.

Another species of competitive assay, called a "homogeneous" assay, does not require a phase separation. Here, a conjugate of an enzyme with the analyte is prepared and used such that when anti-analyte binds to the analyte the presence of the anti-analyte modifies the enzyme activity. In this case, the antigen or its immunologically active fragments are conjugated with a bifunctional organic bridge to an enzyme such as peroxidase. Conjugates are selected for use with antibody so that binding of the antibody inhibits or potentiates the enzyme activity of the label. This method per se is widely practiced under the name of EMIT.

Steric conjugates are used in steric hindrance methods for homogeneous assay. These conjugates are synthesized by covalently linking a low-molecular-weight hapten to a small analyte so that antibody to hapten substantially is unable to bind the conjugate at the same time as anti-analyte. Under this assay procedure the analyte present in the test sample will bind anti-analyte, thereby allowing anti-hapten to bind the conjugate, resulting in a change in the character of the conjugate hapten, e.g., a change in fluorescence when the hapten is a fluorophore.

Sandwich assays particularly are useful for the determination of antigen or antibodies. In sequential sandwich assays an immobilized binding partner is used to adsorb test sample analyte, the test sample is removed as by washing, the bound analyte is used to adsorb labeled binding partner, and bound material is then separated from residual tracer. The amount of bound tracer is directly proportional to test sample analyte. In "simultaneous" sandwich assays the test sample is not separated before adding the labeled binding partner. A sequential sandwich assay using an anti-antigen monoclonal antibody as one antibody and a polyclonal anti-antigen antibody as the other is useful in testing samples for particular antigen activity.

The foregoing are merely exemplary diagnostic assays for the import and humanized antibodies of this invention. Other methods now or hereafter developed for the determination of these analytes are included within the scope hereof, including the bioassays described above.

Immunotoxins

This invention is also directed to immunochemical derivatives of the antibodies of this invention such as immunotoxins (conjugates of the antibody and a cytotoxic moiety). Antibodies which carry the appropriate effector functions, such as with their constant domains, are also used to induce lysis through the natural complement process, and to interact with antibody dependent cytotoxic cells normally present.

For example, purified, sterile filtered antibodies are optionally conjugated to a cytotoxin such as ricin for use in AIDS therapy. U.S. patent application Ser. No. 07/350,895 illustrates methods for making and using immunotoxins for the treatment of HIV infection. The methods of this invention, for example, are suitable for obtaining humanized antibodies for use as immunotoxins for use in AIDS therapy.

The cytotoxic moiety of the immunotoxin may be a cytotoxic drug or an enzymatically active toxin of bacterial, fungal, plant or animal origin, or an enzymatically active-fragment of such a toxin. Enzymatically active toxins and fragments thereof used are diphtheria A chain, nonbinding active fragments of diphtheria toxin, exotoxin A chain (from *Pseudomonas aeruginosa*), ricin A chain, abrin A chain, modeccin A chain, alpha-sarcin, *Aieurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin and the tricothecenes. In another embodiment, the antibodies are conjugated to small molecule anticancer drugs such as cis-platin or 5FU. Conjugates of the monoclonal antibody and such cytotoxic moieties are made using a variety of bifunctional protein coupling agents. Examples of such reagents are SPDP, IT, bifunctional derivatives of imidoesters such as dimethyl adipimidate HCl, active esters such as disuccinimidyl suberate, aldehydes such as glutaraldehyde, bis-azido compounds such as bis (p-azidobenzoyl) hexanediamine, bis-diazonium derivatives such as bis-(p-diazoniumbenzoyl)-ethylenediamine, diisocyanates such as tolylene 2,6-diisocyanate and bis-active fluorine compounds such as 1,5-difluoro-2,4-dinitrobenzene. The lysing portion of a toxin may be joined to the Fab fragment of the antibodies.

Immunotoxins can be made in a variety of ways, as discussed herein. Commonly known crosslinking reagents can be used to yield stable conjugates.

Advantageously, monoclonal antibodies specifically binding the domain of the antigen which is exposed on the infected cell surface, are conjugated to ricin A chain. Most advantageously the ricin A chain is deglycosylated and produced through recombinant means. An advantageous method of making the ricin immunotoxin is described in Vitetta et al., *Science* 238:1098 (1987).

When used to kill infected human cells in vitro for diagnostic purposes, the conjugates will typically be added to the cell culture medium at a concentration of at least about 10 nM. The formulation and mode of administration for in vitro use are not critical. Aqueous formulations that are compatible with the culture or perfusion medium will normally be used. Cytotoxicity may be read by conventional techniques.

Cytotoxic radiopharmaceuticals for treating infected cells may be made by conjugating radioactive isotopes (e.g. I, Y. Pr) to the antibodies. Advantageously alpha particle-emitting isotopes are used. The term "cytotoxic moiety" as used herein is intended to include such isotopes.

In a preferred embodiment, ricin A chain is deglycosylated or produced without oligosaccharides, to decrease its clearance by irrelevant clearance mechanisms (e.g., the liver). In another embodiment, whole ricin (A chain plus B chain) is conjugated to antibody if the galactose binding property of B-chain can be blocked ("blocked ricin").

In a further embodiment toxin-conjugates are made with Fab or F(ab')$_2$ fragments. Because of their relatively small size these fragments can better penetrate tissue to reach infected cells.

In another embodiment, fusogenic liposomes are filled with a cytotoxic drug and the liposomes are coated with antibodies specifically binding the particular antigen.

Antibody Dependent Cellular Cytotoxicity

Certain aspects of this invention involve antibodies which are (a) directed against a particular antigen and (b) belong to a subclass or isotype that is capable of mediating the lysis of cells to which the antibody molecule binds. More specifically, these antibodies should belong to a subclass or isotype that, upon complexing with cell surface proteins, activates serum complement and/or mediates antibody dependent cellular cytotoxicity (ADCC) by activating effector cells such as natural killer cells or macrophages.

Biological activity of antibodies is known to be determined, to a large extent, by the constant domains or Fc region of the antibody molecule (Uananue and Benacerraf, *Textbook of Immunology*, 2nd Edition, Williams & Wilkins, p. 218 (1984)). This includes their ability to activate complement and to mediate antibody-dependent cellular cytotoxicity (ADCC) as effected by leukocytes. Antibodies of different classes and subclasses differ in this respect, as do antibodies from the same subclass but different species; according to the present invention, antibodies of those classes having the desired biological activity are prepared. Preparation of these antibodies involves the selection of antibody constant domains are their incorporation in the humanized antibody by known technique. For example, mouse immunoglobulins of the IgG3 and IgG2a class are capable of activating serum complement upon binding to the target cells which express the cognate antigen, and therefore humanized antibodies which incorporate IgG3 and IgG2a effector functions are desirable for certain therapeutic applications.

In general, mouse antibodies of the IgG2a and IgG3 subclass and occasionally IgG1 can mediate ADCC, and antibodies of the IgG3, IgG2a, and IgM subclasses bind and activate serum complement. Complement activation generally requires the binding of at least two IgG molecules in close proximity on the target cell. However, the binding of only one IgM molecule activates serum complement.

The ability of any particular antibody to mediate lysis of the target cell by complement activation and/or ADCC can be assayed. The cells of interest are grown and labeled in vitro; the antibody is added to the cell culture in combination with either serum complement or immune cells which may be activated by the antigen antibody complexes. Cytolysis of the target cells is detected by the release of label from the lysed cells. In fact, antibodies can be screened using the patient's own serum as a source of complement and/or immune cells. The antibody that is capable of activating complement or mediating ADCC in the in vitro test can then be used therapeutically in that particular patient.

This invention specifically encompasses consensus Fc antibody domains prepared and used according to the teachings of this invention.

Therapeutic and Other Uses of the Antibodies

When used in vivo for therapy, the antibodies of the subject invention are administered to the patient in therapeutically effective amounts (i.e. amounts that have desired therapeutic effect). They will normally be administered parenterally. The dose and dosage regimen will depend upon the degree of the infection, the characteristics of the particular antibody or immunotoxin used, e.g., its therapeutic index, the patient, and the patient's history. Advantageously the antibody or immunotoxin is administered continuously over a period of 1–2 weeks, intravenously to treat cells in the vasculature and subcutaneously and intraperitoneally to treat regional lymph nodes. Optionally, the administration is made during the course of adjunct therapy such as combined cycles of radiation, chemotherapeutic treatment, or administration of tumor necrosis factor, interferon or other cytoprotective or immunomodulatory agent.

For parenteral administration the antibodies will be formulated in a unit dosage injectable form (solution, suspension, emulsion) in association with a pharmaceutically acceptable parenteral vehicle. Such vehicles are inherently nontoxic, and non-therapeutic. Examples of such vehicles are water, saline, Ringer's solution, dextrose solution, and 5% human serum albumin. Nonaqueous vehicles such as fixed oils and ethyl oleate can also be used. Liposomes may be used as carriers. The vehicle may contain minor amounts of additives such as substances that enhance isotonicity and chemical stability, e.g., buffers and preservatives. The antibodies will typically be formulated in such vehicles at concentrations of about 1 mg/ml to 10 mg/ml.

Use of IgM antibodies may be preferred for certain applications, however IgG molecules by being smaller may be more able than IgM molecules to localize to certain types of infected cells.

There is evidence that complement activation in vivo leads to a variety of biological effects, including the induction of an inflammatory response and the activation of macrophages (Uananue and Benecerraf, *Textbook of Immunology*, 2nd Edition, Williams & Wilkins, p. 218 (1984)). The increased vasodilation accompanying inflammation may increase the ability of various agents to localize in infected cells. Therefore, antigen-antibody combinations of the type specified by this invention can be used therapeutically in many ways. Additionally, purified antigens (Hakomori, *Ann. Rev. Immunol.* 2:103 (1984)) or anti-idiotypic antibodies (Nepom et al., *Proc. Natl. Acad. Sci.* 81:2864 (1985); Koprowski et al., *Proc. Natl. Acad. Sci.* 81:216 (1984)) relating to such antigens could be used to induce an active immune response in human patients. Such a response includes the formation of antibodies capable of activating human complement and mediating ADCC and by such mechanisms cause infected cell destruction.

Optionally, the antibodies of this invention are useful in passively immunizing patients, as exemplified by the administration of humanized anti-HIV antibodies.

The antibody compositions used in therapy are formulated and dosages established in a fashion consistent with good medical practice taking into account the disorder to be treated, the condition of the individual patient, the site of delivery of the composition, the method of administration and other factors known to practitioners. The antibody compositions are prepared for administration according to the description of preparation of polypeptides for administration, infra.

Deposit of Materials

As described above, cultures of the muMAb4D5 have been deposited with the American Type Culture Collection, 10801 University Blud., Manassas, Va. USA (ATCC).

This deposit was made under the provisions of the Budapest Treaty on the International Recognition of the Deposit of Microorganisms for the Purpose of Patent Procedure and the Regulations thereunder (Budapest Treaty). This assures maintenance of viable cultures for 30 years from the date of the deposit. The organisms will be made available by ATCC under the terms of the Budapest Treaty, and subject to an agreement between Genentech, Inc. and ATCC, which assures permanent and unrestricted availability of the progeny of the cultures to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.12 with particular reference to 886 OG 638).

In respect of those designations in which a European patent is sought, a sample of the deposited microorganism will be made available until the publication of the mention of the grant of the European patent or until the date on which the application has been refused or withdrawn or is deemed to be withdrawn, only by the issue of such a sample to an expert nominated by the person requesting the sample. (Rule 28(4) EPC)

The assignee of the present application has agreed that if the cultures on deposit should die or be lost or destroyed when cultivated under suitable conditions, they will be promptly replaced on notification with a viable specimen of the same culture. Availability of the deposited strain is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the constructs deposited, since the deposited embodiments are intended to illustrate only certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that they represent. Indeed, various modifications of the invention in addition to those shown and described herein will become apparent to those skilled in the art from the foregoing description and fall within the scope of the appended claims.

It is understood that the application of the teachings of the present invention to a specific problem or situation will be within the capabilities of one having ordinary skill in the art in light of the teachings contained herein. Examples of the products of the present invention and representative processes for their isolation, use, and manufacture appear below, but should not be construed to limit the invention.

EXAMPLES

Example 1

Humanization of muMAb4D5

Here we report the chimerization of muMAb4D5 (chMAb4D5) and the rapid and simultaneous humanization of heavy ($V_H$) and light ($V_L$) chain variable region genes using a novel "gene conversion mutagenesis" strategy. Eight humanized variants (huMAb4D5) were constructed to probe the importance of several FR residues identified by our molecular modeling or previously proposed to be critical to the conformation of particular CDRs (see Chothia, C. & Lesk, A. M., *J. Mol. Biol.* 196:901–917 (1987); Chothia, C. et al., *Nature* 342:877–883 (1989); Tramontano, A. et al., *J. Mol. Biol.* 215:175–182 (1990)). Efficient transient expression of humanized variants in non-myeloma cells allowed us to rapidly investigate the relationship between binding affinity for p185$^{HER2}$ ECD and anti-proliferative activity against p185$^{HER2}$ overexpressing carcinoma cells.

MATERIALS and METHODS

Cloning of Variable Region Genes. The muMAb4D5 $V_H$ and $V_L$ genes were isolated by polymerase chain reaction (PCR) amplification of mRNA from the corresponding hybridoma (Fendly, B. M. et al., *Cancer Res.* 50:1550–1558 (1990)) as described by Orlandi et al. (Orlandi, R. et al., *Proc. Natl. Acad. Sci. USA* 86:3833–3837 (1989)). Amino terminal sequencing of muMAb4D5 $V_L$ and $V_H$ was used to design the sense strand PCR primers, whereas the anti-sense PCR primers were based upon consensus sequences of murine framework residues (Orlandi, R. et al., *Proc. Natl Acad. Sci. USA* 86:3833–3837 (1989); Kabat, E. A. et al., *Sequences of Proteins of Immunological Interest* (National Institutes of Health, Bethesda, Md., 1987)) incorporating restriction sites for directional cloning shown by underlining and listed after the sequences: $V_L$ sense, 5'-TCC GATATCCAGCTGACCCAGTCTCCA-3' (SEQ. ID NO. 7), EcoRV; $V_L$ anti-sense, 5'-GTTTGATCTCCAGCTT GGTACCHSCDCCGAA-3' (SEQ. ID NO. 8), Asp718; $V_H$ sense, 5'-AGGTSMARCTGCAGSAGTCWGG-3' (SEQ. ID NO. 9), PstI and $V_H$ anti-sense, 5'-TGAGGAGAC GGTGACCGTGGTCCCTTGGCCCCAG-3' (SEQ. ID NO. 10), BstEII; where H=A or C or T, S=C or G, D=A or G or T, M=A or C, R=A or G and W=A or T. The PCR products were cloned into pUC119 (Vieira, J. & Messing, J., *Methods Enzymol.* 153:3–11 (1987)) and five clones for each variable domain sequenced by the dideoxy method (Sanger, F. et al., *Proc. Natl. Acad. Sci. USA* 74:5463–5467 (1977)).

Molecular Modelling. Models for muMAb4D5 $V_H$ and $V_L$ domains were constructed separately from consensus coordinates based upon seven Fab structures from the Brookhaven protein data bank (entries 1FB4, 2RHE, 2MCP, 3FAB, 1FBJ, 2HFL and 1REI). The Fab fragment KOL (Marquart, M. et al., *J. Mol. Biol.* 141:369–391 (1980)) was first chosen as a template for $V_L$ and $V_H$ domains and additional structures were then superimposed upon this structure using their main chain atom coordinates (INSIGHT program, Biosym Technologies). The distance from the template C$\alpha$ to the analogous C$\alpha$ each of the superimposed structures was calculated for each residue position. If all (or nearly all) C$\alpha$-C$\alpha$ distances for a given residue were $\leq 1$ Å, then that position was included in the consensus structure. In most cases the $\beta$-sheet framework residues satisfied these criteria whereas the CDR loops did not. For each of these selected residues the average coordinates for individual N, C$\alpha$, C, O and C$\beta$ atoms were calculated and then corrected for resultant deviations from non-standard bond geometry by 50 cycles of energy minimization using the DISCOVER program (Biosym Technologies) with the AMBER forcefield (Weiner, S. J. et al., *J. Amer. Chem. Soc.* 106:765–784 (1984)) and C$\alpha$ coordinates fixed. The side chains of highly conserved residues, such as the disulfide-bridged cysteine residues, were then incorporated into the resultant consensus structure. Next the sequences of muMAb4D5 $V_L$ and $V_H$ were incorporated starting with the CDR residues and using the tabulations of CDR conformations from Chothia et al. (Chothia, C. et al., *Nature* 342:877–883 (1989)) as a guide. Side-chain conformations were chosen on the basis of Fab crystal structures, rotamer libraries (Ponder, J. W. & Richards, F. M., *J. Mol. Biol.* 193:775–791 (1987)) and packing considerations. Since $V_H$-CDR3 could not be assigned a definite backbone conformation from these criteria, two models were created from a search of similar sized loops using the INSIGHT program. A third model was derived using packing and solvent exposure considerations. Each model was then subjected to 5000 cycles of energy minimization.

In humanizing muMAb4D5, consensus human sequences were first derived from the most abundant subclasses in the sequence compilation of Kabat et al. (Kabat, E. A. et al., *Sequences of Proteins of Immunological Interest* (National Institutes of Health, Bethesda, Md., 1987)), namely $V_L$ $\kappa$ subgroup I and $V_H$ group III, and a molecular model generated for these sequences using the methods described above. A structure for huMAb4D5 was created by transferring the CDRs from the muMAb4D5 model into the consensus human structure. All huMAb4D5 variants contain human replacements of muMAb4D5 residues at three positions within CDRs as defined by sequence variability (Kabat, E. A. et al., *Sequences of Proteins of Immunological Interest* (National Institutes of Health, Bethesda, Md., 1987)) but not as defined by structural variability (Chothia, C. & Lesk, A. M., *J. Mol. Biol.* 196:901–917 (1987)): $V_L$-CDR1 K24R, $V_L$-CDR2 R54L and $V_L$-CDR2 T56S. Differences between muMAb4D5 and the human consensus framework residues (FIG. 1) were individually modeled to investigate their possible influence on CDR conformation and/or binding to the p185$^{HER2}$ ECD.

Construction of Chimeric Genes. Genes encoding chMAb4D5 light and heavy chains were separately assembled in previously described phagemid vectors containing the human cytomegalovirus enhancer and promoter, a 5' intron and SV40 polyadenylation signal (Gorman, C. M. et al., *DNA & Prot. Engin. Tech.* 2:3–10 (1990)). Briefly, gene segments encoding muMAb4D5 $V_L$ (FIG. 1A) and REI human $\kappa_1$ light chain $C_L$ (Palm, W. & Hilschmann, N., Z. *Physiol. Chem.* 356:167–191 (1975)) were precisely joined as were genes for muMAb4D5 $V_H$ (FIG. 1B) and human $\gamma$1 constant region (Capon, D. J. et al., *Nature* 337:525–531 (1989)) by simple subcloning (Boyle, A., in *Current Protocols in Molecular Biology*, Chapter 3 (F. A. Ausubel et al., eds., Greene Publishing & Wiley-Interscience, New York, 1990)) and site-directed mutagenesis (Carter, P., in *Mutagenesis: A Practical Approach*, Chapter 1 (IRL Press, Oxford, UK 1991)) The $\gamma$1 isotype was chosen as it has been found to be the preferred human isotype for supporting ADCC and complement dependent cytotoxicity using matched sets of chimeric (Brüggemann, M. et al., *J. Exp. Med.* 166:1351–1361 (1987)) or humanized antibodies (Riechmann L. et al., *Nature* 332:323–327 (1988)). The PCR-generated $V_L$ and $V_H$ fragments (FIG. 1) were subsequently mutagenized so that they faithfully represent the sequence of muMAb4D5 determined at the protein level: $V_H$ Q1E, $V_L$ V104L and T109A (variants are denoted by the amino acid residue and number followed by the replacement amino acid). The human $\gamma$1 constant regions are identical to those reported by Ellison et al. (Ellison, J. W. et al., *Nucleic Acids Res.* 13:4071–4079 (1982)) except for the mutations E359D and M361L (Eu numbering, as in Kabat, E. A. et al., *Sequences of Proteins of Immunological Interest* (National Institutes of Health, Bethesda, Md., 1987)) which we installed to convert the antibody from the naturally rare A allotype to the much more common non-A allotype (Tramontano, A. et al., *J. Mol. Biol.* 215:175–182 (1990)). This was an attempt to reduce the risk of anti-allotype antibodies interfering with therapy.

Construction of Humanized Genes. Genes encoding chMAb4D5 light chain and heavy chain Fd fragment ($V_H$ and $C_H$1 domains) were subcloned together into pUC119 (Vieira, J. & Messing, J., *Methods Enzymo.* 153:3–11 (1987)) to create pAK1 and simultaneously humanized in a single step (FIG. 2). Briefly, sets of 6 contiguous oligonucleotides were designed to humanize $V_H$ and $V_L$ (FIG. 1). These oligonucleotides are 28 to 83 nucleotides in length, contain zero to 19 mismatches to the murine antibody template and are constrained to have 8 or 9 perfectly matched residues at each end to promote efficient annealing and ligation of adjacent oligonucleotides. The sets of $V_H$ and $V_L$ humanization oligonucleotides (5 pmol each) were phosphorylated with either ATP or γ-$^{32}$P-ATP (Carter, P. *Methods Enzymol.* 154:382–403 (1987)) and separately annealed with 3.7 pmol of pAK1 template in 40 μl 10 mM Tris-HCl (pH 8.0) and 10 mM MgCl$_2$ by cooling from 100° C. to room temperature over ~30 min. The annealed oligonucleotides were joined by incubation with T4 DNA ligase (12 units; New England Biolabs) in the presence of 2 μl 5 mM ATP and 2 μl 0.1 M DTT for 10 min at 14° C. After electrophoresis on a 6% acrylamide sequencing gel the assembled oligonucleotides were located by autoradiography and recovered by electroelution. The assembled oligonucleotides (~0.3 pmol each) were simultaneously annealed to 0.15 pmol single-stranded deoxyuridine-containing pAK1 prepared according to Kunkel et al. (Kunkel, T. A. et al., *Methods Enzymol.* 154:367–382 (1987)) in 10 μl 40 mM Tris-HCl (pH 7.5) and 16 mM MgCl$_2$ as above. Heteroduplex DNA was constructed by extending the primers with T7 DNA polymerase and transformed into *E. coli* BMH 71-18 mutL as previously described (Carter, P., in *Mutagenesis: A Practical Approach*, Chapter 1 (IRL Press, Oxford, UK 1991)). The resultant phagemid DNA pool was enriched first for hu$V_L$ by restriction purification using XhoI and then for hu$V_H$ by restriction selection using StuI as described in Carter, P., in *Mutagenesis: A Practical Approach*, Chapter 1 (IRL Press, Oxford, UK 1991); and in Wells, J. A. et al., *Phil. Trans. R. Soc. Lond. A* 317:415–423 (1986). Resultant clones containing both hu$V_L$ and hu$V_H$ genes were identified by nucleotide sequencing (Sanger, F. et al., *Proc. Natl. Acad. Sci. USA* 74:5463–5467 (1977)) and designated pAK2. Additional humanized variants were generated by site-directed mutagenesis (Carter, P., in *Mutagenesis: A Practical Approach*, Chapter 1 (IRL Press, Oxford, UK 1991)). The muMAb4D5 $V_L$ and $V_H$ gene segments in the transient expression vectors described above were then precisely replaced with their humanized versions.

Expression and Purification of MAb4D5 Variants. Appropriate MAb4D5 light and heavy chain cDNA expression vectors were co-transfected into an adenovirus transformed human embryonic kidney cell line, 293 (Graham, F. L. et al., *J. Gen. virol.* 36:59–72 (1977)) using a high efficiency procedure (Gorman, C. M. et al., *DNA & Prot. Engin. Tech.* 2:3–10 (1990); Gorman, C., in *DNA Cloning*, vol II, pp 143–190 (D. M. Glover, ed., IRL Press, Oxford, UK 1985)). Media were harvested daily for up to 5 days and the cells re-fed with serum free media. Antibodies were recovered from the media and affinity purified on protein A sepharose CL-4B (Pharmacia) as described by the manufacturer. The eluted antibody was buffer-exchanged into phosphate-buffered saline by G25 gel filtration, concentrated by ultra-filtration (Centriprep-30 or Centricon-100, Amicon), sterile-filtered (Millex-GV, Millipore) and stored at 4° C. The concentration of antibody was determined by using both total immunoglobulin and antigen binding ELISAs. The standard used was huMAb4D5-5, whose concentration had been determined by amino acid composition analysis.

Cell Proliferation Assay. The effect of MAb4D5 variants upon proliferation of the human mammary adenocarcinoma cell line, SK-BR-3, was investigated as previously described (Fendly, B. M. et al., *Cancer Res.* 50:1550–1558 (1990)) using saturating MAb4D5 concentrations.

Affinity Measurements. The antigen binding affinity of MAb4D5 variants was determined using a secreted form of the p185$^{HER2}$ ECD prepared as described in Fendly, B. M. et al., *J. Biol. Resp. Mod.* 9:449–455 (1990). Briefly, antibody and p185$^{HER2}$ ECD were incubated in solution until equilibrium was found to be reached. The concentration of free antibody was then determined by ELISA using immobilized p185$^{HER2}$ ECD and used to calculate affinity ($K_d$) according to Friguet et al. (Friguet. B. et al., *J. Immunol. Methods* 77:305–319 (1985)).

RESULTS

Humanization of muMAb4D5. The muMAb4D5 $V_L$ and $V_H$ gene segments were first cloned by PCR and sequenced (FIG. 1). The variable genes were then simultaneously humanized by gene conversion mutagenesis using preassembled oligonucleotides (FIG. 2). A 311-mer oligonucleotide containing 39 mismatches to the template directed 24 simultaneous amino acid changes required to humanize muMAb4D5 $V_L$. Humanization of muMAb4D5 $V_H$ required 32 amino acid changes which were installed with a 361-mer containing 59 mismatches to the muMAb4D5 template. Two out of 8 clones sequenced precisely encode huMAb4D5-5, although one of these clones contained a single nucleotide imperfection. The 6 other clones were essentially humanized but contained a small number of errors: <3 nucleotide changes and <1 single nucleotide deletion per kilobase. Additional humanized variants (Table 3) were constructed by site-directed mutagenesis of huMAb4D5-5

Expression levels of huMAb4D5 variants were in the range of 7 to 15 μg/ml as judged by ELISA using immobilized p185$^{HER2}$ ECD. Successive harvests of five 10 cm plates allowed 200 μg to 500 mg of each variant to be produced in a week. Antibodies affinity purified on protein A gave a single band on a Coomassie blue stained SDS polyacrylamide gel of mobility consistent with the expected $M_r$ of 18 150 kDa. Electrophoresis under reducing conditions gave 2 bands consistent with the expected $M_r$ of free heavy (48 kDa) and light (23 kDa) chains (not shown). Amino terminal sequence analysis (10-cycles) gave the mixed sequence expected (see FIG. 1) from an equimolar combination of light and heavy chains (not shown).

huMAb4D5 Variants. In general, the FR residues were chosen from consensus human sequences (Kabat, E. A. et al., *Sequences of Proteins of Immunological Interest* (National Institutes of Health, Bethesda, Md., 1987)) and CDR residues from muMAb4D5. Additional variants were constructed by replacing selected human residues in huMAb4D5-1 with their muMAb4D5 counterparts. These are $V_H$ residues 71, 73, 78, 93 plus 102 and $V_L$ residues 55 plus 66 identified by our molecular modeling. $V_H$ residue 71 has previously been proposed by others (Tramontano, A. et al., *J. Mol. Biol.* 215:175–182 (1990)) to be critical to the conformation of $V_H$-CDR2. Amino acid sequence differences between huMAb4D5 variant molecules are shown in Table 3, together with their p185$^{HER2}$ ECD binding affinity and maximal anti-proliferative activities against SK-BR-3 cells. Very similar $K_d$ values were obtained for binding of MAb4D5 variants to either SK-BR-3 cells or to p185$^{HER2}$ ECD (Table 3). However, $K_d$ estimates derived from binding of MAb4D5 variants to p185$^{HER2}$ ECD were more reproducible with smaller standard errors and consumed much smaller quantities of antibody than binding measurements with whole cells.

Figure 3:
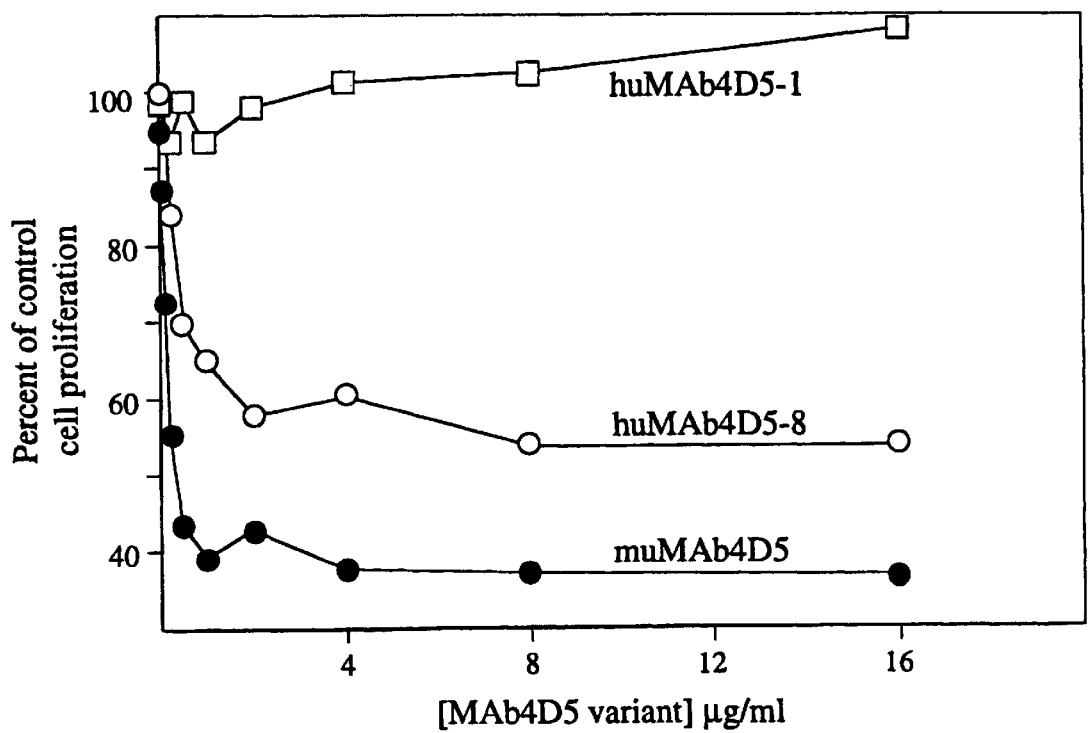
FIG. 3 shows the inhibition of SK-BR-3 proliferation by MAb4D5 variants. Relative cell proliferation was determined as described (Hudziak, R. M. et al., *Molec. Cell. Biol.* 9:1165–1172 (1989)) and data (average of triplicate determinations) are presented as a percentage of results with untreated cultures for muMAb4D5 (•), huMAb4D5-8 (○) and huMAb4D5-1 (□).

The most potent humanized variant designed by molecular modeling, huMAb4D5-8, contains 5 FR residues from muMAb4D5. This antibody binds the p185$^{HER2}$ ECD 3-fold more tightly than does muMAb4D5 itself (Table 3) and has comparable anti-proliferative activity with SK-BR-3 cells (FIG. 3). In contrast, huMAb4D5-1 is the most humanized but least potent muMAb4D5 variant, created by simply installing the muMAb4D5 CDRs into the consensus human sequences. huMAb4D5-1 binds the p185$^{HER2}$ ECD 80-fold less tightly than does the murine antibody and has no detectable anti-proliferative activity at the highest antibody concentration investigated (16 μg/ml).

The anti-proliferative activity of huMAb4D5 variants against p185$^{HER2}$ overexpressing SK-BR-3 cells is not simply correlated with their binding affinity for the p185$^{HER2}$ ECD. For example, installation of three murine residues into the $V_H$ domain of huMAb4D5-2 (D73T, L78A and A93S) to create huMAb4D5-3 does not change the antigen binding affinity but does confer significant anti-proliferative activity (Table 3).

The importance of $V_H$ residue 71 (Tramontano, A. et al., *J. Mol. Biol.* 215:175–182 (1990)) is supported by the observed 5-fold increase in affinity for p185$^{HER2}$ ECD on replacement of R71 in huMAb4D5-1 with the corresponding murine residue, alanine (huMAb4D5-2). In contrast, replacing $V_H$ L78 in huMAb4D5-4 with the murine residue, alanine (huMAb4D5-5), does not significantly change the affinity for the p185$^{HER2}$ ECD or change anti-proliferative activity, suggesting that residue 78 is not of critical functional significance to huMAb4D5 and its ability to interact properly with the extracellular domain of p185$^{HER2}$.

Figure 4:
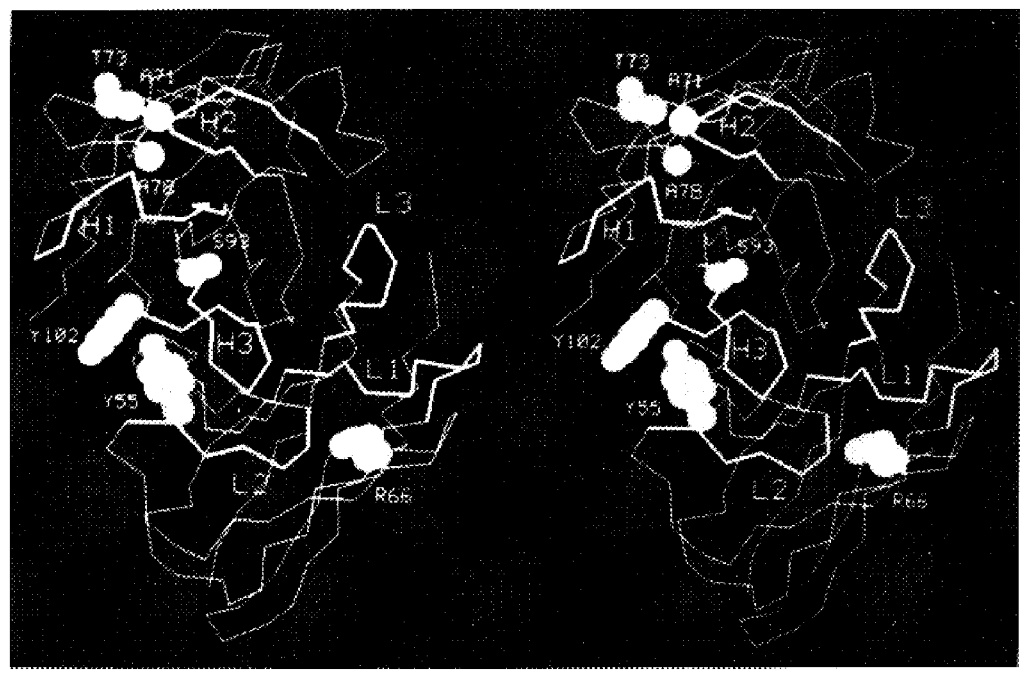
FIG. 4 shows a stereo view of α-carbon tracing for a model of huMAb4D5-8 $V_L$ and $V_H$. The CDR residues (Kabat, E. A. et al., *Sequences of Proteins of Immunological Interest* (National Institutes of Health, Bethesda, Md., 1987)) are shown in bold and side chains of $V_H$ residues A71, T73, A78, S93, Y102 and $V_L$ residues Y55 plus R66 (see Table 3) are shown.

$V_L$ residue 66 is usually a glycine in human and murine κ chain sequences (Kabat, E. A. et al., *Sequences of Proteins of Immunological Interest* (National Institutes of Health, Bethesda, Md., 1987)) but an arginine occupies this position in the muMAb4D5 k light chain. The side chain of residue 66 is likely to affect the conformation of $V_L$-CDR1 and $V_L$-CDR2 and the hairpin turn at 68–69 (FIG. 4). Consistent with the importance of this residue, the mutation $V_L$ G66R (huMAb4D5-3 huMAb4D5-5) increases the affinity for the p185$^{HER2}$ ECD by 4-fold with a concomitant increase in anti-proliferative activity.

From molecular modeling it appears that the tyrosyl side chain of muMAb4D5 $V_L$ residue 55 may either stabilize the conformation of $V_H$-CDR3 or provide an interaction at the $V_L$-$V_H$ interface. The latter function may be dependent upon the presence of $V_H$ Y102. In the context of huMAb4D5-5 the mutations $V_L$ E55Y (huMAb4D5-6) and $V_H$ V102Y (huMAb4D5-7) individually increase the affinity for p185$^{HER2}$ ECD by 5-fold and 2-fold respectively, whereas together (huMAb4D5-8) they increase the affinity by 11-fold. This is consistent with either proposed role of $V_L$ Y55 and $V_H$ Y102.

Secondary Immune Function of huMAb4D5-8. MuMAb4D5 inhibits the growth of human breast tumor cells which overexpress p185$^{HER2}$ (Hudziak, R. M. et al., *Molec. Cell. Biol.* 9:1165–1172 (1989)). The antibody, however, does not offer the possibility of direct tumor cytotoxic effects. This possibility does arise in huMAb4D5-8 as a result of its high affinity ($K_d$=0.1 μM) and its human IgG$_1$ subtype. Table 4 compares the ADCC mediated by huMAb4D5-8 with muMAb4D5 on a normal lung epithelial cell line, WI-38, which expresses a low level of p185$^{HER2}$ and on SK-BR-3, which expresses a high level of p185$^{HER2}$, The results demonstrate that: (1) huMAb4D5 has a greatly enhanced ability to carry out ADCC as compared with its murine parent; and (2) that this activity may be selective for cell types which overexpress p185$^{HER2}$.

DISCUSSION

MuMAb4D5 is potentially useful for human therapy since it is cytostatic towards human breast and ovarian tumor lines overexpressing the HER2-encoded p185$^{HER2}$ receptor-like tyrosine kinase. Since both breast and ovarian carcinomas are chronic diseases it is anticipated that the optimal MAb4D5 variant molecule for therapy will have low immunogenicity and will be cytotoxic rather than solely cytostatic in effect. Humanization of muMAb4D5 should accomplish these goals. We have identified 5 different huMAb4D5 variants which bind tightly to p185$^{HER2}$ ECD ($K_d \leq 1$ nM) and which have significant anti-proliferative activity (Table 3). Furthermore huMAb4D5-8 but not muMAb4D5 mediates ADCC against human tumor cell lines overexpressing p185$^{HER2}$ in the presence of human effector cells (Table 4) as anticipated for a human γ1 isotype (Brüggemann, M. et al., *J. Exp. Med.* 166:1351–1361 (1987); Riechmann, L. et al., *Nature* 332:323–327 (1988)).

Rapid humanization of huMAb4D5 was facilitated by the gene conversion mutagenesis strategy developed here using long preassembled oligonucleotides. This method requires less than half the amount of synthetic DNA as does total gene synthesis and does not require convenient restriction sites in the target DNA. Our method appears to be simpler and more reliable than a variant protocol recently reported (Rostapshov, V. M. et al., *FEBS Lett.* 249:379–382 (1989)). Transient expression of huMAb4D5 in human embryonic kidney 293 cells permitted the isolation of a few hundred micrograms of huMAb4D5 variants for rapid characterization by growth inhibition and antigen binding affinity assays. Furthermore, different combinations of light and heavy chain were readily tested by co-transfection of corresponding cDNA expression vectors.

The crucial role of molecular modeling in the humanization of muMAb4D5 is illustrated by the designed variant huMAb4D5-8 which binds the p185$^{HER2}$ ECD 250-fold more tightly than the simple CDR loop swap variant, huMAb4D5-1. It has previously been shown that the antigen binding affinity of a humanized antibody can be increased by mutagenesis based upon molecular modelling (Riechmann, L. et al., *Nature* 332:323–327 (1988); Queen, C. et al., *Proc. Natl. Acad. Sci. USA* 86:10029–10033 (1989)). Here we have extended this earlier work by others with a designed humanized antibody which binds its antigen 3-fold more tightly than the parent rodent antibody. While this result is gratifying, assessment of the success of the molecular modeling must await the outcome of X-ray structure determination. From analysis of huMAb4D5 variants (Table 3) it is apparent that their anti-proliferative activity is not a simple function of their binding affinity for p185$^{HER2}$ ECD. For example the huMAb4D5-8 variant binds p185$^{HER2}$ 3-fold more tightly than muMAb4D5 but the humanized variant is slightly less potent in blocking the proliferation of SK-BR-3 cells. Additional huMAb4D5 variants are currently being constructed in an attempt to identify residues triggering the anti-proliferative activity and in an attempt to enhance this activity.

In addition to retaining tight receptor binding and the ability to inhibit cell growth, the huMAb4D5-8 also confers a secondary immune function (ADCC). This allows for direct cytotoxic activity of the humanized molecule in the presence of human effector cells. The apparent selectivity of the cytotoxic activity for cell types which overexpress p185$^{HER2}$ allows for the evolution of a straightforward clinic approach to those human cancers characterized by overexpression of the HER2 protooncogene.

TABLE 3 p185$^{HER2}$ ECD binding affinity and anti-proliferative activities of MAb4D5 variants

| MAb4D5 cell Variant proliferation[‡] | V$_H$ Residue* | | | | | V$_L$ Residue* | | K$_d$[†] nM | Relative |
|---|---|---|---|---|---|---|---|---|---|
| | 71 FR3 | 73 FR3 | 78 FR3 | 93 FR3 | 102 CDR3 | 55 CDR2 | 66 FR3 | | |
| huMAb4D5-1 | R | D | L | A | V | E | G | 25 | 102 |
| huMAb4D5-2 | Ala | D | L | A | V | E | G | 4.7 | 101 |
| huMAb4D5-3 | Ala | Thr | Ala | Ser | V | E | G | 4.4 | 66 |
| huMAb4D5-4 | Ala | Thr | L | Ser | V | E | Arg | 0.82 | 56 |
| huMAb4D5-5 | Ala | Thr | Ala | Ser | V | E | Arg | 1.1 | 48 |
| huMAb4D5-6 | Ala | Thr | Ala | Ser | V | Tyr | Arg | 0.22 | 51 |
| huMAb4D5-7 | Ala | Thr | Ala | Ser | Tyr | E | Arg | 0.62 | 53 |
| huMAb4D5-8 | Ala | Thr | Ala | Ser | Tyr | Tyr | Arg | 0.10 | 54 |
| muMAb4D5 | Ala | Thr | Ala | Ser | Tyr | Tyr | Arg | 0.30 | 37 |

*Human and murine residues are shown in one letter and three letter amino acid code respectively.
[†]K$_d$ values for the p185$^{HER2}$ ECD were determined using the method of Friguet et al. (43) and the standard error of each estimate is ≦ ± 10%.
[‡]Proliferation of SK-BR-3 cells incubated for 96 hr with MAb4D5 variants shown as a percentage of the untreated control as described (Hudziak, R. M. et al., Molec. Cell. Biol. 9:1165–1172 (1989)). Data represent the maximal anti-proliferative effect for each variant (see FIG. 3A) calculated as the mean of triplicate determinations at a MAb4D5 concentration of 8 μg/ml. Data are all taken from the same experiment with an estimated standard error of ≦ ± 15%.

TABLE 4

Selectivity of antibody dependent tumor cell cytotoxicity mediated by huMAb4D5-8

| Effector:Target ratio[†] | WI-38* | | SK-BR-3 | |
|---|---|---|---|---|
| | muMAb4D5 | huMAb4D5-8 | muMAb4D5 | huMAb4D5-8 |
| A.[‡] | 25:1 | <1.0 | 9.3 | 7.5 | 40.6 |
| | 12.5:1 | <1.0 | 11.1 | 4.7 | 36.8 |
| | 6.25:1 | <1.0 | 8.9 | 0.9 | 35.2 |
| | 3.13:1 | <1.0 | 8.5 | 4.6 | 19.6 |
| B. | 25:1 | <1.0 | 3.1 | 6.1 | 33.4 |
| | 12.5:1 | <1.0 | 1.7 | 5.5 | 26.2 |
| | 6.25:1 | 1.3 | 2.2 | 2.0 | 21.0 |
| | 3.13:1 | <1.0 | 0.8 | 2.4 | 13.4 |

*Sensitivity to ADCC of two human cell lines (WI-38, normal lung epithelium; and SK-BR-3, human breast tumor cell line) are compared. WI-38 expresses a low level of p185$^{HER2}$ (0.6 pg per μg cell protein) and SK-BR-3 expresses a high level of p185$^{HER2}$ (64 pg p185$^{HER2}$ per μg cell protein), as determined by ELISA (Fendly et al., J. Biol. Resp. Mod. 9:449–455 (1990)).
[†]ADCC assays were carried out as described in Brüggemann et al., J. Exp. Med. 166:1351–1361 (1987). Effector to target ratios were of IL-2 activated human peripheral blood lymphocytes to either WI-38 fibroblasts or SK-BR-3 tumor cells in 96-well microtiter plates for 4 hours at 37° C.. Values given represent percent specific cell lysis as determined by $^{51}$Cr release. Estimated standard error in these quadruplicate determinations was ≦ ± 10%.
[‡]Monoclonal antibody concentrations used were 0.1 μg/ml (A) and 0.1 μg/ml (B).

Example 2

Schematic Method for Humanizing an Antibody Sequence

This example illustrates one stepwise elaboration of the methods for creating a humanized sequence described above. It will be understood that not all of these steps are essential to the claimed invention, and that steps may be taken in different order.

1. ascertain a consensus human variable domain amino acid sequence and prepare from it a consensus structural model.
2. prepare model of import (the non-human domain to be humanized) variable domain sequences and note structural differences with respect to consensus human model.
3. identify CDR sequences in human and in import, both by using Kabat (supra, 1987) and crystal structure criteria. If there is any difference in CDR identity from the different criteria, use of crystal structure definition of the CDR, but retain the Kabat residues as important framework residues to import.
4. substitute import CDR sequences for human CDR sequences to obtain initial "humanized" sequence.
5. compare import non-CDR variable domain sequence to the humanized sequence and note divergences.
6. Proceed through the following analysis for each amino acid residue where the import diverges from the humanized.
    a. If the humanized residue represents a residue which is generally highly conserved across all species, use the residue in the humanized sequence. If the residue is not conserved across all species, proceed with the analysis described in 6b.

b. If the residue is not generally conserved across all species, ask if the residue is generally conserved in humans.
  i. If the residue is generally conserved in humans but the import residue differs, examine the structural models of the import and human sequences and determine if the import residue would be likely to affect the binding or biological activity of the CDRs by considering 1) could it bind antigen directly and 2) could it affect the conformation of the CDR. If the conclusion is that an affect on the CDRs is likely, substitute the import residue. If the conclusion is that a CDR affect is unlikely, leave the humanized residue unchanged.
  ii. If the residue is also not generally conserved in humans, examine the structural models of the import and human sequences and determine if the import residue would be likely to affect the binding or biological activity of the CDRs be considering 1) could it bind antigen directly and 2) could it affect the conformation of the CDR. If the conclusion is that an affect on the CDRs is likely, substitute the import residue. If the conclusion is that a CDR affect is unlikely, proceed to the next step.
    a) Examine the structural models of the import and human sequences and determine if the residue is exposed on the surface of the domain or is buried within. If the residue is exposed, use the residue in the humanized sequence. If the residue is buried, proceed to the next step.
      (i) Examine the structural models of the import and human sequences and determine if the residue is likely to affect the $V_L$–$V_H$ interface. Residues involved with the interface include: 34L, 36L, 38L, 43L, 33L, 36L, 85L, 87L, 89L, 91L, 96L, 98L, 35H, 37H, 39H, 43H, 45H, 47H, 60H, 91H. 93H, 95H, 100H, and 103H. If no effect is likely, use the residue in the humanized sequence. If some affect is likely, substitute the import residue.
7. Search the import sequence, the consensus sequence and the humanized sequence for glycosylation sites outside the CDRs, and determine if this glycosylation site is likely to have any affect on antigen binding and/or biological activity. If no effect is likely, use the human sequence at that site; if some affect is likely, eliminate the glycosylation site or use the import sequence at that site.
8. After completing the above analysis, determine the planned humanized sequence and prepare and test a sample. If the sample does not bind well to the target antigen, examine the particular residues listed below, regardless of the question of residue identity between the import and humanized residues.
  a. Examine particular peripheral (non-CDR) variable domain residues that may, due to their position, possibly interact directly with a macromolecular antigen, including the following residues (where the * indicates residues which have been found to interact with antigen based on crystal structures):
    i. Variable light domain: 36, 46, 49*, 63–70
    ii. Variable heavy domain: 2, 47*, 68, 70, 73–76
  b. Examine particular variable domain residues which could interact with, or otherwise affect, the conformation of variable domain CDRs, including the following (not including CDR residues themselves, since it is assumed that, because the CDRs interact with one another, any residue in one CDR could potentially affect the conformation of another CDR residue) (L=LIGHT, H=HEAVY, residues appearing in bold are indicated to be structurally important according the Chothia et al., Nature 342:877 (1989), and residues appearing in italic were altered during humanization by Queen et al. (PDL), Proc. Natl. Acad. Sci. USA 86:10029 (1989) and Proc. Natl. Acad. Sci. USA 88:2869 (1991).):
    i. Variable light domain:
      a) CDR-1 (residues 24L–34L): 2L, 4L, 66L–69L, 71L
      b) CDR-2 (residues 50L–56L): 35L, 46L, 47L, 48L, 49L, 58L, 62L, 64L–66L, 71L, 73L
      c) CDR-3 (residues 89L–97L): 2L, 4L, 36L, 98L, 37H, 45H, 47H, 58H, 60H
    ii. Variable heavy domain:
      a) CDR-1 (residues 26H–35H): 2H, 4H, 24H, 36H, 71H, 73H, 76H, 78H, 92H, 94H
      b) CDR-2 (residues 50H–55H): 49H, 69H, 69H, 71H, 73H, 78H
      c) CDR-3 (residues 95H–102H): examine all residues as possible interaction partners with this loop, because this loop varies in size and conformation much more than the other CDRs.
9. If after step 8 the humanized variable domain still is lacking in desired binding, repeat step 8. In addition, re-investigate any buried residues which might affect the $V_L$–$V_H$ interface (but which would not directly affect CDR conformation). Additionally, evaluate the accessibility of non-CDR residues to solvent.

Example 3

Engineering a Humanized Bispecific F(ab')$_2$ Fragment

This example demonstrates the construction of a humanized bispecific antibody (BsF(ab')$_2$v1 by separate *E. coli* expression of each Fab' arm followed by directed chemical coupling in vitro. BsF(ab')$_2$ v1 (anti-CD3/anti-p185$^{HER2}$) was demonstrated to retarget the cytotoxic activity of human CD3$^+$ CTL in vitro against the human breast tumor cell line, SK-BR-3, which overexpresses the p185$^{HER2}$ product of the protooncogene HER2. This example demonstrates the minimalistic humanization strategy of installing as few murine residues as possible into a human antibody in order to recruit antigen-binding affinity and biological properties comparable to that of the murine parent antibody. This strategy proved very successful for the anti-p185$^{HER2}$ arm of BsF (ab')$_2$v1. In contrast BsF(ab')$_2$ v1 binds to T cells via its anti-CD3 arm much less efficiently than does the chimeric BsF(ab')$_2$ which contains the variable domains of the murine parent anti-CD3 antibody. Here we have constructed additional BsF(ab')$_2$ fragments containing variant anti-CD3 arms with selected murine residues restored in an attempt to improve antibody binding to T cells. One such variant, Bs F(ab')$_2$ v9, was created by replacing six residues in the second hypervariable loop of the anti-CD3 heavy chain variable domain of BsF(ab')$_2$ v1 with their counterparts from the murine parent anti-CD3 antibody. BsF(ab')$_2$ v9 binds to T cells (Jurkat) much more efficiently than does BsF(ab')$_2$ v1 and almost as efficiently as the chimeric BsF(ab')$_2$. This improvement in the efficiency of T cell binding of the humanized BsF(ab')$_2$ is an important step in its development as a potential therapeutic agent for the treatment of p185$^{HER2}$-overexpressing cancers.

Bispecific antibodies (BsAbs) with specificities for tumor-associated antigens and surface markers on immune effector cells have proved effective for retargeting effector cells to kill tumor targets both in vitro and in vivo (reviewed by Fanger, M. W. et al., *Immunol. Today* 10: 92–99 (1989); Fanger, M. W. et al., *Immunol. Today* 12: 51–54 (1991); and Nelson, H., *Cancer Cells* 3:163–172 (1991)). BsF(ab')$_2$ fragments have often been used in preference to intact BsAbs in retargeted cellular cytotoxicity to avoid the risk of killing innocent bystander cells binding to the Fc region of the antibody. An additional advantage of BsF(ab')$_2$ over intact BsAbs is that they are generally much simpler to prepare free of contaminating monospecific molecules (reviewed by Songsivilai, S. and Lachmann, P. J., *Clin. Exp. Immunol.* 79: 315–321 (1990) and Nolan, O. and O'Kennedy, R., *Biochim. Biophys. Acta* 1040: 1–11 (1990)).

BsF(ab')$_2$ fragments are traditionally constructed by directed chemical coupling of Fab' fragments obtained by limited proteolysis plus mild reduction of the parent rodent monoclonal Ab (Brennan, M. et al., *Science* 229, 81–83 (1985) and Glennie, M. J. et al., *J. Immunol.* 139: 2367–2375 (1987)). One such BsF(ab')$_2$ fragment (anti-glioma associated antigen/anti-CD3) was found to have clinical efficacy in glioma patients (Nitta, T. et al., *Lancet* 335: 368–371 (1990) and another BsF(ab')$_2$ (anti-indium chelate/anti-carcinoembryonic antigen) allowed clinical imaging of colorectal carcinoma (Stickney, D. R. et al., *Antibody, Immunoconj. Radiopharm.* 2: 1–13 (1989)). Future BsF(ab')$_2$ destined for clinical applications are likely to be constructed from antibodies which are either human or at least "humanized" (Riechmann, L. et al., *Nature* 332: 323–327 (1988) to reduce their immunogenicity (Hale, G. et al., *Lancet* i: 1394–1399 (1988)).

Recently a facile route to a fully humanized BsF(ab')$_2$ fragment designed for tumor immunotherapy has been demonstrated (Shalaby, M. R. et al., *J. Exp. Med.* 175: 217–225 (1992)). This approach involves separate *E. coli* expression of each Fab' arm followed by traditional directed chemical coupling in vitro to form the BsF(ab')$_2$. One arm of the BsF(ab')$_2$ was a humanized version (Carter, P. et al., *Proc. Natl. Acad. Sci. USA* (1992a) and Carter, P., et al., *Bio/Technology* 10: 163–167 (1992b)) of the murine monoclonal Ab 4D5 which is directed against the p185$^{HER2}$ product of the protooncogene HER2 (c-erbB-2) (Fendly, B. M. et al. *Cancer Res.* 50: 1550–1558 (1989)). The humanization of the antibody 4D5 is shown in Example 1 of this application. The second arm was a minimalistically humanized anti-CD3 antibody (Shalaby et al. supra) which was created by installing the CDR loops from the variable domains of the murine parent monoclonal Ab UCHT1 (Beverley, P. C. L. and Callard, R. E., *Eur. J. Immunol.* 11: 329–334 (1981)) into the humanized anti-p185$^{HER2}$ antibody. The BsF(ab')$_2$ fragment containing the most potent humanized anti-CD3 variant (v1) was demonstrated by flow cytometry to bind specifically to a tumor target overexpressing p185$^{HER2}$ and to human peripheral blood mononuclear cells carrying CD3. In addition, Bs F(ab')$_2$ v1 enhanced the cytotoxic effects of activated human CTL 4-fold against SK-BR-3 tumor cells overexpressing p185$^{HER2}$. The example descries efforts to improve the antigen binding affinity of the humanized anti-CD3 arm by the judicious recruitment of a small number of additional murine residues into the minimalistically humanized anti-CD3 variable domains.

MATERIALS AND METHODS

Construction of Mutations in the Anti-CD3 Variable Region Genes

The construction of genes encoding humanized anti-CD3 variant 1 (v1) variable light (V$_L$) and heavy (V$_H$) chain domains in phagemid pUC119 has been described (Shalaby et al. supra). Additional anti-CD3 variants were generated using an efficient site-directed mutagenesis method (Carter, P., *Mutagenesis: a practical approach*, (M. J. McPherson, Ed.). Chapter 1, IRL Press, Oxford, UK (1991)) using mismatched oligonucleotides which either install or remove unique restriction sites. Oligonucleotides used are listed below using lowercase to indicate the targeted mutations. Corresponding coding changes are denoted by the starting amino acid in one letter code followed by the residue numbered according to Kabat, E. A. et al., *Sequences of Proteins of Immunological Interest*, 5$^{th}$ edition, National Institutes of Health, Bethesda, Md., USA (1991), then the replacement amino acid and finally the identity of the anti-CD3 variant:

HX11, 5' GTAGATAAATCCtctAACACAGC-CTAtCTGCAAATG 3' (SEQ.ID. NO. 11) V$_H$ K75S, v6;

HX12, 5' GTAGATAAATCCAAAtctACAGC-CTAtCTGCAAATG 3' (SEQ.ID. NO. 12) V$_H$ N76S, v7;

HX13, 5' GTAGATAAATCCtcttctACAGC-CTAtCTGCAAATG 3' (SEQ.ID. NO. 13) V$_H$ K75S:N76S, v8;

X14, 5' CTTATAAAGGTGTTtCcACCTATaaCcA-gAaatTCAA GGatCGTTTCACgATAtcCGTA-GATAAATCC 3' (SEQ.ID.NO. 14) V$_H$ T57S:A60N:D61Q:S62K:V63F:G65D, v9;

LX6, 5' CTATACCTCCCGTCTgcatTCTGGAGTCCC 3' (SEQ.ID. NO. 15) V$_L$ E55H, v11.

Oligonucleotides HX11, HX12 and HX13 each remove a site for BspMI, whereas LX6 removes a site for XhoI and HX14 installs a site for EcoRV (bold). Anti-CD3 variant v10 was constructed from v9 by site-directed mutagenesis using oligonucleotide HX13. Mutants were verified by dideoxy-nucleotide sequencing (Sanger, F. et al., *Proc. Natl. Acad. Sci. USA* 74: 5463–5467 (1977)).

*E. coli* Expression of Fab' Fragments

The expression plasmid, pAK19, for the co-secretion of light chain and heavy chain Fd' fragment of the most preferred humanized anti-p185$^{HER2}$ variant, HuMAb4D5-8, is described in Carter et al., 1992b, supra. Briefly, the Fab' expression unit is bicistronic with both chains under the transcriptional control of the phoA promoter. Genes encoding humanized V$_L$ and V$_H$ domains are precisely fused on their 5' side to a gene segment encoding the heat-stable enterotoxin II signal sequence and on their 3' side to human k$_1$ C$_L$ and IgG1 C$_H$1 constant domain genes, respectively. The C$_H$1 gene is immediately followed by a sequence encoding the hinge sequence CysAlaAla and followed by a bacteriophage λ t$_0$ transcriptional terminator. Fab' expression plasmids for chimeric and humanized anti-CD3 variants (v1 to v4, Shalaby et al., supra; v6 to v12, this study) were created from pAK19 by precisely replacing anti-p185$^{HER2}$ V$_L$ and V$_H$ gene segments with those encoding murine and corresponding humanized variants of the anti-CD3 antibody, respectively, by sub-cloning and site-directed mutagenesis. The Fab' expression plasmid for the most potent humanized anti-CD3 variant identified in this study (v9) is designated pAK22. The anti-p185$^{HER2}$ Fab' fragment was secreted from *E. coli* K12 strain 25F2 containing plasmid pAK19 grown for 32 to 40 hr at 37° C. in an aerated 10 liter fermentor. The final cell density was 120–150 OD$_{550}$ and the titer of soluble and functional anti-p185$^{HER2}$ Fab' was 1–2 g/liter as judged by antigen binding ELISA (Carter et al., 1992b, supra).

Anti-CD3 Fab' variants were secreted from E. coli containing corresponding expression plasmids using very similar fermentation protocols. The highest expression titers of chimeric and humanized anti-CD3 variants were 200 mg/liter and 700 mg/liter, respectively, as judged by total immunoglobulin ELISA.

Construction of BsF(ab')$_2$ Fragments

Fab' fragments were directly recovered from E. coli fermentation pastes in the free thiol form (Fab'-SH) by affinity purification on Streptococcal protein G at pH 5 in the presence of EDTA (Carter et al., 1992b supra). Thioether linked BsF(ab')$_2$ fragments (anti-p185$^{HER2}$/anti-CD3) were constructed by the procedure of Glennie et al. supra with the following modifications. Anti-p185$^{HER2}$ Fab'-SH in 100 mM Tris acetate, 5 mM EDTA (pH 5.0) was reacted with 0.1 vol of 40 mM N,N'-1,2-phenylenedimalemide (o-PDM) in dimethyl formamide for ~1.5 hr at 20° C. Excess o-PDM was removed by protein G purification of the Fab' maleimide derivative (Fab'-mal) followed by buffer exchange into 20 mM sodium acetate, 5 mM EDTA (pH 5.3) (coupling buffer) using centriprep-30 concentrators (Amicon). The total concentration of Fab' variants was estimated from the measured absorbance at 280 nm (HuMAb4D5-8 Fab' $e^{0.1\%}$=1.56, Carter et al., 1992b, supra). The free thiol content of Fab' preparations was estimated by reaction with 5,5'-dithiobis (2-nitrobenzoic acid) as described by Creighton, T. E., *Protein structure: a practical approach*, (T. E. Creighton, Ed.), Chapter 7, IRL Press, Oxford, UK (1990). Equimolar amounts of anti-p185$^{HER2}$ Fab'-mal (assuming quantitative reaction of Fab'-SH with o-PDM) and each anti-CD3 Fab'-SH variant were coupled together at a combined concentration of 1 to 2.5 mg/ml in the coupling buffer for 14 to 48 hr at 4° C. The coupling reaction was adjusted to 4 mM cysteine at pH 7.0 and incubated for 15 min at 20° C. to reduce any unwanted disulfide-linked F(ab')$_2$ formed. These reduction conditions are sufficient to reduce inter-heavy chain disulfide bonds with virtually no reduction of the disulfide between light and heavy chains. Any free thiols generated were then blocked with 50 mM iodoacetamide. BsF(ab')$_2$ was isolated from the coupling reaction by S100-HR (Pharmacia) size exclusion chromatography (2.5 cm×100 cm) in the presence of PBS. The BsF(ab')$_2$ samples were passed through a 0.2 mm filter flash frozen in liquid nitrogen and stored at −70° C.

Flow Cytometric Analysis of F(ab')$_2$ Binding to Jurkat Cells

The Jurkat human acute T cell leukemia cell line was purchased from the American Type Culture Collection (Manassas Va.) (ATCC TIB 152) and grown as recommended by the ATCC. Aliquots of $10^6$ Jurkat cells were incubated with appropriate concentrations of BsF(ab')$_2$ (anti-p185$^{HER2}$/anti-CD3 variant) or control mono-specific anti-p185$^{HER2}$ F(ab')$_2$ in PBS plus 0.1% (w/v) bovine serum albumin and 10 mM sodium azide for 45 min at 4° C. The cells were washed and then incubated with fluorescein-conjugated goat anti-human F(ab')$_2$ (Organon Teknika, West Chester, Pa.) for 45 min at 4° C. Cells were washed and analyzed on a FACScan* (Becton Dickinson and Co., Mountain View, Calif.). Cells (8×10$^3$) were acquired by list mode and gated by forward light scatter versus side light scatter excluding dead cells and debris.

RESULTS

Design of Humanized Anti-CD3 Variants

The most potent humanized anti-CD3 variant previously identified, v1, differs from the murine parent antibody, UCHT1 at 19 out of 107 amino acid residues within $V_L$ and at 37 out of 122 positions within $V_H$ (Shalaby et al., supra) 1992). Here we recruited back additional murine residues into anti-CD3 v1 in an attempt to improve the binding affinity for CD3. The strategy chosen was a compromise between minimizing both the number of additional murine residues recruited and the number of anti-CD3 variants to be analyzed. We focused our attentions on a few CDR residues which were originally kept as human sequences in our minimalistic humanization regime. Thus human residues in $V_H$ CDR2 of anti-CD3 v1 were replaced en bloc with their murine counterparts to give anti-CD3 v9: T57S:A60N:D61Q:S62K:V63F:G65D (SEQ ID NO:20). Similarly, the human residue E55 in $V_L$ CDR2 of anti-CD3 v1 was replaced with histidine from the murine anti-CD3 antibody to generate anti-CD3 v11. In addition, $V_H$ framework region (FR) residues 75 and 76 in anti-CD3 v1 were also replaced with their murine counterparts to create anti-CD3 v8: K75S:N76S. $V_H$ residues 75 and 76 are located in a loop close to $V_H$ CDR1 and CDR2 and therefore might influence antigen binding. Additional variants created by combining mutations at these three sites are described below.

Preparation of BsF(ab')$_2$ Fragments

Soluble and functional anti-p185$^{HER2}$ and anti-CD3 Fab' fragments were recovered directly from corresponding E. coli fermentation pastes with the single hinge cysteine predominantly in the free thiol form (75–100% Fab'-SH) by affinity purification on Streptococcal protein G at pH 5 in the presence of EDTA (Carter et al., 1992b, supra). Thioether-linked BsF(ab')$_2$ fragments were then constructed by directed coupling using o-PDM as described by Glennie et al., supra. One arm was always the most potent humanized anti-p185$^{HER2}$ variant, HuMAb4D5-8 (Carter et al., 1992a, supra) and the other either a chimeric or humanized variant of the anti-CD3 antibody. Anti-p185$^{HER2}$ Fab'-SH was reacted with o-PDM to form the maleimide derivative (Fab'-mal) and then coupled to the Fab'-SH for each anti-CD3 variant. F(ab')$_2$ was then purified away from unreacted Fab' by size exclusion chromatography as shown for a representative preparation (BsF(ab')$_2$ v8) in data not shown. The F(ab')$_2$ fragment represents ~54% of the total amount of antibody fragments (by mass) as judged by integration of the chromatograph peaks.

SDS-PAGE analysis of this BsF(ab')$_2$ v8 preparation under non-reducing conditions gave one major band with the expected mobility ($M_r$~96 kD) as well as several very minor bands (data not shown). Amino-terminal sequence analysis of the major band after electroblotting on to polyvinylidene difluoride membrane Matsudaira, P., *J. Biol. Chem.* 262: 10035–10038 (1987) gave the expected mixed sequence from a stoichiometric 1:1 mixture of light and heavy chains ($V_L/V_H$: D/E, I/V, Q/Q, M/L, T/V, Q/E, S/S) expected for BsF(ab')$_2$. The amino terminal region of both light chains are identical as are both heavy chains and correspond to consensus human FR sequences. We have previously demonstrated that F(ab')$_2$ constructed by directed chemical coupling carry both anti-p185$^{HER}$2 and anti-CD3 antigen specificities (Shalaby et al., supra). The level of contamination of the BsF(ab')$_2$ with monospecific F(ab')$_2$ is likely to be very low since mock coupling reactions with either anti-p185$^{HER2}$ Fab'-mal or anti-CD3 Fab'-SH alone did not yield detectable quantities of F(ab')$_2$. Furthermore the coupling reaction was subjected to a mild reduction step followed by alkylation to remove trace amounts of disulfide-linked F(ab')$_2$ that might be present. SDS-PAGE of the purified F(ab')$_2$ under reducing conditions gave two major bands with electrophoretic mobility and amino terminal sequence anticipated for free light chain and thioether-linked heavy chain dimers.

Scanning LASER densitometry of a o-PDM coupled F(ab')$_2$ preparation suggest that the minor species together represent ~10% of the protein. These minor contaminants were characterized by amino terminal sequence analysis and were tentatively identified on the basis of stoichiometry of light and heavy chain sequences and their electrophoretic mobility (data not shown). These data are consistent with the minor contaminants including imperfect F(ab')$_2$ in which the disulfide bond between light and heavy chains is missing in one or both arms, trace amounts of Fab' and heavy chain thioether-linked to light chain.

Binding of BsF(ab')$_2$ to Jurkat Cells

Binding of BsF(ab')$_2$ containing different anti-CD3 variants to Jurkat cells (human acute T cell leukemia) was investigated by flow cytometry (data not shown). BsF(ab')$_2$ v9 binds much more efficiently to Jurkat cells than does our starting molecule, BsF(ab')$_2$ v1, and almost as efficiently as the chimeric BsF(ab')$_2$. Installation of additional murine residues anti-CD3 v9 to create v10 (V$_H$ K75S:N76S) and v12 (V$_H$ K75S:N76S plus V$_L$ E55H) did not further improve binding of corresponding BsF(ab')$_2$ to Jurkat cells. Nor did recruitment of these murine residues into anti-CD3 v1 improve Jurkat binding: V$_H$K75S (v6), V$_H$N76S (v7), V$_H$K75S:N76S (v8), V$_L$ E55H (v11) (not shown). BsF(ab')$_2$ v9 was chosen for future study since it is amongst the most efficient variants in binding to Jurkat cells and contains fewest murine residues in the humanized anti-CD3 arm. A monospecific anti-p185$^{HER2}$ F(ab')$_2$ did not show significant binding to Jurkat cells consistent with the interaction being mediated through the anti-CD3 arm.

DISCUSSION

A minimalistic strategy was chosen to humanize the anti-p185$^{HER2}$ (Carter et al., 1992a, supra) and anti-CD3 arms (Shalaby et al., supra) of the BsF(ab')$_2$ in this study in an attempt to minimize the potential immunogenicity of the resulting humanized antibody in the clinic. Thus we tried to install the minimum number of murine CDR and FR residues into the context of consensus human variable domain sequences as required to recruit antigen-binding affinity and biological properties comparable to the murine parent antibody. Molecular modeling was used firstly to predict the murine FR residues which might be important to antigen binding and secondly to predict the murine CDR residues that might not be required. A small number of humanized variants were then constructed to test these predictions.

Our humanization strategy was very successful for the anti-p185$^{HER2}$ antibody where one out of eight humanized variants (HuMAb4D5-8, IgG1) was identified that bound the p185$^{HER2}$ antigen ~3-fold more tightly than the parent murine antibody (Carter et al., 1992a, supra). HuMAb4D5-8 contains a total of five murine FR residues and nine murine CDR residues, including V$_H$ CDR2 residues 60–65, were discarded in favor of human counterparts. In contrast, BsF (ab')$_2$ v1 containing the most potent humanized anti-CD3 variant out of four originally constructed (Shalaby et al., supra) binds J6 cells with an affinity (K$_d$) of 140 nM which is ~70-fold weaker than that of the corresponding chimeric BsF(ab')$_2$.

Here we have restored T cell binding of the humanized anti-CD3 close to that of the chimeric variant by replacing six human residues in V$_H$ CDR2 with their murine counterparts: T57S:A60N:D61Q:S62K:V63F:G65D (anti-CD3 v9, FIG. 5). It appears more likely that these murine residues enhance antigen binding indirectly by influencing the conformation of residues in the N-terminal part of V$_H$ CDR2 rather than by directly contacting antigen. Firstly, only N-terminal residues in V$_H$ CDR2 (50–58) have been found to contact antigen in one or more of eight crystallographic structures of antibody/antigen complexes (Kabat et al., supra; and Mian, I. S. et al., J. Mol. Biol. 217: 133–151 (1991), FIG. 5). Secondly, molecular modeling suggests that residues in the C-terminal part of V$_H$ CDR2 are at least partially buried (FIG. 5). BsF(ab')$_2$ v9 binds to SK-BR-3 breast tumor cells with equal efficiency to BsF(ab')$_2$ v1 and chimeric BsF(ab')$_2$ as anticipated since the anti-p185$^{HER}_2$ arm is identical in all of these molecules (Shalaby et al. supra, not shown).

Our novel approach to the construction of BsF(ab')$_2$ fragments exploits an E. coli expression system which secretes humanized Fab' fragments at gram per liter titers and permits their direct recovery as Fab'-SH (Carter et al., 1992b, supra). Traditional directed chemical coupling of Fab'-SH fragments is then used to form BsF(ab')$_2$ in vitro (Brennan et al., supra; and Glennie et al., supra). This route to Fab'-SH obviates problems which are inherent in their generation from intact antibodies: differences in susceptibility to proteolysis and nonspecific cleavage resulting in heterogeneity, low yield as well as partial reduction that is not completely selective for the hinge disulfide bonds. The strategy of using E. coli-derived Fab'-SH containing a single hinge cysteine abolishes some sources of heterogeneity in BsF(ab')$_2$ preparation such as intra-hinge disulfide formation and contamination with intact parent antibody whilst greatly diminishes others, eg. formation of F(ab')$_3$ fragments.

BsF(ab')$_2$ fragments constructed here were thioether-linked as originally described by Glennie et al., supra with future in vivo testing of these molecules in mind. Thioether bonds, unlike disulfide bonds, are not susceptible to cleavage by trace amounts of thiol, which led to the proposal that thioether-linked F(ab')$_2$ may be more stable than disulfide-linked F(ab')$_2$ in vivo (Glennie et al., supra). This hypothesis is supported by our preliminary pharmacokinetic experiments in normal mice which suggest that thioether-linked BsF(ab')$_2$ v1 has a 3-fold longer plasma residence time than BsF(ab')$_2$ v1 linked by a single disulfide bond. Disulfide and thioether-linked chimeric BsF(ab')$_2$ were found to be indistinguishable in their efficiency of cell binding and in their retargeting of CTL cytotoxicity, which suggests that o-PDM directed coupling does not compromise binding of the BsF(ab')$_2$ to either antigen (not shown). Nevertheless the nature of the linkage appears not to be critical since a disulfide-linked BsF(ab')$_2$ (murine anti-p185$^{HER2}$/murine anti-CD3) was recently shown by others (Nishimura et al., Int. J. Cancer 50: 800–804 (1992) to have potent anti-tumor activity in nude mice. Our previous study (Shalaby et al., supra) together with this one and that of Nishimura, T. et al., supra improve the potential for using BsF(ab')$_2$ in targeted immunotherapy of p185$^{HER2}$-overexpressing cancers in humans.

Example 4

Humanization of an Anti-CD18 Antibody

A murine antibody directed against the leukocyte adhesion receptor β-chain (known as the H52 antibody) was humanized following the methods described above. FIGS. 6A and 6B provide amino acid sequence comparisons for the murine and humanized antibody light chains and heavy chains.

We claim:

1. A method of treating cancer overexpressing p185$^{HER2}$ in a patient comprising administering to the patient a therapeutically effective amount of a humanized antibody that specifically binds p185$^{HER2}$, wherein the antibody comprises the $V_L$ and $V_H$ domains of an antibody selected from the group consisting of huMAb4D5-3 (SEQ ID NOS. 27 and 28, respectively), huMAb4D5-4 (SEQ ID NOS. 29 and 30, respectively), huMAb4D5-5 (SEQ ID NOS. 1 and 2, respectively), huMAb4D5-6 (SEQ ID NOS. 31 and 32, respectively), huMAb4D5-7 (SEQ ID NOS. 33 and 34, respectively), and huMAb4D5-8 (SEQ ID NOS. 35 and 36, respectively).

2. A method of treating cancer overexpressing p185$^{HER2}$ in a patient comprising administering to the patient a therapeutically effective amount of a humanized antibody that specifically binds p185$^{HER2}$, wherein he antibody comprises the $V_L$ and $V_H$ domains of huMAb4D5-8 (SEQ ID NOS. 35 and 36, respectively).

3. A method of treating ovarian cancer overexpressing p185$^{HER2}$ in a patient comprising administering to the patient a therapeutically effective amount of an antibody that specifically binds p185$^{HER2}$, wherein the antibody comprises the $V_L$ and $V_H$ domains of an antibody selected from the group consisting of huMAb4D5-3 (SEQ ID NOS. 27 and 28, respectively), huMAb4D5-4 (SEQ ID NOS. 29 and 30, respectively), huMAb4D5-5 (SEQ ID NOS. 1 and 2, respectively), huMAb4D5-6 (SEQ ID NOS. 31 and 32, respectively), huMAb4D5-7 (SEQ ID NOS. 33 and 34, respectively), and huMAb4D5-8 (SEQ ID NOS. 35 and 36, respectively).

4. A method of treating cancer overexpressing p185$^{HER2}$ in a patient comprising (a) administering to the patient a therapeutically effective amount of an antibody that specifically binds p185$^{HER2}$; and further (b) treating the patient with radiation therapy, wherein the antibody comprises the $V_L$ and $V_H$ domains of an antibody selected from the group consisting of huMAb4D5-3 (SEQ ID NOS. 27 and 28, respectively), huMAb4D5-4 (SEQ ID NOS. 29 and 30, respectively), huMAb4D5-5 (SEQ ID NOS. 1 and 2, respectively), huMAb4D5-6 (SEQ ID NOS. 31 and 32, respectively), huMAb4D5-7 (SEQ ID NOS. 33 and 34, respectively), and huMAb4D5-ϵ (SEQ ID NOS. 35 and 36, respectively).

5. A method of treating cancer overexpressing p185$^{HER2}$ in a patient comprising (a) administering to the patient a therapeutically effective amount of an antibody that specifically binds p185$^{HER2}$; and further (b) treating the patient with combined cycles of radiation therapy, wherein the antibody comprises the $V_L$ and $V_H$ domains of huMAb4D5-8 (SEQ ID NOS. 35 and 36, respectively).

* * * * *

UNITED STATES PATENT AND TRADEMARK OFFICE
CERTIFICATE OF CORRECTION

PATENT NO. : 6,719,971 B1
DATED : April 13, 2004
INVENTOR(S) : Carter et al.

It is certified that error appears in the above-identified patent and that said Letters Patent is hereby corrected as shown below:

Column 95,
Line 53, delete "he" and insert therefor -- the --.

Column 96,
Line 52, delete "huMAb4D5-∊"and insert therefor -- HuMAb4D5-8 --.

Signed and Sealed this

Seventeenth Day of August, 2004

JON W. DUDAS
*Acting Director of the United States Patent and Trademark Office*

SEQUENCE LISTING (1) GENERAL INFORMATION:

(iii) NUMBER OF SEQUENCES: 36

(2) INFORMATION FOR SEQ ID NO: 1:

(i) SEQUENCE CHARACTERISTICS:
      (A) LENGTH: 109 amino acids
      (B) TYPE: Amino Acid
      (D) TOPOLOGY: Linear (xi) SEQUENCE DESCRIPTION: SEQ ID NO: 1:

```
Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Asp Val Asn
                20                  25                  30

Thr Ala Val Ala Trp Tyr Gln Gln Lys Pro Gly Lys Ala Pro Lys
                35                  40                  45

Leu Leu Ile Tyr Ser Ala Ser Phe Leu Glu Ser Gly Val Pro Ser
                50                  55                  60

Arg Phe Ser Gly Ser Arg Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90

His Tyr Thr Thr Pro Pro Thr Phe Gly Gln Gly Thr Lys Val Glu
                95                 100                 105

Ile Lys Arg Thr
```

(2) INFORMATION FOR SEQ ID NO: 2:

(i) SEQUENCE CHARACTERISTICS:
      (A) LENGTH: 120 amino acids
      (B) TYPE: Amino Acid
      (D) TOPOLOGY: Linear (xi) SEQUENCE DESCRIPTION: SEQ ID NO: 2:

```
Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Asn Ile Lys
                20                  25                  30

Asp Thr Tyr Ile His Trp Val Arg Gln Ala Pro Gly Lys Gly Leu
                35                  40                  45

Glu Trp Val Ala Arg Ile Tyr Pro Thr Asn Gly Tyr Thr Arg Tyr
                50                  55                  60

Ala Asp Ser Val Lys Gly Arg Phe Thr Ile Ser Ala Asp Thr Ser
                65                  70                  75

Lys Asn Thr Ala Tyr Leu Gln Met Asn Ser Leu Arg Ala Glu Asp
                80                  85                  90

Thr Ala Val Tyr Tyr Cys Ser Arg Trp Gly Gly Asp Gly Phe Tyr
                95                 100                 105

Ala Met Asp Val Trp Gly Gln Gly Thr Leu Val Thr Val Ser Ser
               110                 115                 120
```

(2) INFORMATION FOR SEQ ID NO: 3:

(i) SEQUENCE CHARACTERISTICS:
      (A) LENGTH: 109 amino acids (B) TYPE: Amino Acid
            (D) TOPOLOGY: Linear (xi) SEQUENCE DESCRIPTION: SEQ ID NO: 3:

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Asp Val Ser
                20                  25                  30

Ser Tyr Leu Ala Trp Tyr Gln Gln Lys Pro Gly Lys Ala Pro Lys
                35                  40                  45

Leu Leu Ile Tyr Ala Ala Ser Ser Leu Glu Ser Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90

Tyr Asn Ser Leu Pro Tyr Thr Phe Gly Gln Gly Thr Lys Val Glu
                95                 100                 105

Ile Lys Arg Thr (2) INFORMATION FOR SEQ ID NO: 4:

(i) SEQUENCE CHARACTERISTICS:
        (A) LENGTH: 120 amino acids
        (B) TYPE: Amino Acid
        (D) TOPOLOGY: Linear (xi) SEQUENCE DESCRIPTION: SEQ ID NO: 4:

Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Thr Phe Ser
                20                  25                  30

Asp Tyr Ala Met Ser Trp Val Arg Gln Ala Pro Gly Lys Gly Leu
                35                  40                  45

Glu Trp Val Ala Val Ile Ser Glu Asn Gly Ser Asp Thr Tyr Tyr
                50                  55                  60

Ala Asp Ser Val Lys Gly Arg Phe Thr Ile Ser Arg Asp Asp Ser
                65                  70                  75

Lys Asn Thr Leu Tyr Leu Gln Met Asn Ser Leu Arg Ala Glu Asp
                80                  85                  90

Thr Ala Val Tyr Tyr Cys Ala Arg Asp Arg Gly Gly Ala Val Ser
                95                 100                 105

Tyr Phe Asp Val Trp Gly Gln Gly Thr Leu Val Thr Val Ser Ser
               110                 115                 120

(2) INFORMATION FOR SEQ ID NO: 5:

(i) SEQUENCE CHARACTERISTICS:
        (A) LENGTH: 109 amino acids
        (B) TYPE: Amino Acid
        (D) TOPOLOGY: Linear (xi) SEQUENCE DESCRIPTION: SEQ ID NO: 5:

Asp Ile Val Met Thr Gln Ser His Lys Phe Met Ser Thr Ser Val
 1               5                  10                  15

Gly Asp Arg Val Ser Ile Thr Cys Lys Ala Ser Gln Asp Val Asn
                20                  25                  30

Thr Ala Val Ala Trp Tyr Gln Gln Lys Pro Gly His Ser Pro Lys

```
                     35                  40                  45

Leu Leu Ile Tyr Ser Ala Ser Phe Arg Tyr Thr Gly Val Pro Asp
                 50                  55                  60

Arg Phe Thr Gly Asn Arg Ser Gly Thr Asp Phe Thr Phe Thr Ile
             65                  70                  75

Ser Ser Val Gln Ala Glu Asp Leu Ala Val Tyr Tyr Cys Gln Gln
         80                  85                  90

His Tyr Thr Thr Pro Pro Thr Phe Gly Gly Gly Thr Lys Leu Glu
     95                 100                 105

Ile Lys Arg Ala (2) INFORMATION FOR SEQ ID NO: 6:

(i) SEQUENCE CHARACTERISTICS:
        (A) LENGTH: 120 amino acids
        (B) TYPE: Amino Acid
        (D) TOPOLOGY: Linear (xi) SEQUENCE DESCRIPTION: SEQ ID NO: 6:

Glu Val Gln Leu Gln Gln Ser Gly Pro Glu Leu Val Lys Pro Gly
  1               5                  10                  15

Ala Ser Leu Lys Leu Ser Cys Thr Ala Ser Gly Phe Asn Ile Lys
                 20                  25                  30

Asp Thr Tyr Ile His Trp Val Lys Gln Arg Pro Glu Gln Gly Leu
             35                  40                  45

Glu Trp Ile Gly Arg Ile Tyr Pro Thr Asn Gly Tyr Thr Arg Tyr
         50                  55                  60

Asp Pro Lys Phe Gln Asp Lys Ala Thr Ile Thr Ala Asp Thr Ser
     65                  70                  75

Ser Asn Thr Ala Tyr Leu Gln Val Ser Arg Leu Thr Ser Glu Asp
 80                  85                  90

Thr Ala Val Tyr Tyr Cys Ser Arg Trp Gly Gly Asp Gly Phe Tyr
                 95                 100                 105

Ala Met Asp Tyr Trp Gly Gln Gly Ala Ser Val Thr Val Ser Ser
             110                 115                 120

(2) INFORMATION FOR SEQ ID NO: 7:

(i) SEQUENCE CHARACTERISTICS:
        (A) LENGTH: 27 base pairs
        (B) TYPE: Nucleic Acid
        (C) STRANDEDNESS: Single
        (D) TOPOLOGY: Linear (xi) SEQUENCE DESCRIPTION: SEQ ID NO: 7:

TCCGATATCC AGCTGACCCA GTCTCCA                                          27

(2) INFORMATION FOR SEQ ID NO: 8:

(i) SEQUENCE CHARACTERISTICS:
        (A) LENGTH: 31 base pairs
        (B) TYPE: Nucleic Acid
        (C) STRANDEDNESS: Single
        (D) TOPOLOGY: Linear (xi) SEQUENCE DESCRIPTION: SEQ ID NO: 8:

GTTTGATCTC CAGCTTGGTA CCHSCDCCGA A                                     31

(2) INFORMATION FOR SEQ ID NO: 9:
```

(i) SEQUENCE CHARACTERISTICS:
        (A) LENGTH: 22 base pairs
        (B) TYPE: Nucleic Acid
        (C) STRANDEDNESS: Single
        (D) TOPOLOGY: Linear (xi) SEQUENCE DESCRIPTION: SEQ ID NO: 9:

AGGTSMARCT GCAGSAGTCW GG                                                    22

(2) INFORMATION FOR SEQ ID NO: 10:

(i) SEQUENCE CHARACTERISTICS:
        (A) LENGTH: 34 base pairs
        (B) TYPE: Nucleic Acid
        (C) STRANDEDNESS: Single
        (D) TOPOLOGY: Linear (xi) SEQUENCE DESCRIPTION: SEQ ID NO: 10:

TGAGGAGACG GTGACCGTGG TCCCTTGGCC CCAG                                        34

(2) INFORMATION FOR SEQ ID NO: 11:

(i) SEQUENCE CHARACTERISTICS:
        (A) LENGTH: 36 base pairs
        (B) TYPE: Nucleic Acid
        (C) STRANDEDNESS: Single
        (D) TOPOLOGY: Linear (xi) SEQUENCE DESCRIPTION: SEQ ID NO: 11:

GTAGATAAAT CCTCTAACAC AGCCTATCTG CAAATG                                      36

(2) INFORMATION FOR SEQ ID NO: 12:

(i) SEQUENCE CHARACTERISTICS:
        (A) LENGTH: 36 base pairs
        (B) TYPE: Nucleic Acid
        (C) STRANDEDNESS: Single
        (D) TOPOLOGY: Linear (xi) SEQUENCE DESCRIPTION: SEQ ID NO: 12:

GTAGATAAAT CCAAATCTAC AGCCTATCTG CAAATG                                      36

(2) INFORMATION FOR SEQ ID NO: 13:

(i) SEQUENCE CHARACTERISTICS:
        (A) LENGTH: 36 base pairs
        (B) TYPE: Nucleic Acid
        (C) STRANDEDNESS: Single
        (D) TOPOLOGY: Linear (xi) SEQUENCE DESCRIPTION: SEQ ID NO: 13:

GTAGATAAAT CCTCTTCTAC AGCCTATCTG CAAATG                                      36

(2) INFORMATION FOR SEQ ID NO: 14:

(i) SEQUENCE CHARACTERISTICS:
        (A) LENGTH: 68 base pairs
        (B) TYPE: Nucleic Acid
        (C) STRANDEDNESS: Single
        (D) TOPOLOGY: Linear (xi) SEQUENCE DESCRIPTION: SEQ ID NO: 14:

CTTATAAAGG TGTTTCCACC TATAACCAGA AATTCAAGGA TCGTTTCACG                        50

ATATCCGTAG ATAAATCC                                                          68

(2) INFORMATION FOR SEQ ID NO: 15:

(i) SEQUENCE CHARACTERISTICS:
    (A) LENGTH: 30 base pairs
    (B) TYPE: Nucleic Acid
    (C) STRANDEDNESS: Single
    (D) TOPOLOGY: Linear (xi) SEQUENCE DESCRIPTION: SEQ ID NO: 15:

CTATACCTCC CGTCTGCATT CTGGAGTCCC                                    30

(2) INFORMATION FOR SEQ ID NO: 16:

(i) SEQUENCE CHARACTERISTICS:
        (A) LENGTH: 107 amino acids
        (B) TYPE: Amino Acid
        (D) TOPOLOGY: Linear (xi) SEQUENCE DESCRIPTION: SEQ ID NO: 16:

Asp Ile Gln Met Thr Gln Thr Thr Ser Ser Leu Ser Ala Ser Leu
 1               5                  10                  15

Gly Asp Arg Val Thr Ile Ser Cys Arg Ala Ser Gln Asp Ile Arg
                20                  25                  30

Asn Tyr Leu Asn Trp Tyr Gln Gln Lys Pro Asp Gly Thr Val Lys
                35                  40                  45

Leu Leu Ile Tyr Tyr Thr Ser Arg Leu His Ser Gly Val Pro Ser
                50                  55                  60

Lys Phe Ser Gly Ser Gly Ser Gly Thr Asp Tyr Ser Leu Thr Ile
                65                  70                  75

Ser Asn Leu Glu Gln Glu Asp Ile Ala Thr Tyr Phe Cys Gln Gln
                80                  85                  90

Gly Asn Thr Leu Pro Trp Thr Phe Ala Gly Gly Thr Lys Leu Glu
                95                  100                 105

Ile Lys (2) INFORMATION FOR SEQ ID NO: 17:

(i) SEQUENCE CHARACTERISTICS:
        (A) LENGTH: 107 amino acids
        (B) TYPE: Amino Acid
        (D) TOPOLOGY: Linear (xi) SEQUENCE DESCRIPTION: SEQ ID NO: 17:

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Asp Ile Arg
                20                  25                  30

Asn Tyr Leu Asn Trp Tyr Gln Gln Lys Pro Gly Lys Ala Pro Lys
                35                  40                  45

Leu Leu Ile Tyr Tyr Thr Ser Arg Leu Glu Ser Gly Val Pro Ser
                50                  55                  60

Arg Phe Ser Gly Ser Gly Ser Gly Thr Asp Tyr Thr Leu Thr Ile
                65                  70                  75

Ser Ser Leu Gln Pro Glu Asp Phe Ala Thr Tyr Tyr Cys Gln Gln
                80                  85                  90

Gly Asn Thr Leu Pro Trp Thr Phe Gly Gln Gly Thr Lys Val Glu
                95                  100                 105

Ile Lys (2) INFORMATION FOR SEQ ID NO: 18:

(i) SEQUENCE CHARACTERISTICS:
            (A) LENGTH: 107 amino acids
            (B) TYPE: Amino Acid
            (D) TOPOLOGY: Linear (xi) SEQUENCE DESCRIPTION: SEQ ID NO: 18:

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Ser Ile Ser
                20                  25                  30

Asn Tyr Leu Ala Trp Tyr Gln Gln Lys Pro Gly Lys Ala Pro Lys
                35                  40                  45

Leu Leu Ile Tyr Ala Ala Ser Ser Leu Glu Ser Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90

Tyr Asn Ser Leu Pro Trp Thr Phe Gly Gln Gly Thr Lys Val Glu
                95                  100                 105

Ile Lys (2) INFORMATION FOR SEQ ID NO: 19:

(i) SEQUENCE CHARACTERISTICS:
            (A) LENGTH: 122 amino acids
            (B) TYPE: Amino Acid
            (D) TOPOLOGY: Linear (xi) SEQUENCE DESCRIPTION: SEQ ID NO: 19:

Glu Val Gln Leu Gln Gln Ser Gly Pro Glu Leu Val Lys Pro Gly
 1               5                  10                  15

Ala Ser Met Lys Ile Ser Cys Lys Ala Ser Gly Tyr Ser Phe Thr
                20                  25                  30

Gly Tyr Thr Met Asn Trp Val Lys Gln Ser His Gly Lys Asn Leu
                35                  40                  45

Glu Trp Met Gly Leu Ile Asn Pro Tyr Lys Gly Val Ser Thr Tyr
                50                  55                  60

Asn Gln Lys Phe Lys Asp Lys Ala Thr Leu Thr Val Asp Lys Ser
                65                  70                  75

Ser Ser Thr Ala Tyr Met Glu Leu Leu Ser Leu Thr Ser Glu Asp
                80                  85                  90

Ser Ala Val Tyr Tyr Cys Ala Arg Ser Gly Tyr Tyr Gly Asp Ser
                95                  100                 105

Asp Trp Tyr Phe Asp Val Trp Gly Ala Gly Thr Thr Val Thr Val
                110                 115                 120

Ser Ser (2) INFORMATION FOR SEQ ID NO: 20:

(i) SEQUENCE CHARACTERISTICS:
            (A) LENGTH: 122 amino acids
            (B) TYPE: Amino Acid
            (D) TOPOLOGY: Linear (xi) SEQUENCE DESCRIPTION: SEQ ID NO: 20:

Glu Val Gln Leu Val Glu Ser Gly Gly Gly Leu Val Gln Pro Gly
 1               5                  10                  15

```
Gly Ser Leu Arg Leu Ser Cys Ala Ala Ser Gly Tyr Ser Phe Thr
            20                  25                  30

Gly Tyr Thr Met Asn Trp Val Arg Gln Ala Pro Gly Lys Gly Leu
            35                  40                  45

Glu Trp Val Ala Leu Ile Asn Pro Tyr Lys Gly Val Ser Thr Tyr
            50                  55                  60

Asn Gln Lys Phe Lys Asp Arg Phe Thr Ile Ser Val Asp Lys Ser
            65                  70                  75

Lys Asn Thr Ala Tyr Leu Gln Met Asn Ser Leu Arg Ala Glu Asp
            80                  85                  90

Thr Ala Val Tyr Tyr Cys Ala Arg Ser Gly Tyr Tyr Gly Asp Ser
            95                 100                 105

Asp Trp Tyr Phe Asp Val Trp Gly Gln Gly Thr Leu Val Thr Val
           110                 115                 120

Ser Ser
```

(2) INFORMATION FOR SEQ ID NO: 21:

(i) SEQUENCE CHARACTERISTICS:
        (A) LENGTH: 122 amino acids
        (B) TYPE: Amino Acid
        (D) TOPOLOGY: Linear (xi) SEQUENCE DESCRIPTION: SEQ ID NO: 21:

```
Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu
            35                  40                  45

Glu Trp Val Ser Val Ile Ser Gly Asp Gly Ser Thr Tyr Tyr
            50                  55                  60

Ala Asp Ser Val Lys Gly Arg Phe Thr Ile Ser Arg Asp Asn Ser
            65                  70                  75

Lys Asn Thr Leu Tyr Leu Gln Met Asn Ser Leu Arg Ala Glu Asp
            80                  85                  90

Thr Ala Val Tyr Tyr Cys Ala Arg Gly Arg Val Gly Tyr Ser Leu
            95                 100                 105

Ser Gly Leu Tyr Asp Tyr Trp Gly Gln Gly Thr Leu Val Thr Val
           110                 115                 120

Ser Ser
```

(2) INFORMATION FOR SEQ ID NO: 22:

(i) SEQUENCE CHARACTERISTICS:
        (A) LENGTH: 454 amino acids
        (B) TYPE: Amino Acid
        (D) TOPOLOGY: Linear (xi) SEQUENCE DESCRIPTION: SEQ ID NO: 22:

```
Gln Val Gln Leu Gln Gln Ser Gly Pro Glu Leu Val Lys Pro Gly
 1               5                  10                  15

Ala Ser Val Lys Ile Ser Cys Lys Thr Ser Gly Tyr Thr Phe Thr
            20                  25                  30

Glu Tyr Thr Met His Trp Met Lys Gln Ser His Gly Lys Ser Leu
            35                  40                  45
```

-continued

```
Glu Trp Ile Gly Gly Phe Asn Pro Lys Asn Gly Gly Ser Ser His
                 50                  55                  60

Asn Gln Arg Phe Met Asp Lys Ala Thr Leu Ala Val Asp Lys Ser
             65                  70                  75

Thr Ser Thr Ala Tyr Met Glu Leu Arg Ser Leu Thr Ser Glu Asp
             80                  85                  90

Ser Gly Ile Tyr Tyr Cys Ala Arg Trp Arg Gly Leu Asn Tyr Gly
             95                 100                 105

Phe Asp Val Arg Tyr Phe Asp Val Trp Gly Ala Gly Thr Thr Val
            110                 115                 120

Thr Val Ser Ser Ala Ser Thr Lys Gly Pro Ser Val Phe Pro Leu
            125                 130                 135

Ala Pro Ser Ser Lys Ser Thr Ser Gly Gly Thr Ala Ala Leu Gly
            140                 145                 150

Cys Leu Val Lys Asp Tyr Phe Pro Glu Pro Val Thr Val Ser Trp
            155                 160                 165

Asn Ser Gly Ala Leu Thr Ser Gly Val His Thr Phe Pro Ala Val
            170                 175                 180

Leu Gln Ser Ser Gly Leu Tyr Ser Leu Ser Ser Val Val Thr Val
            185                 190                 195

Pro Ser Ser Ser Leu Gly Thr Gln Thr Tyr Ile Cys Asn Val Asn
            200                 205                 210

His Lys Pro Ser Asn Thr Lys Val Asp Lys Lys Val Glu Pro Lys
            215                 220                 225

Ser Cys Asp Lys Thr His Thr Cys Pro Pro Cys Pro Ala Pro Glu
            230                 235                 240

Leu Leu Gly Gly Pro Ser Val Phe Leu Phe Pro Pro Lys Pro Lys
            245                 250                 255

Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr
            275                 280                 285

Val Asp Gly Val Glu Val His Asn Ala Lys Thr Lys Pro Arg Glu
            290                 295                 300

Glu Gln Tyr Asn Ser Thr Tyr Arg Val Val Ser Val Leu Thr Val
            305                 310                 315

Leu His Gln Asp Trp Leu Asn Gly Lys Glu Tyr Lys Cys Lys Val
            320                 325                 330

Ser Asn Lys Ala Leu Pro Ala Pro Ile Glu Lys Thr Ile Ser Lys
            335                 340                 345

Ala Lys Gly Gln Pro Arg Glu Pro Gln Val Tyr Thr Leu Pro Pro
            350                 355                 360

Ser Arg Glu Glu Met Thr Lys Asn Gln Val Ser Leu Thr Cys Leu
            365                 370                 375

Val Lys Gly Phe Tyr Pro Ser Asp Ile Ala Val Glu Trp Glu Ser
            380                 385                 390

Asn Gly Gln Pro Glu Asn Asn Tyr Lys Thr Thr Pro Pro Val Leu
            395                 400                 405

Asp Ser Asp Gly Ser Phe Phe Leu Tyr Ser Lys Leu Thr Val Asp
            410                 415                 420

Lys Ser Arg Trp Gln Gln Gly Asn Val Phe Ser Cys Ser Val Met
            425                 430                 435

His Glu Ala Leu His Asn His Tyr Thr Gln Lys Ser Leu Ser Leu
```

-continued

```
                  440                 445                 450
Ser Pro Gly Lys (2) INFORMATION FOR SEQ ID NO: 23:

(i) SEQUENCE CHARACTERISTICS:
        (A) LENGTH: 469 amino acids
        (B) TYPE: Amino Acid
        (D) TOPOLOGY: Linear (xi) SEQUENCE DESCRIPTION: SEQ ID NO: 23:

Met Gly Trp Ser Cys Ile Ile Leu Phe Leu Val Ala Thr Ala Thr
 1               5                  10                  15

Gly Val His Ser Glu Val Gln Leu Val Glu Ser Gly Gly Gly Leu
                20                  25                  30

Val Gln Pro Gly Gly Ser Leu Arg Leu Ser Cys Ala Thr Ser Gly
                35                  40                  45

Tyr Thr Phe Thr Glu Tyr Thr Met His Trp Met Arg Gln Ala Pro
                50                  55                  60

Gly Lys Gly Leu Glu Trp Val Ala Gly Ile Asn Pro Lys Asn Gly
                65                  70                  75

Gly Thr Ser His Asn Gln Arg Phe Met Asp Arg Phe Thr Ile Ser
                80                  85                  90

Val Asp Lys Ser Thr Ser Thr Ala Tyr Met Gln Met Asn Ser Leu
                95                  100                 105

Arg Ala Glu Asp Thr Ala Val Tyr Tyr Cys Ala Arg Trp Arg Gly
                110                 115                 120

Leu Asn Tyr Gly Phe Asp Val Arg Tyr Phe Asp Val Trp Gly Gln
                125                 130                 135

Gly Thr Leu Val Thr Val Ser Ser Ala Ser Thr Lys Gly Pro Ser
                140                 145                 150

Val Phe Pro Leu Ala Pro Cys Ser Arg Ser Thr Ser Glu Ser Thr
                155                 160                 165

Ala Ala Leu Gly Cys Leu Val Lys Asp Tyr Phe Pro Glu Pro Val
                170                 175                 180

Thr Val Ser Trp Asn Ser Gly Ala Leu Thr Ser Gly Val His Thr
                185                 190                 195

Phe Pro Ala Val Leu Gln Ser Ser Gly Leu Tyr Ser Leu Ser Ser
                200                 205                 210

Val Val Thr Val Thr Ser Ser Asn Phe Gly Thr Gln Thr Tyr Thr
                215                 220                 225

Cys Asn Val Asp His Lys Pro Ser Asn Thr Lys Val Asp Lys Thr
                230                 235                 240

Val Glu Arg Lys Cys Cys Val Glu Cys Pro Pro Cys Pro Ala Pro
                245                 250                 255

Pro Val Ala Gly Pro Ser Val Phe Leu Phe Pro Pro Lys Pro Lys
                260                 265                 270

Asp Thr Leu Met Ile Ser Arg Thr Pro Glu Val Thr Cys Val Val
                275                 280                 285

Val Asp Val Ser His Glu Asp Pro Glu Val Gln Phe Asn Trp Tyr
                290                 295                 300

Val Asp Gly Met Glu Val His Asn Ala Lys Thr Lys Pro Arg Glu
                305                 310                 315

Glu Gln Phe Asn Ser Thr Phe Arg Val Val Ser Val Leu Thr Val
                320                 325                 330
```

```
Val His Gln Asp Trp Leu Asn Gly Lys Glu Tyr Lys Cys Lys Val
            335                 340                 345

Ser Asn Lys Gly Leu Pro Ala Pro Ile Glu Lys Thr Ile Ser Lys
            350                 355                 360

Thr Lys Gly Gln Pro Arg Glu Pro Gln Val Tyr Thr Leu Pro Pro
            365                 370                 375

Ser Arg Glu Glu Met Thr Lys Asn Gln Val Ser Leu Thr Cys Leu
            380                 385                 390

Val Lys Gly Phe Tyr Pro Ser Asp Ile Ala Val Glu Trp Glu Ser
            395                 400                 405

Asn Gly Gln Pro Glu Asn Asn Tyr Lys Thr Thr Pro Pro Met Leu
            410                 415                 420

Asp Ser Asp Gly Ser Phe Phe Leu Tyr Ser Lys Leu Thr Val Asp
            425                 430                 435

Lys Ser Arg Trp Gln Gln Gly Asn Val Phe Ser Cys Ser Val Met
            440                 445                 450

His Glu Ala Leu His Asn His Tyr Thr Gln Lys Ser Leu Ser Leu
            455                 460                 465

Ser Pro Gly Lys (2) INFORMATION FOR SEQ ID NO: 24:

(i) SEQUENCE CHARACTERISTICS:
        (A) LENGTH: 214 amino acids
        (B) TYPE: Amino Acid
        (D) TOPOLOGY: Linear (xi) SEQUENCE DESCRIPTION: SEQ ID NO: 24:

Asp Val Gln Met Thr Gln Thr Thr Ser Ser Leu Ser Ala Ser Leu
 1               5                  10                  15

Gly Asp Arg Val Thr Ile Asn Cys Arg Ala Ser Gln Asp Ile Asn
            20                  25                  30

Asn Tyr Leu Asn Trp Tyr Gln Gln Lys Pro Asn Gly Thr Val Lys
            35                  40                  45

Leu Leu Ile Tyr Tyr Thr Ser Thr Leu His Ser Gly Val Pro Ser
            50                  55                  60

Arg Phe Ser Gly Ser Gly Ser Gly Thr Asp Tyr Ser Leu Thr Ile
            65                  70                  75

Ser Asn Leu Asp Gln Glu Asp Ile Ala Thr Tyr Phe Cys Gln Gln
            80                  85                  90

Gly Asn Thr Leu Pro Pro Thr Phe Gly Gly Gly Thr Lys Val Glu
            95                  100                 105

Ile Lys Arg Thr Val Ala Ala Pro Ser Val Phe Ile Phe Pro Pro
            110                 115                 120

Ser Asp Glu Gln Leu Lys Ser Gly Thr Ala Ser Val Val Cys Leu
            125                 130                 135

Leu Asn Asn Phe Tyr Pro Arg Glu Ala Lys Val Gln Trp Lys Val
            140                 145                 150

Asp Asn Ala Leu Gln Ser Gly Asn Ser Gln Glu Ser Val Thr Glu
            155                 160                 165

Gln Asp Ser Lys Asp Ser Thr Tyr Ser Leu Ser Ser Thr Leu Thr
            170                 175                 180

Leu Ser Lys Ala Asp Tyr Glu Lys His Lys Val Tyr Ala Cys Glu
            185                 190                 195
```

```
Val Thr His Gln Gly Leu Ser Ser Pro Val Thr Lys Ser Phe Asn
            200                 205                 210

Arg Gly Glu Cys
```

(2) INFORMATION FOR SEQ ID NO: 25:

(i) SEQUENCE CHARACTERISTICS:
        (A) LENGTH: 233 amino acids
        (B) TYPE: Amino Acid
        (D) TOPOLOGY: Linear (xi) SEQUENCE DESCRIPTION: SEQ ID NO: 25:

```
Met Gly Trp Ser Cys Ile Ile Leu Phe Leu Val Ala Thr Ala Thr
 1               5                  10                  15

Gly Val His Ser Asp Ile Gln Met Thr Gln Ser Pro Ser Ser Leu
            20                  25                  30

Ser Ala Ser Val Gly Asp Arg Val Thr Ile Thr Cys Arg Ala Ser
            35                  40                  45

Gln Asp Ile Asn Asn Tyr Leu Asn Trp Tyr Gln Gln Lys Pro Gly
            50                  55                  60

Lys Ala Pro Lys Leu Leu Ile Tyr Tyr Thr Ser Thr Leu His Ser
            65                  70                  75

Gly Val Pro Ser Arg Phe Ser Gly Ser Gly Ser Gly Thr Asp Tyr
            80                  85                  90

Thr Leu Thr Ile Ser Ser Leu Gln Pro Glu Asp Phe Ala Thr Tyr
            95                  100                 105

Tyr Cys Gln Gln Gly Asn Thr Leu Pro Pro Thr Phe Gly Gln Gly
            110                 115                 120

Thr Lys Val Glu Ile Lys Arg Thr Val Ala Ala Pro Ser Val Phe
            125                 130                 135

Ile Phe Pro Pro Ser Asp Glu Gln Leu Lys Ser Gly Thr Ala Ser
            140                 145                 150

Val Val Cys Leu Leu Asn Asn Phe Tyr Pro Arg Glu Ala Lys Val
            155                 160                 165

Gln Trp Lys Val Asp Asn Ala Leu Gln Ser Gly Asn Ser Gln Glu
            170                 175                 180

Ser Val Thr Glu Gln Asp Ser Lys Asp Ser Thr Tyr Ser Leu Ser
            185                 190                 195

Ser Thr Leu Thr Leu Ser Lys Ala Asp Tyr Glu Lys His Lys Val
            200                 205                 210

Tyr Ala Cys Glu Val Thr His Gln Gly Leu Ser Ser Pro Val Thr
            215                 220                 225

Lys Ser Phe Asn Arg Gly Glu Cys
            230
```

(2) INFORMATION FOR SEQ ID NO: 26:

(i) SEQUENCE CHARACTERISTICS:
        (A) LENGTH: 122 amino acids
        (B) TYPE: Amino Acid
        (D) TOPOLOGY: Linear (xi) SEQUENCE DESCRIPTION: SEQ ID NO: 26:

```
Glu Val Gln Leu Val Glu Ser Gly Gly Gly Leu Val Gln Pro Gly
 1               5                  10                  15

Gly Ser Leu Arg Leu Ser Cys Ala Ala Ser Gly Tyr Ser Phe Thr
            20                  25                  30
```

```
Gly Tyr Thr Met Asn Trp Val Arg Gln Ala Pro Gly Lys Gly Leu
                 35                  40                  45

Glu Trp Val Ala Leu Ile Asn Pro Tyr Lys Gly Val Thr Thr Tyr
                 50                  55                  60

Ala Asp Ser Val Lys Gly Arg Phe Thr Ile Ser Val Asp Lys Ser
                 65                  70                  75

Lys Asn Thr Ala Tyr Leu Gln Met Asn Ser Leu Arg Ala Glu Asp
                 80                  85                  90

Thr Ala Val Tyr Tyr Cys Ala Arg Ser Gly Tyr Tyr Gly Asp Ser
                 95                 100                 105

Asp Trp Tyr Phe Asp Val Trp Gly Gln Gly Thr Leu Val Thr Val
                110                 115                 120

Ser Ser
```

(2) INFORMATION FOR SEQ ID NO: 27:

(i) SEQUENCE CHARACTERISTICS:
        (A) LENGTH: 109 amino acids
        (B) TYPE: Amino Acid
        (D) TOPOLOGY: Linear (xi) SEQUENCE DESCRIPTION: SEQ ID NO: 27:

```
Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Asp Val Asn
                 20                  25                  30

Thr Ala Val Ala Trp Tyr Gln Gln Lys Pro Gly Lys Ala Pro Lys
                 35                  40                  45

Leu Leu Ile Tyr Ser Ala Ser Phe Leu Glu Ser Gly Val Pro Ser
                 50                  55                  60

Arg Phe Ser Gly Ser Gly Ser Gly Thr Asp Phe Thr Leu Thr Ile
                 65                  70                  75

Ser Ser Leu Gln Pro Glu Asp Phe Ala Thr Tyr Tyr Cys Gln Gln
                 80                  85                  90

His Tyr Thr Thr Pro Pro Thr Phe Gly Gln Gly Thr Lys Val Glu
                 95                 100                 105

Ile Lys Arg Thr
```

(2) INFORMATION FOR SEQ ID NO: 28:

(i) SEQUENCE CHARACTERISTICS:
        (A) LENGTH: 120 amino acids
        (B) TYPE: Amino Acid
        (D) TOPOLOGY: Linear (xi) SEQUENCE DESCRIPTION: SEQ ID NO: 28:

```
Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Asn Ile Lys
                 20                  25                  30

Asp Thr Tyr Ile His Trp Val Arg Gln Ala Pro Gly Lys Gly Leu
                 35                  40                  45

Glu Trp Val Ala Arg Ile Tyr Pro Thr Asn Gly Tyr Thr Arg Tyr
                 50                  55                  60

Ala Asp Ser Val Lys Gly Arg Phe Thr Ile Ser Ala Asp Thr Ser
                 65                  70                  75

Lys Asn Thr Ala Tyr Leu Gln Met Asn Ser Leu Arg Ala Glu Asp
```

```
                     80              85              90
Thr Ala Val Tyr Tyr Cys Ser Arg Trp Gly Gly Asp Gly Phe Tyr
                         95             100             105
Ala Met Asp Val Trp Gly Gln Gly Thr Leu Val Thr Val Ser Ser
                    110             115             120
```

(2) INFORMATION FOR SEQ ID NO: 29:

(i) SEQUENCE CHARACTERISTICS:
        (A) LENGTH: 109 amino acids
        (B) TYPE: Amino Acid
        (D) TOPOLOGY: Linear (xi) SEQUENCE DESCRIPTION: SEQ ID NO: 29:

```
Asp Ile Gln Met Thr Gln Ser Pro Ser Ser Leu Ser Ala Ser Val
 1               5                  10                  15
Gly Asp Arg Val Thr Ile Thr Cys Arg Ala Ser Gln Asp Val Asn
                20                  25                  30
Thr Ala Val Ala Trp Tyr Gln Gln Lys Pro Gly Lys Ala Pro Lys
                35                  40                  45
Leu Leu Ile Tyr Ser Ala Ser Phe Leu Glu Ser Gly Val Pro Ser
                50                  55                  60
Arg Phe Ser Gly Ser Arg Ser Gly Thr Asp Phe Thr Leu Thr Ile
                65                  70                  75
Ser Ser Leu Gln Pro Glu Asp Phe Ala Thr Tyr Tyr Cys Gln Gln
                80                  85                  90
His Tyr Thr Thr Pro Pro Thr Phe Gly Gln Gly Thr Lys Val Glu
                95                 100                 105
Ile Lys Arg Thr
```

(2) INFORMATION FOR SEQ ID NO: 30:

(i) SEQUENCE CHARACTERISTICS:
        (A) LENGTH: 120 amino acids
        (B) TYPE: Amino Acid
        (D) TOPOLOGY: Linear (xi) SEQUENCE DESCRIPTION: SEQ ID NO: 30:

```
Glu Val Gln Leu Val Glu Ser Gly Gly Gly Leu Val Gln Pro Gly
 1               5                  10                  15
Gly Ser Leu Arg Leu Ser Cys Ala Ala Ser Gly Phe Asn Ile Lys
                20                  25                  30
Asp Thr Tyr Ile His Trp Val Arg Gln Ala Pro Gly Lys Gly Leu
                35                  40                  45
Glu Trp Val Ala Arg Ile Tyr Pro Thr Asn Gly Tyr Thr Arg Tyr
                50                  55                  60
Ala Asp Ser Val Lys Gly Arg Phe Thr Ile Ser Ala Asp Thr Ser
                65                  70                  75
Lys Asn Thr Leu Tyr Leu Gln Met Asn Ser Leu Arg Ala Glu Asp
                80                  85                  90
Thr Ala Val Tyr Tyr Cys Ser Arg Trp Gly Gly Asp Gly Phe Tyr
                95                 100                 105
Ala Met Asp Val Trp Gly Gln Gly Thr Leu Val Thr Val Ser Ser
               110                 115                 120
```

(2) INFORMATION FOR SEQ ID NO: 31:

(i) SEQUENCE CHARACTERISTICS:

(A) LENGTH: 109 amino acids
(B) TYPE: Amino Acid
(D) TOPOLOGY: Linear (xi) SEQUENCE DESCRIPTION: SEQ ID NO: 31:

Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Asp Val Asn
                20                  25                  30

Thr Ala Val Ala Trp Tyr Gln Gln Lys Pro Gly Lys Ala Pro Lys
                35                  40                  45

Leu Leu Ile Tyr Ser Ala Ser Phe Leu Tyr Ser Gly Val Pro Ser
                50                  55                  60

Arg Phe Ser Gly Ser Arg Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90

His Tyr Thr Thr Pro Pro Thr Phe Gly Gln Gly Thr Lys Val Glu
                95                  100                 105

Ile Lys Arg Thr (2) INFORMATION FOR SEQ ID NO: 32:

(i) SEQUENCE CHARACTERISTICS:
        (A) LENGTH: 120 amino acids
        (B) TYPE: Amino Acid
        (D) TOPOLOGY: Linear (xi) SEQUENCE DESCRIPTION: SEQ ID NO: 32:

Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Asn Ile Lys
                20                  25                  30

Asp Thr Tyr Ile His Trp Val Arg Gln Ala Pro Gly Lys Gly Leu
                35                  40                  45

Glu Trp Val Ala Arg Ile Tyr Pro Thr Asn Gly Tyr Thr Arg Tyr
                50                  55                  60

Ala Asp Ser Val Lys Gly Arg Phe Thr Ile Ser Ala Asp Thr Ser
                65                  70                  75

Lys Asn Thr Ala Tyr Leu Gln Met Asn Ser Leu Arg Ala Glu Asp
                80                  85                  90

Thr Ala Val Tyr Tyr Cys Ser Arg Trp Gly Gly Asp Gly Phe Tyr
                95                  100                 105

Ala Met Asp Val Trp Gly Gln Gly Thr Leu Val Thr Val Ser Ser
                110                 115                 120

(2) INFORMATION FOR SEQ ID NO: 33:

(i) SEQUENCE CHARACTERISTICS:
        (A) LENGTH: 109 amino acids
        (B) TYPE: Amino Acid
        (D) TOPOLOGY: Linear (xi) SEQUENCE DESCRIPTION: SEQ ID NO: 33:

Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Asp Val Asn
                20                  25                  30

```
Thr Ala Val Ala Trp Tyr Gln Gln Lys Pro Gly Lys Ala Pro Lys
             35                  40                  45

Leu Leu Ile Tyr Ser Ala Ser Phe Leu Glu Ser Gly Val Pro Ser
             50                  55                  60

Arg Phe Ser Gly Ser Arg Ser Gly Thr Asp Phe Thr Leu Thr Ile
             65                  70                  75

Ser Ser Leu Gln Pro Glu Asp Phe Ala Thr Tyr Tyr Cys Gln Gln
             80                  85                  90

His Tyr Thr Thr Pro Pro Thr Phe Gly Gln Gly Thr Lys Val Glu
             95                 100                 105

Ile Lys Arg Thr (2) INFORMATION FOR SEQ ID NO: 34:

(i) SEQUENCE CHARACTERISTICS:
        (A) LENGTH: 120 amino acids
        (B) TYPE: Amino Acid
        (D) TOPOLOGY: Linear (xi) SEQUENCE DESCRIPTION: SEQ ID NO: 34:

Glu Val Gln Leu Val Glu Ser Gly Gly Gly Leu Val Gln Pro Gly
 1           5                  10                  15

Gly Ser Leu Arg Leu Ser Cys Ala Ala Ser Gly Phe Asn Ile Lys
             20                  25                  30

Asp Thr Tyr Ile His Trp Val Arg Gln Ala Pro Gly Lys Gly Leu
             35                  40                  45

Glu Trp Val Ala Arg Ile Tyr Pro Thr Asn Gly Tyr Thr Arg Tyr
             50                  55                  60

Ala Asp Ser Val Lys Gly Arg Phe Thr Ile Ser Ala Asp Thr Ser
             65                  70                  75

Lys Asn Thr Ala Tyr Leu Gln Met Asn Ser Leu Arg Ala Glu Asp
             80                  85                  90

Thr Ala Val Tyr Tyr Cys Ser Arg Trp Gly Gly Asp Gly Phe Tyr
             95                 100                 105

Ala Met Asp Tyr Trp Gly Gln Gly Thr Leu Val Thr Val Ser Ser
            110                 115                 120

(2) INFORMATION FOR SEQ ID NO: 35:

(i) SEQUENCE CHARACTERISTICS:
        (A) LENGTH: 109 amino acids
        (B) TYPE: Amino Acid
        (D) TOPOLOGY: Linear (xi) SEQUENCE DESCRIPTION: SEQ ID NO: 35:

Asp Ile Gln Met Thr Gln Ser Pro Ser Ser Leu Ser Ala Ser Val
 1           5                  10                  15

Gly Asp Arg Val Thr Ile Thr Cys Arg Ala Ser Gln Asp Val Asn
             20                  25                  30

Thr Ala Val Ala Trp Tyr Gln Gln Lys Pro Gly Lys Ala Pro Lys
             35                  40                  45

Leu Leu Ile Tyr Ser Ala Ser Phe Leu Tyr Ser Gly Val Pro Ser
             50                  55                  60

Arg Phe Ser Gly Ser Arg Ser Gly Thr Asp Phe Thr Leu Thr Ile
             65                  70                  75

Ser Ser Leu Gln Pro Glu Asp Phe Ala Thr Tyr Tyr Cys Gln Gln
             80                  85                  90
```

-continued

```
His Tyr Thr Thr Pro Pro Thr Phe Gly Gln Gly Thr Lys Val Glu
                95                 100                 105

Ile Lys Arg Thr (2) INFORMATION FOR SEQ ID NO: 36:

(i) SEQUENCE CHARACTERISTICS:
        (A) LENGTH: 120 amino acids
        (B) TYPE: Amino Acid
        (D) TOPOLOGY: Linear (xi) SEQUENCE DESCRIPTION: SEQ ID NO: 36:

Glu Val Gln Leu Val Glu Ser Gly Gly Leu Val Gln Pro Gly
  1               5                 10                 15

Gly Ser Leu Arg Leu Ser Cys Ala Ala Ser Gly Phe Asn Ile Lys
                20                 25                 30

Asp Thr Tyr Ile His Trp Val Arg Gln Ala Pro Gly Lys Gly Leu
                35                 40                 45

Glu Trp Val Ala Arg Ile Tyr Pro Thr Asn Gly Tyr Thr Arg Tyr
                50                 55                 60

Ala Asp Ser Val Lys Gly Arg Phe Thr Ile Ser Ala Asp Thr Ser
                65                 70                 75

Lys Asn Thr Ala Tyr Leu Gln Met Asn Ser Leu Arg Ala Glu Asp
                80                 85                 90

Thr Ala Val Tyr Tyr Cys Ser Arg Trp Gly Gly Asp Gly Phe Tyr
                95                 100                105

Ala Met Asp Tyr Trp Gly Gln Gly Thr Leu Val Thr Val Ser Ser
                110                115                120
```